United States Patent
Hung et al.

(10) Patent No.: US 10,451,610 B2
(45) Date of Patent: Oct. 22, 2019

(54) PREDICTION OF RESPONSE TO PARP INHIBITORS AND COMBINATIONAL THERAPY TARGETING C-MET AND PARP1

(71) Applicant: Board of Regents, The University of Texas System, Austin, TX (US)

(72) Inventors: Mien-Chie Hung, Houston, TX (US); Yi Du, Houston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 258 days.

(21) Appl. No.: 15/514,928

(22) PCT Filed: Sep. 29, 2015

(86) PCT No.: PCT/US2015/052966
§ 371 (c)(1),
(2) Date: Mar. 28, 2017

(87) PCT Pub. No.: WO2016/054055
PCT Pub. Date: Apr. 7, 2016

(65) Prior Publication Data
US 2017/0219565 A1    Aug. 3, 2017

Related U.S. Application Data

(60) Provisional application No. 62/057,037, filed on Sep. 29, 2014.

(51) Int. Cl.
*G01N 33/50* (2006.01)
*A61K 45/06* (2006.01)
(Continued)

(52) U.S. Cl.
CPC ...... *G01N 33/5029* (2013.01); *A61K 31/4184* (2013.01); *A61K 31/444* (2013.01);
(Continued)

(58) Field of Classification Search
None
See application file for complete search history.

(56) References Cited

U.S. PATENT DOCUMENTS

2009/0258442 A1  10/2009  Polakiewicz et al.
2011/0104256 A1   5/2011  Wang et al.
(Continued)

FOREIGN PATENT DOCUMENTS

WO  WO 2013-052006  4/2013
WO  WO 2014-052550  4/2014

OTHER PUBLICATIONS

Anders et al., "Pharmacokinetics and efficacy of PEGylated liposomal doxorubicin in an intracranial model of breast cancer," *PLoS One*, 8:e61359, 2013.
(Continued)

*Primary Examiner* — Karl J Puttlitz
(74) *Attorney, Agent, or Firm* — Parker Highlander PLLC

(57) ABSTRACT

Provided herein are methods for identifying and treating cancers that are resistant to PARP inhibition. Methods for sensitizing cancers to a PARP inhibitor therapy are also provided. In some aspects, PARP inhibitor cancers are treated with a PARP inhibitor therapy in combination with a c-Met inhibitor therapy.

18 Claims, 50 Drawing Sheets
Specification includes a Sequence Listing.

(51) Int. Cl.
| | |
|---|---|
| A61K 31/4184 | (2006.01) |
| A61K 31/4425 | (2006.01) |
| A61K 31/444 | (2006.01) |
| A61K 31/5377 | (2006.01) |
| A61K 35/28 | (2015.01) |
| B01L 3/00 | (2006.01) |
| C12M 1/32 | (2006.01) |
| C12M 1/26 | (2006.01) |
| C12M 1/34 | (2006.01) |
| C12M 1/00 | (2006.01) |
| C12N 5/00 | (2006.01) |
| C12N 5/079 | (2010.01) |
| C12N 5/0775 | (2010.01) |
| G01N 33/569 | (2006.01) |

(52) U.S. Cl.
CPC ...... *A61K 31/4425* (2013.01); *A61K 31/5377* (2013.01); *A61K 35/28* (2013.01); *A61K 45/06* (2013.01); *B01L 3/502761* (2013.01); *C12M 23/12* (2013.01); *C12M 33/14* (2013.01); *C12M 41/46* (2013.01); *C12M 47/04* (2013.01); *C12N 5/0068* (2013.01); *C12N 5/0087* (2013.01); *C12N 5/0622* (2013.01); *C12N 5/0662* (2013.01); *G01N 33/56966* (2013.01); *C12N 2500/00* (2013.01)

(56) References Cited

U.S. PATENT DOCUMENTS

| | | |
|---|---|---|
| 2012/0130144 A1* | 5/2012 | Sherman ............... A61K 31/17 600/1 |
| 2013/0309685 A1 | 11/2013 | Iskander |
| 2014/0199292 A1 | 7/2014 | Bertolotto-Ballotti et al. |

OTHER PUBLICATIONS

Anders et al., "Poly(ADP-Ribose) polymerase inhibition: "targeted" therapy for triple-negative breast cancer," *Clin. Cancer Res.*, 16:4702-4710, 2010.
Birchmeier et al., "Met, metastasis, motility and more," *Nat. Rev. Mol. Cell. Biol.*, 4:915-925, 2003.
Boccaccio and Comoglio, "Invasive growth: a MET-driven genetic programme for cancer and stem cells," *Nat. Rev. Cancer*, 6:637-645, 2006.
Bryant et al., "Specific killing of BRCA2-deficient tumours with inhibitors of poly(ADP-ribose) polymerase," *Nature*, 434:913-917, 2005.
Casaletto and McClatchey, "Spatial regulation of receptor tyrosine kinases in development and cancer," *Nat. Rev. Cancer*, 12:387-400, 2012.
Castaldi et al., "How appropriate is the use of rehabilitation facilities? Assessment by an evaluation tool based on the AEP protocol," *J. Prev. Med. Hyg.*, 51:116-120, 2010.
Christensen et al., "c-Met as a target for human cancer and characterization of inhibitors for therapeutic intervention," *Cancer Lett.*, 225:1-26, 2005.
Donawho et al., "ABT-888, an orally active poly(ADP-ribose) polymerase inhibitor that potentiates DNA-damaging agents in preclinical tumor models," *Clin. Cancer Res.*, 13:2728-2737, 2007.
Du et al.,"Syntaxin 6-mediated Golgi translocation plays an important role in nuclear functions of EGFR through microtubule-dependent trafficking," *Oncogene*, 33:756-770, 2014.
Farmer et al., "Targeting the DNA repair defect in BRCA mutant cells as a therapeutic strategy," *Nature*, 434:917-921, 2005.
Fischer et al., "Reactive oxygen species mediate Met receptor transactivation by G protein-coupled receptors and the epidermal growth factor receptor cells," *J. Biol. Chem.*, 279:28970-28978, 2004.
Gastaldi et al., "The Met oncogene and basal-like breast cancer: another culprit to watch out for?" *Breast Cancer Res.*, 12:208, 2010.
Gelmon et al., "Olaparib in patients with recurrent high-grade serous or poorly differentiated ovarian carcinoma or triple-negative breast cancer: a phase 2, multicentre, open-label, non-randomised study," *Lancet Oncol.*, 12:852-861, 2011.
Gibson and Kraus, "New insights into the molecular and cellular functions of poly(ADP-ribose) and PARPs," *Nat. Rev. Mol. Cell Biol.*, 13:411-424, 2012.
Hsu et al., "Definition of PKC-alpha, CDK6, and MET as therapeutic targets in triple-negative breast cancer," *Cancer Res.*, 74:4822-4835, 2014.
International Preliminary Report on Patentability issued in corresponding PCT Application No. PCT/US2015/052966, dated Apr. 13, 2017.
International Search Report and Written Opinion issued in corresponding PCT Application No. PCT/US2015/052966, dated Jan. 29, 2016.
Jagadeeswaran et al., "Activation of HGF/c-Met pathway contributes to the reactive oxygen species generation and motility of small cell lung cancer cells," *Am. J. Physiol. Lung Cell. Mol. Physiol.*, 292:L1488-1494, 2007.
Knight et al., "Met synergizes with p53 loss to induce mammary tumors that possess features of claudin-low breast cancer," *Proc. Natl. Acad. Sci. U. S. A.*, 110:E1301-1310, 2013.
Kummar et al., "Phase 0 clinical trial of the poly (ADP-ribose) polymerase inhibitor ABT-888 in patients with advanced malignancies," *J. Clin. Oncol.*, 27:2705-2711, 2009.
Ledermann et al., "Olaparib maintenance therapy in patients with platinum-sensitive relapsed serous ovarian cancer: a preplanned retrospective analysis of outcomes by BRCA status in a randomised phase 2 trial," *Lancet Oncol.*, 15:852-861, 2014.
Lehmann et al., "Identification of human triple-negative breast cancer subtypes and preclinical models for selection of targeted therapies," *J. Clin. Invest.*, 121:2750-2767, 2011.
Liu et al., "EGFR expression correlates with decreased disease-free survival in triple-negative breast cancer: a retrospective analysis based on a tissue microarray," *Med. Oncol.*, 29:401-405, 2012.
Lord and Ashworth, "Mechanisms of resistance to therapies targeting BRCA-mutant cancers," *Nat. Med.*, 19:1381-1388, 2013.
Luo and Kraus, "On PAR with PARP: cellular stress signaling through poly(ADP-ribose) and PARP-1," *Genes Dev.*, 26:417-432, 2012.
Matsumoto et al., "Binding mode of novel 1-substituted quinzoline derivatives to poly(ADP-ribose) polymerase-catalytic domain, revealed by X-ray crystal structure analysis of complexes," *Biochim. Biophys. Acta.*, 1764:913-919, 2006.
Nowsheen et al., "Synthetic lethal interactions between EGFR and PARP inhibition in human triple negative breast cancer cells," *PLoS ONE*, 7(10):e46614, 2012.
O'Shaughnessy et al., "A randomized phase III study of iniparib (BSI-201) in combination with gemcitabine/carboplatin (G/C) in metastatic triple-negative breast cancer (TNBC)," *J. Clin. Oncol.*, 29:abstr 1007, 2011.
O'Shaughnessy et al., "Iniparib plus chemotherapy in metastatic triple-negative breast cancer," *New Engl. J. Med.*, 364:205-214, 2011.
Rouleau et al., "PARP inhibition: PARP1 and beyond," *Nat. Rev. Cancer*, 10:293-301, 2010.
Ruf et al., "Structure of the catalytic fragment of poly(AD-ribose) polymerase from chicken," *Proc. Natl. Acad. Sci. U. S. A.*, 93:7481-7485, 1996.
Speers et al., "Identification of novel kinase targets for the treatment of estrogen receptor-negative breast cancer," *Clin. Cancer Res.*, 15:6327-6340, 2009.
Trachootham et al., "Targeting cancer cells by ROS-mediated mechanisms: a radical therapeutic approach?" *Nat. Rev. Drug Discov.*, 8:579-591, 2009.
Tutt et al., "Oral poly(ADP-ribose) polymerase inhibitor olaparib in patients with BRCA1 or BRCA2 mutations and advanced breast cancer: a proof-of-concept trial" *Lancet*, 376:235-244, 2010.

(56) References Cited

OTHER PUBLICATIONS

Zagouri et al., "High MET expression is an adverse prognostic factor in patients with triple-negative breast cancer," r. J. Cancer, 108:1100-1105, 2013.

* cited by examiner

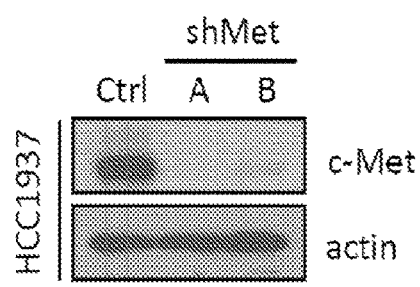
FIG. 2M
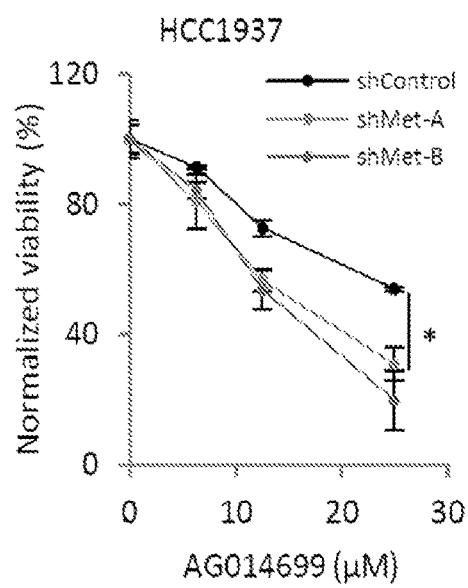
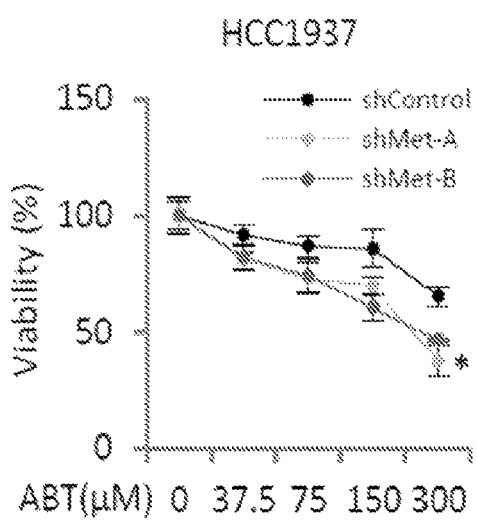
FIG. 2N

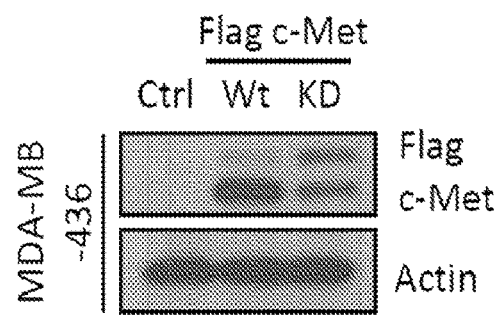
FIG. 2O
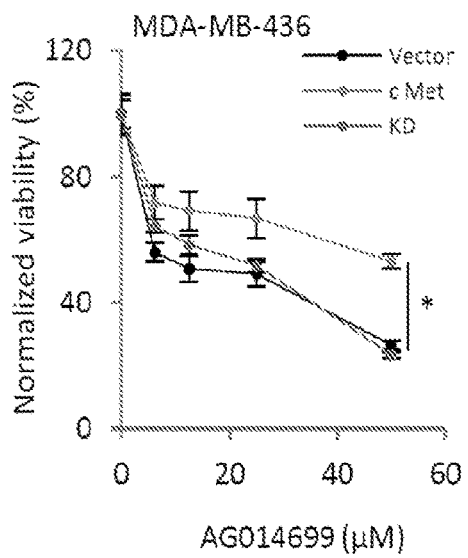
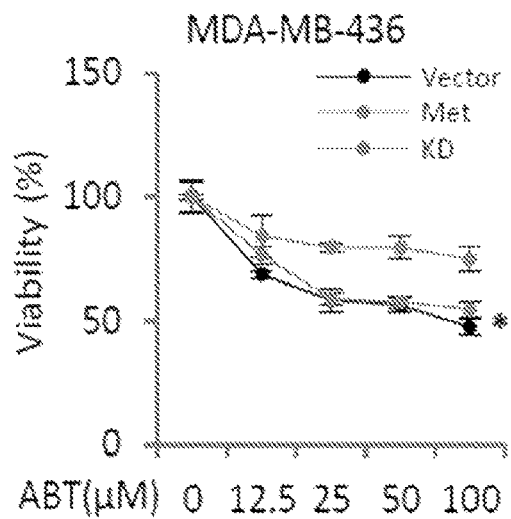
FIG. 2P

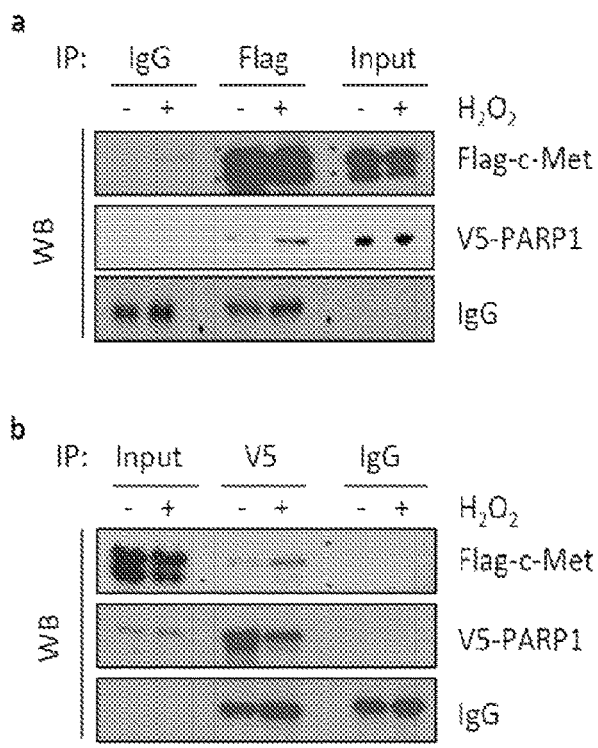
FIGS. 7A-B
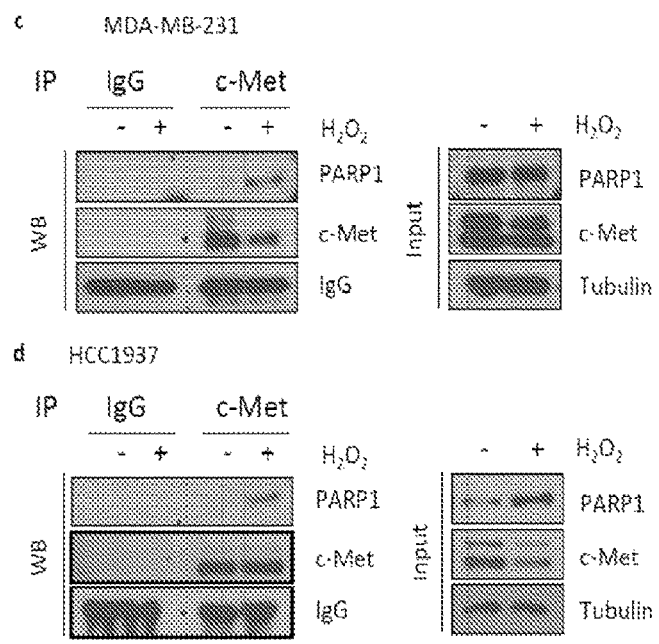
FIGS. 7C-D

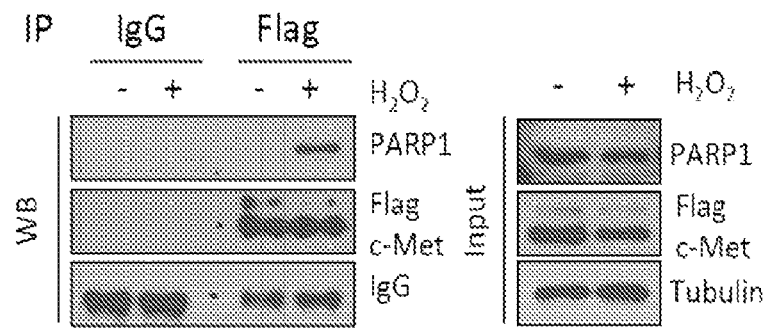
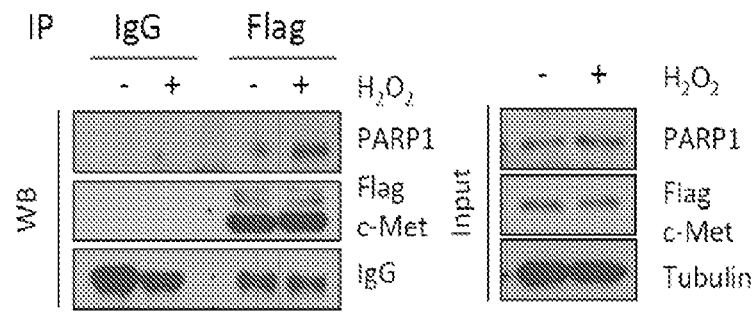
FIGS. 7E-F
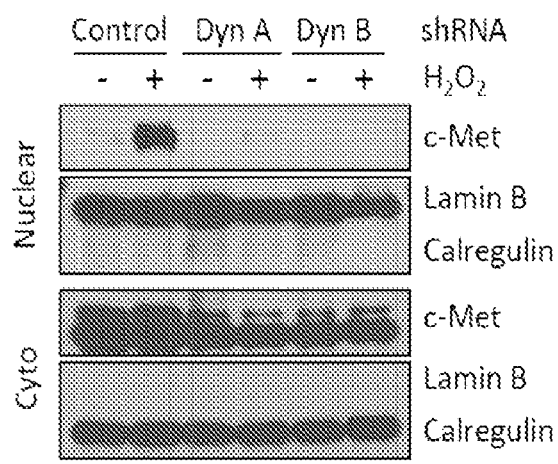
FIG. 7G

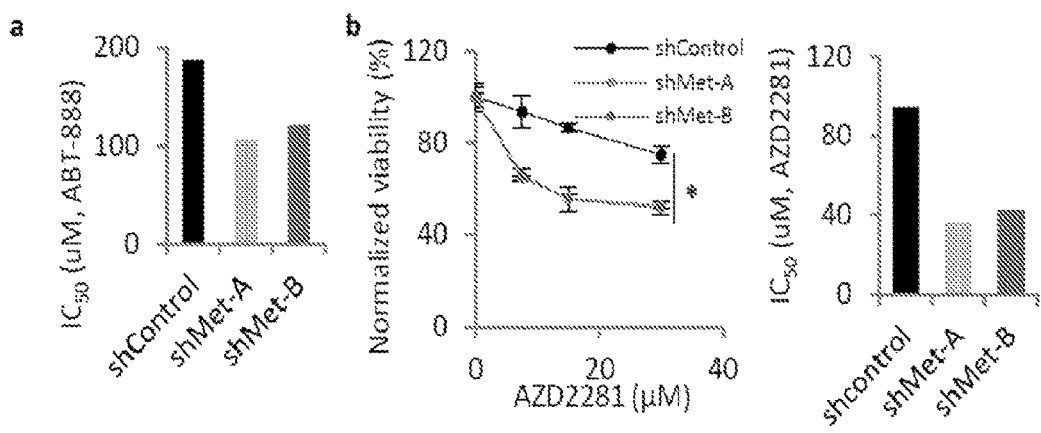
FIGS. 8A-B
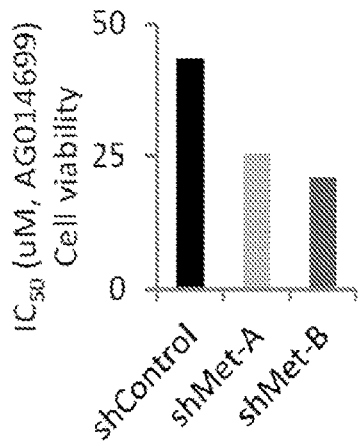
FIG. 8C
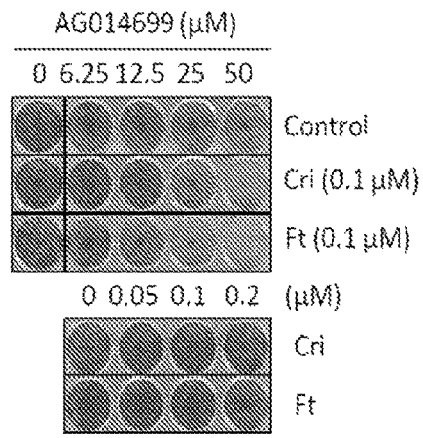
FIG. 8D

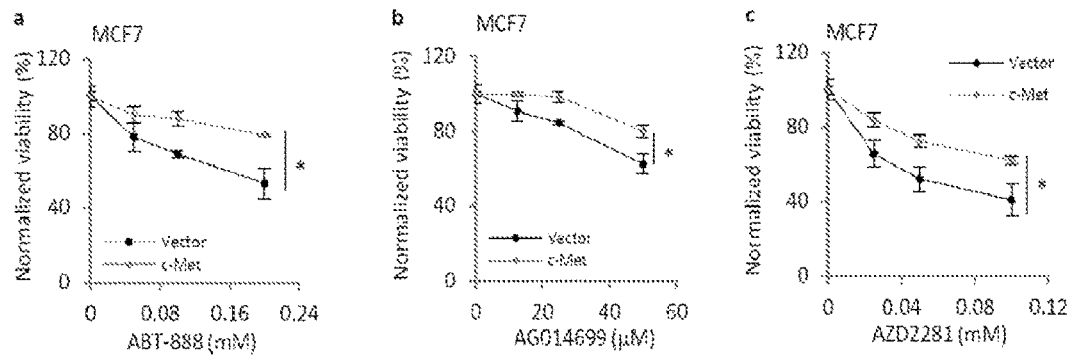
FIGS. 9A-C
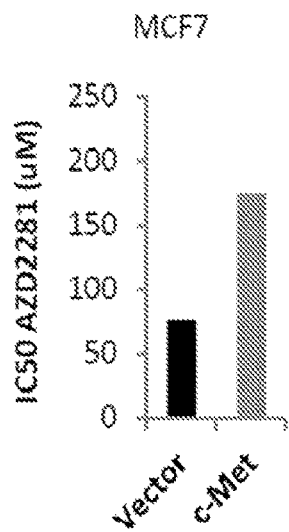
FIG. 9D

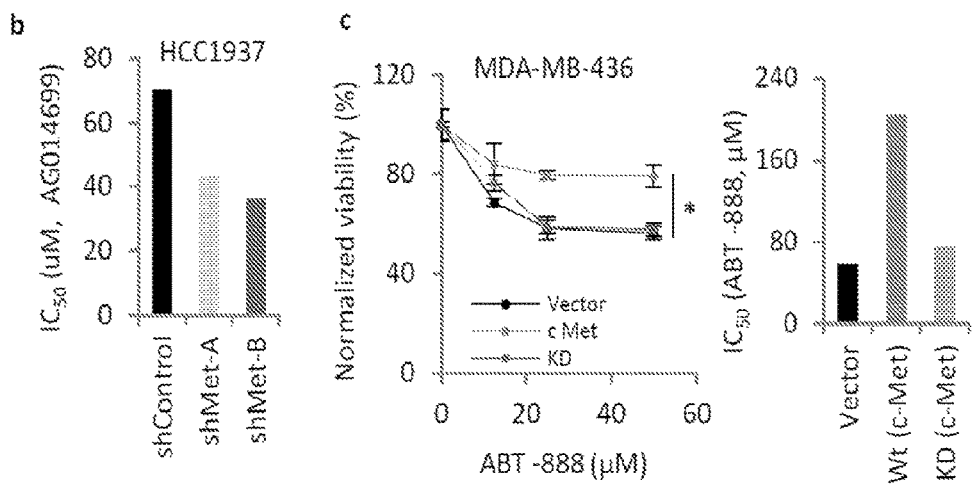
FIGS. 10B-C
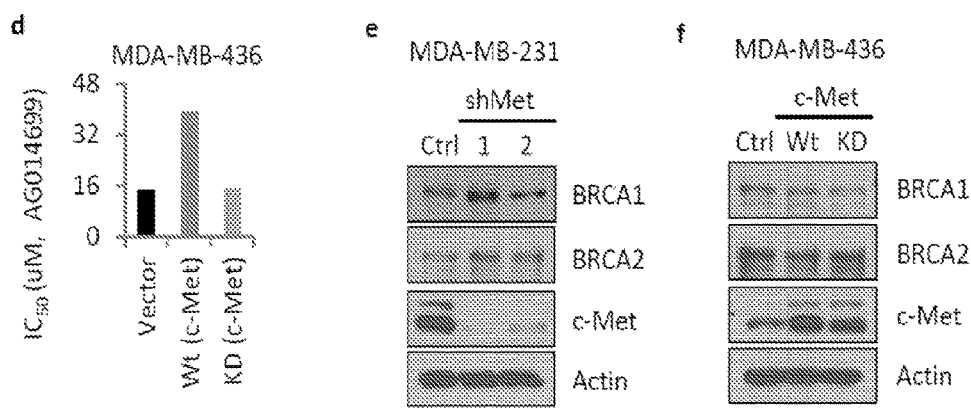
FIGS. 10D-F

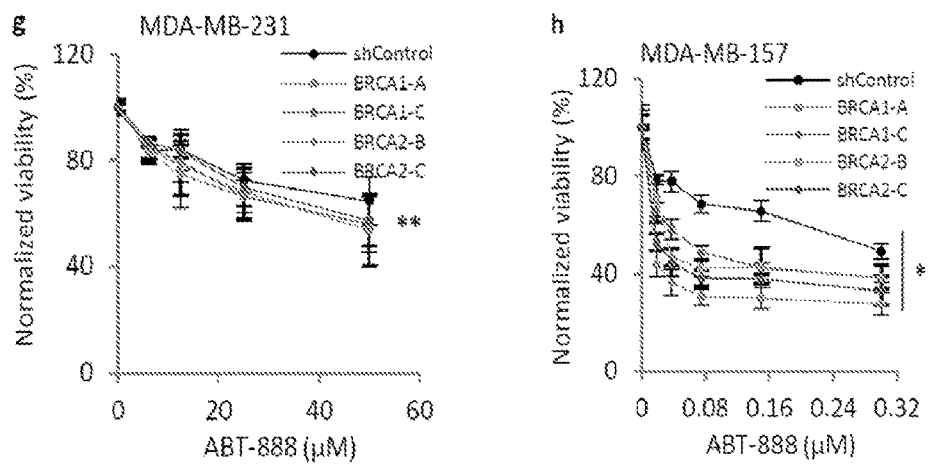
FIGS. 10G-H
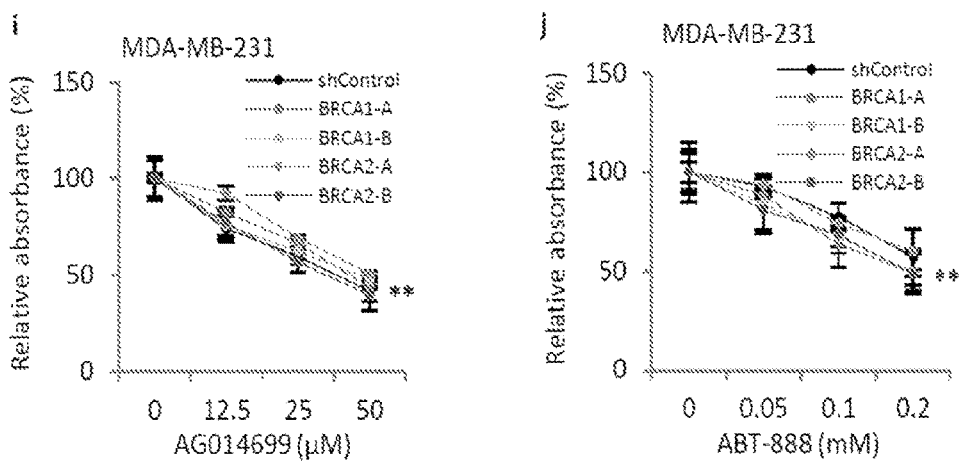
FIGS. 10I-J
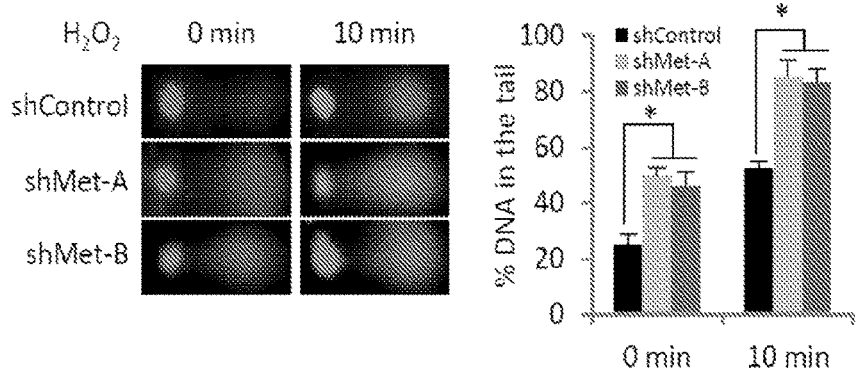
FIG. 11A

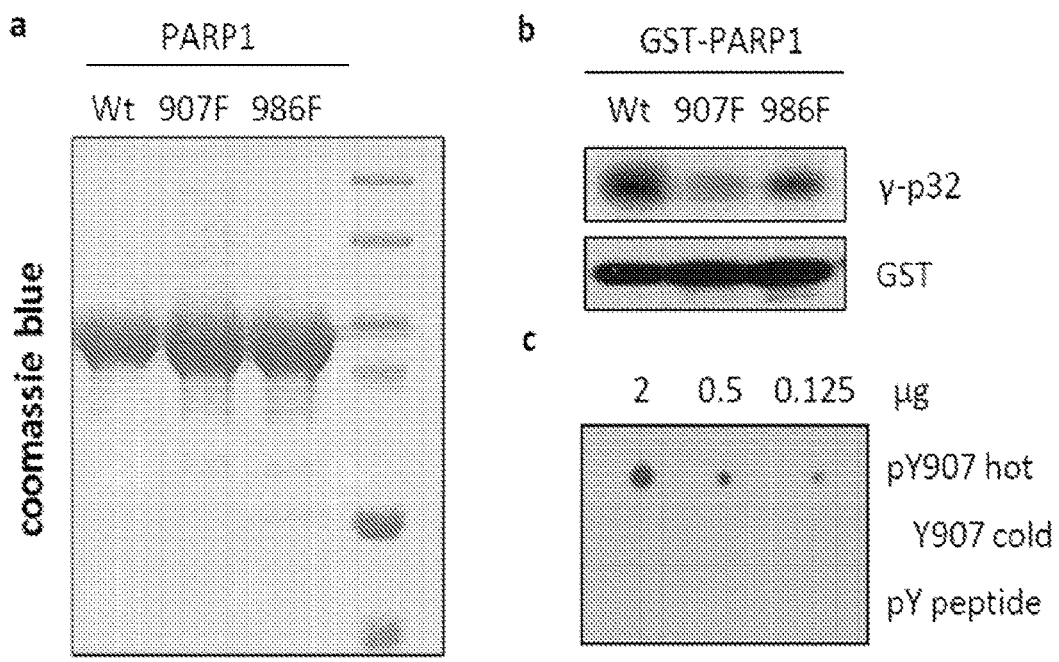
FIGS. 12A-C
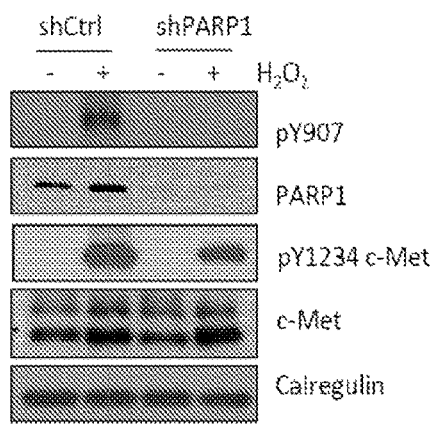
FIG. 12D

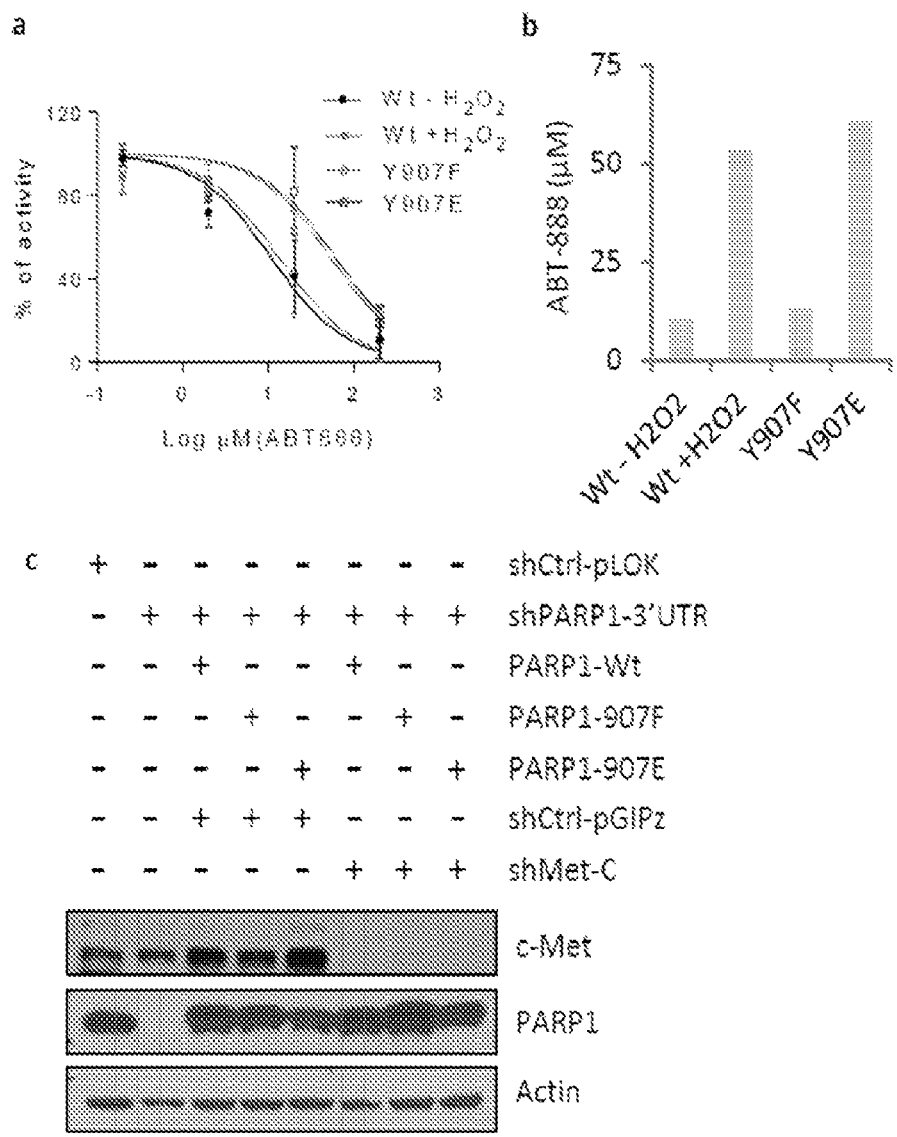
FIGS. 13A-C

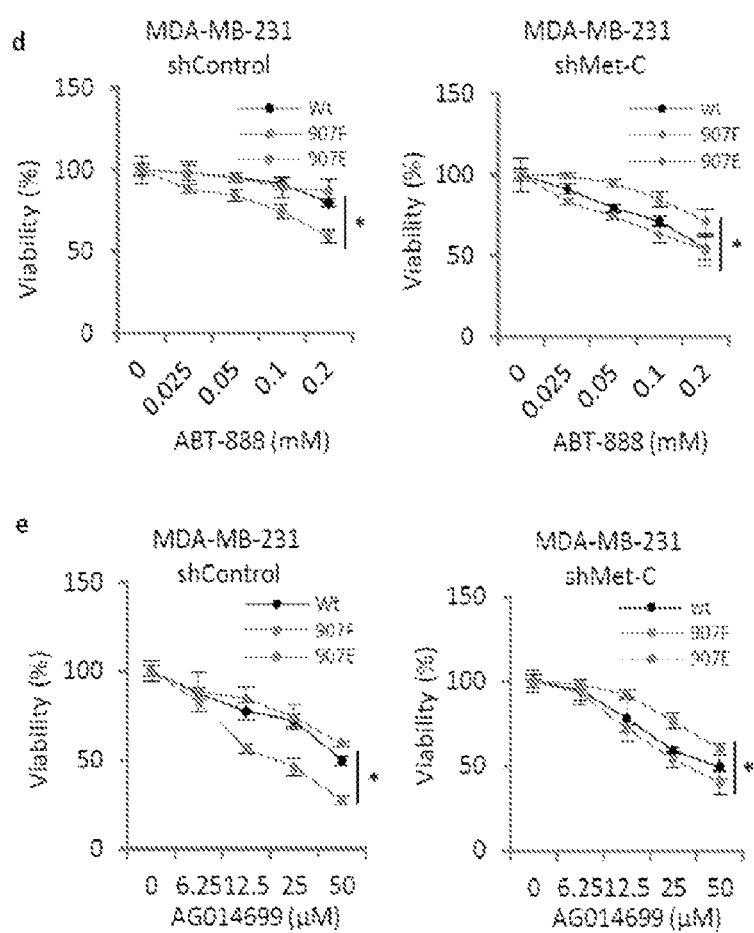
FIGS. 13D-E

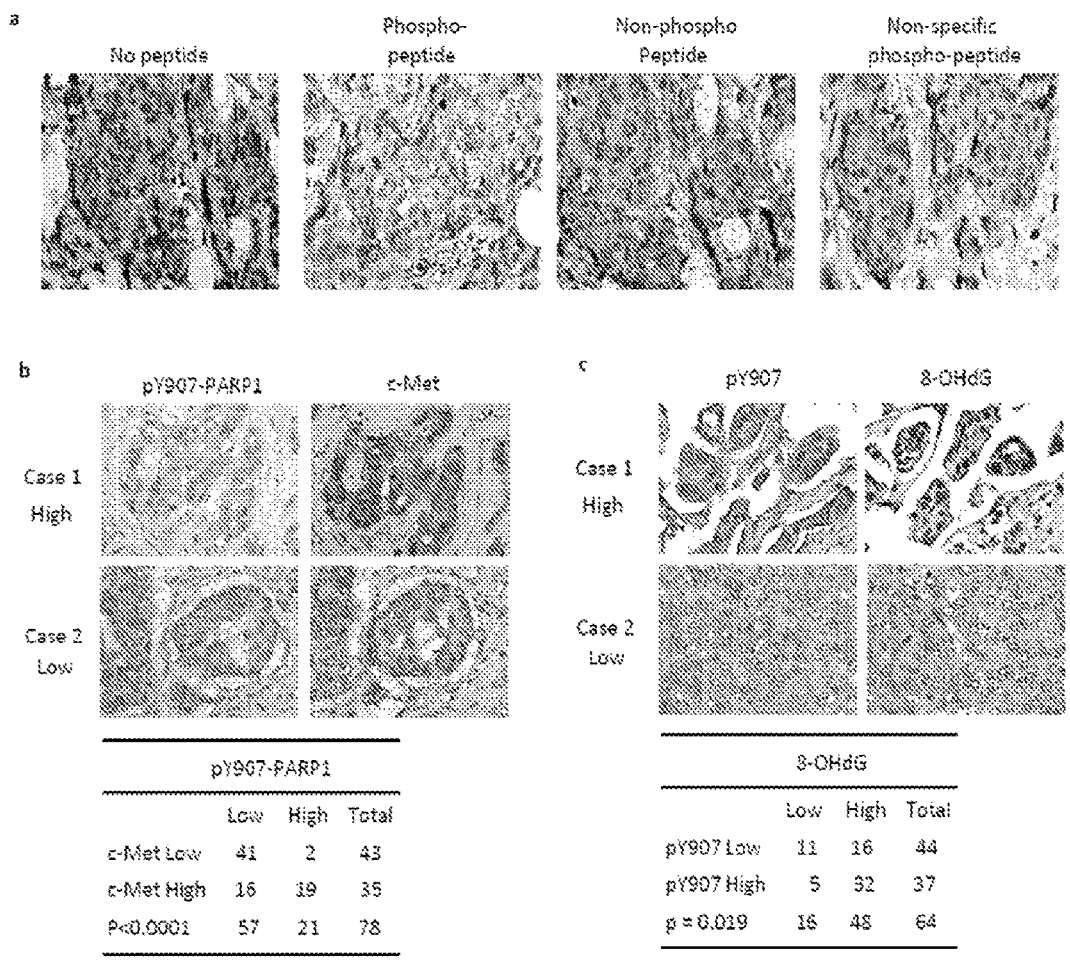
FIGS. 14A-C

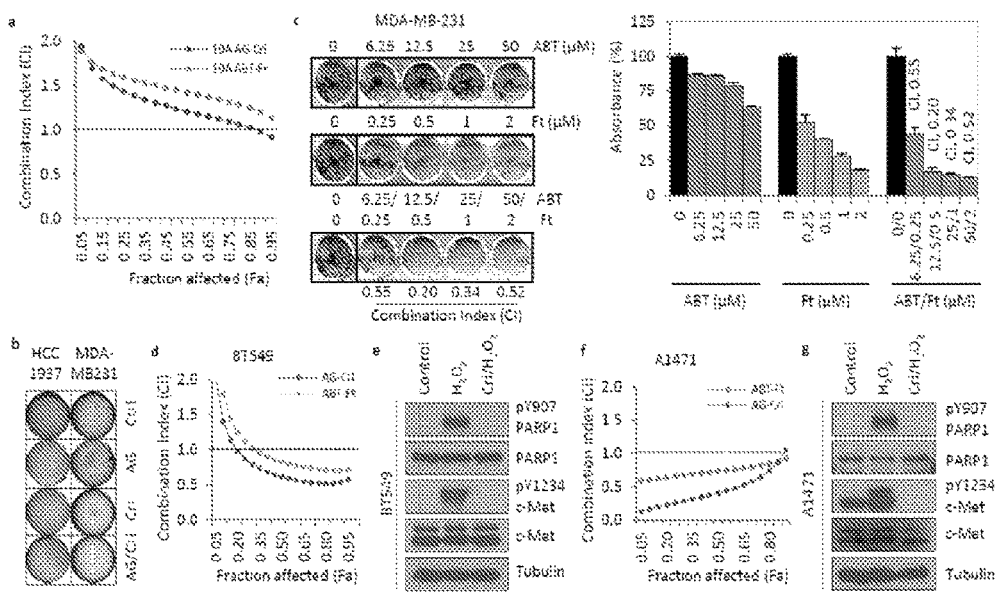
FIGS. 15A-G

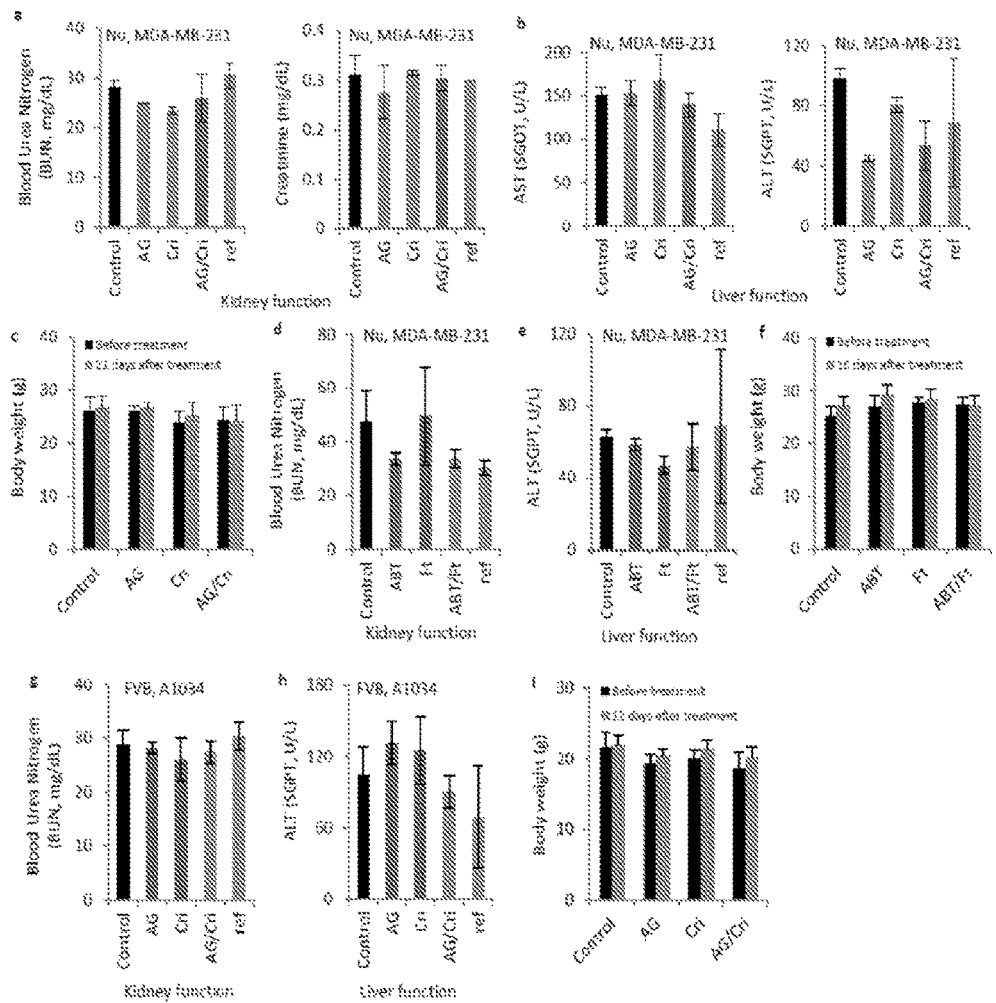
FIGS. 17A-I
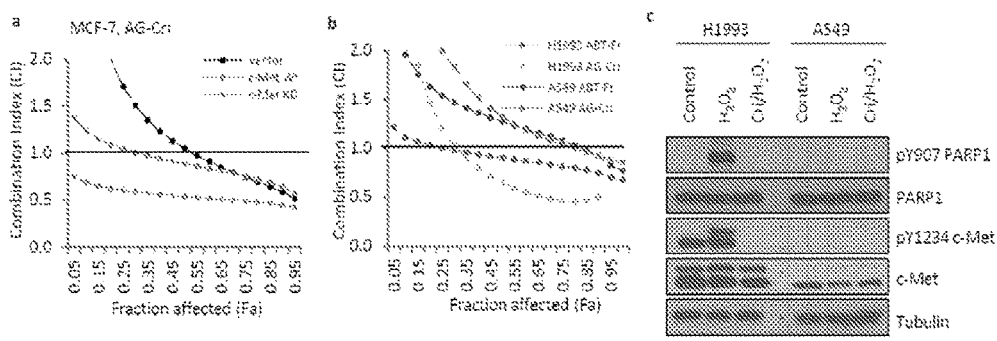
FIGS. 18A-C

PREDICTION OF RESPONSE TO PARP INHIBITORS AND COMBINATIONAL THERAPY TARGETING C-MET AND PARP1

The present application is a national phase application under 35 U.S.C. § 371 of International Application No. PCT/US2015/052966, filed Sep. 29, 2015, which claims the priority benefit of U.S. provisional application No. 62/057,037, filed Sep. 29, 2014, the entire contents of each of which are incorporated herein by reference.

BACKGROUND OF THE INVENTION

1. Field of the Invention

The present invention relates generally to the fields of medicine and oncology. More particularly, it concerns methods for the identification and treatment of PARP inhibitor-resistant cancers.

2. Description of Related Art

Increased levels of reactive oxygen species (ROS) in cancer cells can cause oxidative DNA damage that leads to genomic instability and tumor development (Irani et al., 1997; Trachootham et al., 2009; Radisky et al., 2005; Lindahl, 1993). ROS-induced DNA damage, such as a single-strand breaks, recruits PARP1 to the lesion sites to orchestrate the DNA repair process through poly ADP-ribosylation (PARylation) on itself and its target proteins (Luo and Kraus, 2012; Gibson and Kraus, 2012). PARP inhibitors have been widely evaluated in clinical trials since the discovery of synthetic lethality of PARP inhibition in BRCA-mutant cancer cells, which are deficient in the repair machinery of the double-strand DNA damage (Farmer et al., 2005; Bryant et al., 2005).

In addition, PARP inhibitors are also being investigated in clinical trials for triple-negative breast cancer (TNBC) as it has been reported to possess BRCAness properties (Hampson et al., 2010; Turashvili et al., 2011), such as BRCA mutations, methylations in the BRCA1 promoter, and dysregulation of the BRCA pathway. TNBC is an aggressive subtype of breast cancer that initially responds to chemotherapy, but a majority of TNBCs eventually develop resistance. Moreover, there are no approved targeted therapies to treat TNBC, unlike other breast cancer subtypes, such as those positive for estrogen receptor (ER) and/or HER2, for which specific inhibitors are available. More than 100 clinical trials testing PARP inhibitors are underway, and the U.S. Food and Drug Administration recently approved the PARP inhibitor olaparib (Lynparza™, AstraZeneca) for the treatment of patients with BRCA-mutated ovarian cancer, and there are multiple ongoing clinical trials of this drug targeting different cancer types. While encouraging results were reported in TNBC cancer patients carrying BRCA mutations (Tutt et al., 2010), such results were not observed in another trial (Gelmon et al., 2011). These clinical observations raise an important question of how to increase the response rate in TNBC or other cancer types. Thus, methods for increasing the response rate to PARP inhibitors and identifying the group of patients who will respond to PARP inhibitors are needed to stratify patients during treatment.

SUMMARY OF THE INVENTION

Here, it is shown that receptor tyrosine kinase c-Met associates with and phosphorylates PARP1 at Tyr907, which is essential for DNA repair, and thus c-Met renders cancer cells resistant to PARP inhibition. Combining c-Met and PARP1 inhibitors produced a synergistic effect in vitro and in a breast cancer xenograft tumor model. PARP1 pTyr907 has the potential to serve as a biomarker to predict resistance and stratify patients to maximize the treatment benefit of PARP inhibitors. In addition, a potential therapeutic strategy to increase the PARP inhibitor response rate in TNBC by inhibition of c-Met-mediated phosphorylation of PARP1 at Y907 was identified, thus providing a rationale for a combination therapy for patients with high c-Met expression who do not respond to PARP inhibition.

In a first embodiment, the present invention provides a method of predicting resistance of a cancer in a patient to a PARP1 inhibitor comprising assaying a cancer sample to determine a phosphorylation status of PARP1 Tyr907 in the sample. In some aspects, if PARP1 Tyr907 is phosphorylated, then the cancer may be predicted to be resistant to a PARP1 inhibitor.

In various aspects, the assaying may comprise measuring the level of phosphorylation of PARP1 Tyr907. In certain aspects, assaying may comprise contacting the sample with an antibody that binds specifically to phosphorylated PARP1 Tyr907. In some aspects, assaying may comprise performing a Western blot, ELISA, immunoprecipitation, radioimmunoassay, or immunohistochemical assay.

In some aspects, the method may further comprise identifying the patient as having a cancer that is resistant to a PARP1 inhibitor if PARP1 Tyr907 is phosphorylated. In certain aspects, identifying may comprise reporting whether the patient has a cancer that is resistant to a PARP1 inhibitor. In certain aspects, reporting may comprise preparing a written or oral report. In certain aspects, the method may further comprise reporting to the patient, a doctor, a hospital, or an insurance provider.

In certain aspects, identifying the patient as having a cancer that is resistant to PARP1 inhibitor therapy may further comprise identifying the patient having the cancer as a candidate for treatment with a combination of a PARP1 inhibitor and a MET inhibitor. In some aspects, the PARP1 inhibitor may be olaparib, ABT-888 (Veliparib), BSI-201 (Iniparib), BMN 673, Rucaparib (AG-014699, PF-01367338), AG14361, INO-1001, A-966492, PJ34, or MK-4827. In some aspects, the MET inhibitor may be INCB28060, ARQ197 (tivantinib), AMG458, GSK1363089 (XL880 or foretinib), E7050 (golvatinib), MK-2461, BMS-777607, JNJ-38877605, XL184 (cabozantinib), AMG337, ARQ197, MGCD265, PF04217903 or PF02341066 (crizotinib).

In one embodiment, a method is provided for treating a cancer patient comprising treating a patient determined to have a cancer expressing Tyr907 phosphorylated PARP1 with a therapeutically effective amount of a combination of a PARP1 inhibitor and MET inhibitor. In various aspects, the cancer may be a breast cancer, renal cancer, lung cancer, or ovarian cancer. In certain aspects, the breast cancer may be a triple-negative breast cancer.

In some aspects, the PARP1 inhibitor may be olaparib, ABT-888 (Veliparib), BSI-201 (Iniparib), BMN 673, Rucaparib (AG-014699, PF-01367338), AG14361, INO-1001, A-966492, PJ34, or MK-4827. In some aspects, the MET inhibitor may be INCB28060, ARQ197 (tivantinib), AMG458, GSK1363089 (XL880 or foretinib), E7050 (golvatinib), MK-2461, BMS-777607, JNJ-38877605, XL184 (cabozantinib), AMG337, ARQ197, MGCD265, PF04217903 or PF02341066 (crizotinib).

In some aspects, the PARP1 inhibitor may be administered essentially simultaneously with the MET inhibitor. In certain aspects, the patient may have previously undergone at least one round of anti-cancer therapy. In one aspect, the patient may be a human.

In various aspects, the method may further comprise administering a second anticancer therapy, such as, for example, a surgical therapy, chemotherapy, radiation therapy, cryotherapy, hormonal therapy, toxin therapy, immunotherapy, or cytokine therapy.

In one embodiment, a method is provided for selecting a drug therapy for a cancer patient comprising (a) assaying cancer sample from the patient to determine a phosphorylation status of PARP1 Tyr907 in the sample; and (b) selecting a combination of a PARP1 inhibitor and a MET inhibitor if PARP1 Tyr907 is determined to be phosphorylated.

In one embodiment, a method is provided for sensitizing a cancer to a PARP1 inhibitor-based anticancer therapy comprising administering an effective amount of a MET inhibitor to a patient having the cancer. In some aspects, the method may further comprise administering a PARP1 inhibitor-based anticancer therapy to the subject. In some aspects, the PARP1 inhibitor-based anticancer therapy may be administered essentially simultaneously with said MET inhibitor. In some aspects, the PARP1 inhibitor may be olaparib, ABT-888 (Veliparib), BSI-201 (Iniparib), BMN 673, Rucaparib (AG-014699, PF-01367338), AG14361, INO-1001, A-966492, PJ34, or MK-4827. In some aspects, the MET inhibitor may be INCB28060, ARQ197 (tivantinib), AMG458, GSK1363089 (XL880 or foretinib), E7050 (golvatinib), MK-2461, BMS-777607, JNJ-38877605, XL184 (cabozantinib), AMG337, ARQ197, MGCD265, PF04217903 or PF02341066 (crizotinib).

In one embodiment, a composition is provided comprising a PARP1 inhibitor and a MET inhibitor for use in treating a cancer in a patient. In some aspects, the PARP1 inhibitor may be olaparib, ABT-888 (Veliparib), BSI-201 (Iniparib), BMN 673, Rucaparib (AG-014699, PF-01367338), AG14361, INO-1001, A-966492, PJ34, or MK-4827. In some aspects, the MET inhibitor may be TNCB28060, ARQ197 (tivantinib), AMG458, GSK1363089 (XL880 or foretinib), E7050 (golvatinib), MK-2461, BMS-777607, JNJ-38877605, XL184 (cabozantinib), AMG337, ARQ197, MGCD265, PF04217903 or PF02341066 (crizotinib).

In one embodiment, a composition is provided comprising an antibody that specifically binds to a Tyr907-phosphorylated PARP1 protein. In certain aspects, an antibody specifically binds to a PARP1 polypeptide corresponding to the sequence ADMVSKSANpYCHTSQGD (SEQ ID NO: 1).

In one embodiment, a composition is provided comprising a polypeptide comprising at least eight consecutive amino acids of PARP1 protein fused or conjugated to an immunogen, wherein the at least eight consecutive amino acids of PARP1 protein includes Tyr907 and wherein Tyr907 is phosphorylated. In some aspects, the polypeptide may comprise the sequence ADMVSKSANYCHTSQGD (SEQ ID NO: 1). In various aspects, the immunogen may be keyhole limpet hemocyanin (KLH), bovine serum albumin (BSA), Blue Carrier Protein, *Concholepas concholepas* hemocyanin (CCH), or ovalbumin (OVA).

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Tissue microarray of breast cancer patients was stained with 8-OHdG antibody. Representative images are shown. Correlation analyses were performed by the Pearson chi-square test (P=0.001). (FIG. 1B) Quantitation of breast cancer cells stained with 8-OHdG antibody. Fluorescence intensity was measured by AxioVision software. (FIG. 1C) Breast cancer cells were stained with 8-OHdG antibody and screened by fluorescence microscopy. Fluorescence intensity was measured by AxioVision software. Quantitation shown is mean±SEM. *P<0.05, t-test. (FIG. 1D) Breast cancer cells were used to isolate total DNA and subjected to ELISA assay to measure the 8-OHdG level. (FIG. 1E) Breast cancer cells were incubated with 10 µM of DCF-DA for 30 min. Fluorescence intensity was measured by AxioVision software. Quantitation is shown. (FIG. 1F) Breast cancer cells were incubated with 10 µM of DCF-DA for 30 min. The images were screened by fluorescence microscopy and fluorescence intensity was measured by AxioVision software. Quantitation shown is mean± SEM. *P<0.05, t-test. (FIG. 1G) Breast cancer cell lysates were subjected to Western blot with anti-PAR, PARP1, and tubulin antibodies. Western blot is representative of triplicate experiments. Quantitation is shown on the right. (FIG. 1H) Breast cell lines were subjected to western blot with anti-PAR antibody. Quantitation data shown as mean±SEM. Western blot is representative of triplicated experiments (n=3). *P<0.05, t-test. (FIG. 1I) MDA-MB-231 cells were treated with 20 µM sodium arsenite (As) for 18 h. The association of endogenous PARP1 and c-Met was detected by IP and Western blot. (FIG. 1J) Duolink assay was performed to detect co-localization of PARP1 and c-Met. Bar, 10 m. Representative images are shown. Error bars represent s.d. *P<0.05, t-test. (FIG. 1K) MDA-MB-231 cells were treated with $H_2O_2$ or $H_2O_2$ plus crizotinib pre-treatment. Cytosolic and nucleus fractions were subjected to immunoprecipitation and Western blot analysis with the indicated antibodies. L; long exposure, S; short exposure. Error bars represent s.d. *P<0.05, t-test.

(FIG. 2A) Western blot analysis of c-Met knockdown by two different shRNAs (shMet-A and shMet-B) in MDA-MB-231 cells. (FIG. 2M) Western blot analysis of c-Met knockdown in HCC1937 cells by pGIPz shRNAs. (FIG. 2N) HCC1937 with c-Met knockdown cells were treated with PARP inhibitors (AG014699 and ABT-888) and subjected to cell viability assay. (FIG. 2O) Western blot analysis of wild-type and kinase dead (KD) c-Met expression in MDA-MB-436 cells. (FIG. 2P) c-Met-overexpressing MDA-MB-436 cells were treated with PARP inhibitors (AG014699 and ABT-888) and subjected to cell viability assay. (FIGS. 2Q-R) BRCA1 and BRCA2 knockdown MDA-MB-231 and MDA-MB-157 cells were treated AG014699 and subjected to cell viability assay. Error bars represent s.d. Cri, crizotinib; Ft, foretinib. *P<0.05, **P>0.05, rANOVA.

(FIG. 3A) MDA-MB-231 cells were treated with ABT-888, foretinib, or a combination thereof. γH2AX was detected by immunofluorescence confocal microscopy. Quantitation is shown. (FIG. 3B) c-Met or control knockdown MDA-MB-231 cells as well as c-Met knockdown cells re-expressing wild-type (Wt) or kinase dead (KD) mutant were treated with the indicated drugs for 18 h. γH2AX was detected by immunofluorescence confocal microscopy. Quantitation is shown. (FIG. 3C) HEK293T cells were transfected with V5-PARP1 and Flag-c-Met expression plasmids, and the cells were treated 10 M $H_2O_2$ for 15 min. PARP1 was immunoprecipitated with V5 antibody, followed by Western blot with 4G10 (anti phosphor-tyrosine antibody). (FIG. 3D) Western blot analysis of MDA-MB-231 cells with endogenous PARP1 knocked down by shRNA targeting its 3' UTR and knockdown cells re-expressing PARP1 wild-type or Y907 mutants. (FIG. 3E) Stable cells expressing PARP1 wild-type or Y907 mutants were treated with $H_2O_2$ and incubated with formanidopyrimidine DNA glycosylase (Fpg) prior to a comet assay to evaluate the damaged DNA. DNA in the tail indicated the damaged DNA. Quantitation is shown. (FIG. 3F) Stable cells expressing PARP1 wild-type or Y907 mutants were treated with $H_2O_2$ (20 µM) for 30 min. Poly-ADP ribosylation was detected by the PAR antibody. (FIG. 3G) MDA-MB-231 cells were treated with $H_2O_2$ or $H_2O_2$ plus crizotinib or foretinib pre-treatment. Cell lysates were subjected to Western blot analysis using the indicated antibodies. (FIG. 3H) Re-expression of wild-type or mutant in PARP1 knockdown cells with or without c-Met knockdown were treated with PARP inhibitor AG014699 and subjected to clonogenic formation assay. Representative images and quantitation are shown. (FIG. 3I) Cells with re-expression of wild-type or mutant in PARP1 knockdown cells and with or without c-Met knockdown were treated with 50 µM ABT-888 for 18 h. γH2AX was detected by immunofluorescence confocal microscopy. Quantitation is shown. Error bars represent s.d. *P<0.05, t-test. **P>0.05. ABT, ABT-888; Cri, crizotinib; Ft, foretinib.

(FIG. 4A) Correlation between pY907 of PARP1 and c-Met in TNBC patients and representative images of immunohistochemical staining in tissue microarrays of human breast cancer for PARP1-pY907 and c-Met. Correlation analyses were performed by the Pearson chi-square test (P=0.021). (FIG. 4S) H1993 cells were injected subcutaneously into the right flank of female nude mice Crizotinib (5 mg/kg), AG014699 (5 mg/kg), or the combination was orally administrated 5 days per week for indicated time. Tumor size was measured at the indicated times. Error bars represents, d. Fa, fraction affected. AG, AG014699; ABT, ABT-888; Cri, crizotinib; Ft, foretinib.*P<0.05, t-test.

(FIG. 6A) Cluster analysis of ERBB3, MET and FLT3 mRNA expression from the TCGA breast invasive carcinoma patient cohort. Hierarchical clustering analysis of ERBB3, MET and FLT3 that distinguish TNBC from other human breast tumors (n=1050). Breast cancer patients were categorized by mRNA subtype as non-TNBC patients (n=819) and TNBC patients (n=231) according to expression of ERBB2, ESR1, and PGR (encoding HER2, ER, and PR, respectively). Shown is a box plot generated from original and $\log_2$-transformed mRNA expression levels of TNBC-related kinases in TNBC patients and non-TNBC patients by ESR1, PGR, and ERBB2 mRNA subtyping. (FIG. 6B) Expression of c-Met in breast cancer cell lines. Cell lysates were performed with western blot with indicated antibodies. ***P<0.05, t-test.

FIGS. 7A-G. c-Met associates with PARP1. (FIGS. 7A-B) HEK293T cells were transfected with V5-PARP1 and Flag-c-Met and then treated with 10 μM $H_2O_2$ for 15 min. Immunoprecipitation (IP) and Western blot were performed to detect the association of PARP1 and c-Met. (FIG. 7C) MDA-MB-231 cells were treated with 10 M $H_2O_2$ for 15 min. IP/Western blot were performed to detect the association of PARP1 and c-Met. (FIG. 7D) HCC1937 cells were treated with 10 μM $H_2O_2$ for 15 min. IP/Western blot were performed to detect the association of PARP1 and c-Met. (FIGS. 7E-F) MDA-MB-436 and MCF7 cells were transfected with Flag-c-Met and then treated with 10 μM $H_2O_2$ for 15 min. IP/Western blot were performed to detect the association of PARP1 and c-Met. (FIG. 7G) HeLa cells with shControl and dynein IC knockdown cells were treated with $H_2O_2$. Cells were subjected to cellular fractionation with western blot with indicated antibodies.

FIGS. 8A-M. Downregulation of c-Met sensitizes cells to PARP inhibitors and reduces ROS. (FIG. 8A) $IC_{50}$ of ABT-888 in MDA-MB-231 cells with c-Met knockdown by cell viability assay. (FIG. 8B) c-Met knockdown cells were treated with PARP inhibitor AZD2281 and subjected to cell viability assay. $IC_{50}$ of AZD2281 shown in the right panel. Error bars represent s.d. (FIG. 8C) $IC_{50}$ of AG014699 in MDA-MB-231 cells with c-Met knockdown by cell viability assay. (FIG. 8D) MDA-MB-231 cells were treated with AG014699 and crizotinib or foretinib and subjected to clonogenic cell survival assay. Representative images are shown. (FIGS. 8E-H) c-Met knockdown cells were treated with PARP inhibitor, ABT-888, AG014699, AZD2281 or BAI-201, and subjected to soft agar colony formation assay to determine anchorage-independent cell growth. Representative images and $IC_{50}$ of inhibitors are shown. Error bars represent s.d. (FIG. 8I) MDA-MB-231 and HCC1937 cells were pre-treated with c-Met inhibitor, crizotinib (Cri) or foretinib (Ft), for 2 h. Cells were then treated with 10 μM of DCF-DA for 30 min. DCF level was measured by plate reader with spectra of $495_{EX}$ nm/$529_{EM}$ nm. Error bars represent s.d. (FIG. 8J) c-Met knockdown MDA-MB-231 and HCC1937 cells by pLKO shRNAs were incubated with 10 μM of DCF-DA for 30 min. DCF level was then measured by plate reader with spectra of $495_{EX}$ nm/$529_{EM}$ nm. Error bars represent s.d. (FIGS. 8K-L) c-Met knockdown (3' UTR) MDA-MB-231 cells re-expressing wild-type c-Met or kinase dead c-Met were treated with ABT-888 or AG014699 and subjected to clonogenic cell survival assay. Representative images are shown. Error bars represent s.d. *P<0.05, rANOVA. (FIG. 8M) MDA-MB-231 cells with 3' UTR c-Met knockdown and re-expression of wild type c-Met or kinase dead c-Met were treated with PARP inhibitor (ABT888) and subjected to cell viability assay to determine cell survival. IC50 of knockdown and restoration cells was showing in right of panel. Data shown as mean+s.e.m. and images are representative of triplicate experiments (n=3) (*P<0.05, t-test).

FIGS. 9A-I. Overexpression of c-Met Increases the resistance of cells to PARP inhibitors. (FIGS. 9A-D) c-Met-overexpressing MCF7 cells were treated with PARP inhibitor, ABT-888, AG014699 or AZD2281, and subjected to cell viability assay to evaluate cell growth and $IC_{50}$. (FIGS. 9E-F) c-Met-overexpressing or control MCF7 cells were treated with ABT-888 or AG014699 and subjected to clonogenic cell survival assay. Representative images are shown. Error bars represent s.d. (FIGS. 9G-I) c-Met-overexpressing or control MCF7 cells were treated with ABT-888, AG014699, or BSI-201 and subjected to soft agar colony formation assay to determine anchorage independent cell growth. Representative images are shown. Error bars represent s.d. *P<0.05, rANOVA.

FIGS. 10A-J. c-Met is important for PARP inhibitor response. (FIG. 10A) HCC1937 cells with c-Met knockdown were treated with PARP inhibitor ABT-888 and subjected to cell viability assay. $IC_{50}$ of ABT-888 in HCC1937 cells shows on the right of panel. Error bars represent s.d. (FIG. 10B) $IC_{50}$ of AG014699 in HCC1937 with c-Met knockdown by cell viability assay. (FIG. 10C) MDA-MB-436 cells expressing wild-type c-Met, kinase dead (KD) c-Met, or control vector were treated with ABT-888 and subjected to cell viability assay. $IC_{50}$ of ABT-888 in MDA-MB-436 shows on the right of panel. Error bars represent s.d. (FIG. 10D) $IC_{50}$ of AG014699 in MDA-MB-436 with overexpression of c-Met by cell viability assay. (FIGS. 10E-F) MDA-MB-231 and MDA-MB-436 were knockdown c-Met expression or overexpressed c-Met. Cells were subjected to western blot with indicated antibodies. (FIGS. 10G-H) BRCA1 or BRCA2 knockdown MDA-MB-231 and MDA-MB-157 cells were treated with ABT-888 and subjected to cell viability assay. Error bars represent s.d. (FIGS. 10I-J) BRCA1 or BRCA2 knockdown MDA-MB-231 cells were treated with ABT-888 and subjected to clonogenic cell survival assay. Error bars represent s.d. *P<0.05, **P>0.05, rANOVA.

FIGS. 11A-F. c-Met is involved in DNA damage response. (FIG. 11A) c-Met knockdown and control MDA-MB-231 cells were treated with $H_2O_2$ for the indicated time and incubated with formanidopyrimidine DNA glycosylase (Fpg). DNA damage was assessed by comet assay. Representative images are shown. Quantification of the levels of DNA damage is shown on the right. (FIG. 11B) c-Met knockdown and control MDA-MB-231 cells were treated with $H_2O_2$ and Hu/Arac to induce and allow DNA damage to accumulate. Hu/Arac and $H_2O_2$ were replaced by fresh media and incubated for the indicated time. Damaged DNA was assessed by comet assay. Quantification of the levels of DNA damage is shown. (FIG. 11C) Luciferase plasmid treated with $H_2O_2$ transfected into c-Met knockdown MDA-MB-231 cells, 24 h later, luciferase activity was measured. Data shown as mean±SEM of triplicated experiments (n=3) (*P<0.05, t-test). (FIG. 11D) Western blot analysis of c-Met wild-type (Wt) and kinase dead mutant (KD) expression. (FIG. 11E) c-Met-overexpressing and control MCF7 cells were treated with $H_2O_2$ for the indicated time. Quantitation of the damaged DNA by comet assay is shown. (FIG. 11F) c-Met overexpressing MCF7 cells were treated with $H_2O_2$ or pretreated with crizotinib for 15 min. DNA damage was assessed by comet assay. Quantification of the levels of DNA damage is shown. Error bars represent s.d. *P<0.05, t-test.

FIGS. 12A-F. c-Met mediates phosphorylation of PARP1 at Y907. (FIG. 12A) Coomassie blue staining of GST fusion PARP1 wild-type and PARP1 Y907F and Y986F mutants. (FIG. 12B) GST fusion wild-type PARP1 and PARP1 Y907F and Y986F mutants were incubated with [$\gamma$-$^{32}$P]-ATP and purified c-Met. Radiolabeled ATP in PARP1 was visualized by autoradiography. Total GST was visualized by Western blot. (FIG. 12C) Dot blot assay was used to evaluate the specific antibody against phosphorylated Y907 (pY907) of PARP1. (FIG. 12D) Characterization of anti-pY907-PARP1 antibody in PARP1 knockdown MDA-MB-231 cells by Western blot analysis. The antibody was also characterized by confocal microscopy. (FIG. 12E) PARP1 knockdown MDA-MB-231 cells re-expressing wild-type or Y907F PARP1 were treated with $H_2O_2$ for 30 min and subjected to Western blot analysis. (FIG. 12F) MDA-MB-231 cells were knocked down the expression of c-Met and treated with $H_2O_2$ for 30 min and subjected to Western blot analysis with indicated antibodies.

FIGS. 13A-E. c-Met-mediated phosphorylation of PARP1 at Y907 regulates PARP inhibitor response. (FIG. 13A) PARP1 knockdown MDA-MB-231 cells re-expressing wild-type, Y907F, or Y907E PARP1 were treated with $H_2O_2$ (20 μM) for 30 min. Cell lysates were subjected to PARP enzyme activity assay. Data shown as mean±SEM of triplicated experiments (n=3). *P<0.05, t-test. (FIG. 13B) $IC_{50}$ of ABT-888 between wild-type and mutant Y907 PARP by PARP enzyme activity assay. (FIG. 13C) Western blot analysis of c-Met knockdown MDA-MB-231 cells re-expressing wild-type or mutant PARP1. (FIGS. 13D-E) Control and c-Met knockdown cells from (FIG. 13C) were treated with PARP inhibitor (ABT-888 or AG014699) and subjected to cell viability assay. Error bars represent s.d. *P<0.05, rANOVA.

FIGS. 14A-C. Clinical correlation of pY907 in human breast cancer tumor tissues. (FIG. 14A) Peptide competition assay was carried out to characterize pY907-PARP1 antibody by IHC staining of breast cancer patient tumor tissues. (FIG. 14B) Correlation analysis between c-Met and pY907-PARP1 in non-TNBC tissue microarray. P<0.05, Pearson chi-square test. (FIG. 14C) Correlation analysis between 8-OHdG and pY907-PARP1 in TNBC tissue microarray. Correlation analyses were performed by the Pearson chi-square test (P=0.019). Representative staining image of positive and negative cases are shown for (FIG. 14B) and (FIG. 14C).

FIGS. 15A-G. Synergistic effect of combination treatment of PARP and c-Met inhibitors in c-Met expression breast cancer cell lines. (FIG. 15A) MCF10A cells were treated with combinations of PARP and c-Met inhibitors. Synergistic effects were determined by calculating the combination index (CI) based on the Chou-Talalay method. (FIG. 15B) Synergistic effect of c-Met inhibitor crizotinib (Cri) and PARP inhibitor AG014699 (AG) was measured by soft agar assay in MBA-MD-231 cells and HCC1937 cells. Representative images are shown. (FIG. 15C) MBA-MD-231 cells were treated with c-Met inhibitor foretinib and PARP inhibitor ABT-888. Clonogenic cell survival assay was used to measure cell growth. CI values of Ft and ABT combination was determined by Chou-Talalay method. Representative images and quantitation are shown. Error bars represent s.d. (FIG. 15D-F) A1471 and BT549 cells were treated with of PARP and c-Met inhibitors and synergistic effect of the combination treatment was measured by cell viability assay. (FIG. 15E-G) A1471 and BT549 cells were treated with $H_2O_2$ or pre-crizotinib treatment plus $H_2O_2$, and cell lysates were subjected to Western blot analysis with the indicated antibodies. Error bars represent s.d. ABT, ABT-888, Ft, foretinib, AG, AG014699, Cri, Crizotinib.

(FIG. 16A) A1034 cells were injected into the mammary fat pad of nude mice. Crizotinib (5 mg/kg), AG014699 (5 mg/kg), or the combination was orally administrated 5 days per week for indicated time. Tumor size was measured at the indicated times. (FIG. 16B) HCC1937 cells were injected into the mammary fat pad of nude mice. Crizotinib (5 mg/kg), AG014699 (5 mg/kg), or the combination was orally administrated 5 days per week for indicated time. Tumor size was measured at the indicated times. Error bars represent s.d. *P<0.05, t-test.

FIGS. 17A-I: Clinical chemistry and body weight analysis of combined inhibition of e-Met and PARP1 in mice. (FIGS. 17A-B) The effect of treatment of AG014699 and Crizotinib on kidney function and on liver function of nude mice with MDA-MB-231 xenograft tumor. (FIG. 17C) The body weight of nude mice before and after treatment of AG014699 and Crizotinib. (FIGS. 17D-E) The effect of treatment of ABT-888 and foretinib on kidney function and on liver function of nude mice with MDA-MB-231 xenograft tumors. (FIG. 17F) The body weight of nude mice before and after treatment of ABT-888 and foretinib. (FIGS. 17G-H) The effect of treatment of AG014699 and Crizotinib on kidney function and on liver function of FVB mice with A1034 syngeneic mouse tumors. (FIG. 17I) The body weight of FVB mice before and after treatment of AG014699 and Crizotinib. AST, aspartate aminotransferase. ALT, alanine transaminase. AG, AG014699, Cri, Crizotinib, ABT, ABT-888, Ft, foretinib, AST, aspartate aminotransferase. ALT, alanine transaminase. Error bars represent s.d.

FIGS. 18A-C. Synergistic effect of combination treatment of PARP and c-Met inhibitors in c-Met ectopic expression breast cancer and NSCLC cell lines. (FIG. 18A) MCF-7 cells with ectopic expression of c-Met were treated with combinations of PARP and c-Met inhibitors. Synergistic effects were determined by calculating the combination index (CI) based on the Chou-Talalay method. (FIG. 18B) Lung cancer cell lines, H1993 and A549, were treated with of PARP and c-Met inhibitors and synergistic effect of the combination treatment was measured by cell viability assay. (FIG. 18C) H1993 and A549 cells were treated with $H_2O_2$ or pro-crizotinib treatment plus $H_2O_2$, and cell lysates were subjected to Western blot analysis with the indicated antibodies. ABT, ABT-888, Ft, foretinib, AG, AG014699, Cri, Crizotinib.

DESCRIPTION OF ILLUSTRATIVE EMBODIMENTS

Figure 1A:
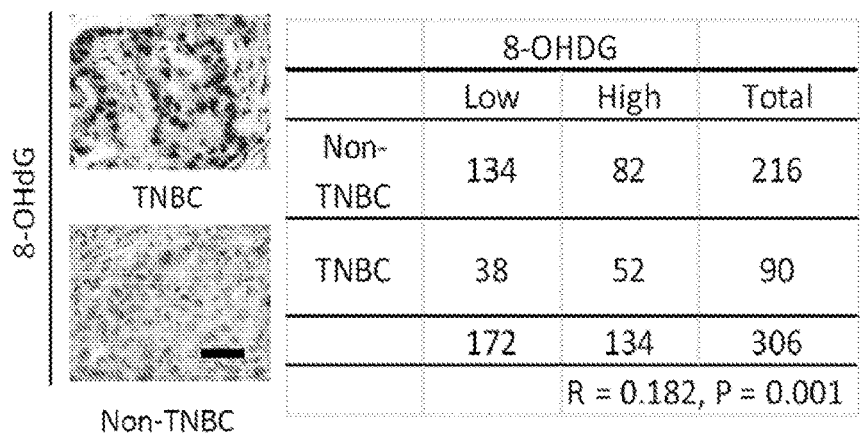
FIGS. 1A-K. ROS induces association of c-Met and PARP1.

Triple-negative breast cancer (TNBC) is a highly aggressive subtype of breast cancer that lacks expression of estrogen receptor (ER), progesterone receptor (PR), and overexpression or amplification of HER2 (Carey et al., 2010). Although some TNBC patients initially respond to chemotherapy, a majority of them eventually develop resistance (Liedtke et al., 2008). Currently, there are no effective targeted therapies against TNBC. Recently, poly (ADP-ribose) polymerase (PARP) inhibitors have emerged as promising therapeutics for patients with TNBC (Anders et al., 2010; Rouleau et al., 2010). A phase 2 study reported improved clinical benefits when the PARP inhibitor, iniparib, was combined with chemotherapy (O'Shaughnessy et al., 2011); however, a subsequent phase 3 study indicated it did not provide significant overall survival or progression free survival benefit (O'Shaughnessy et al., 2011) and resistance and low response rate were observed (Lord and Ashworth, 2013). Thus, it is urgent to identify potential biomarkers to stratify patients to increase the response rate of PARP inhibitor treatment. Here, it is shown that receptor tyrosine kinase c-Met associates with and phosphorylates PARP1 at Tyr907 (Y907), which is essential for DNA repair, rendering TNBC cells resistant to PARP inhibition. The combination of c-Met and PARP1 inhibitors produced synergistic effect in vitro and in a breast cancer xenograft tumor model. The present study identifies a biomarker (pY907, PARP1) that can potentially predict resistance and stratify patients to maximize the treatment benefit of PARP inhibitors and a rational combination therapy for patients with high c-Met expression who do not respond to PARP inhibition. The combination of PARP and c-Met inhibitors may serve as a promising therapy strategy to treat TNBC. In addition to breast cancer, these findings may also open new avenues of research on PARP inhibition in other cancer types.

I. ASPECTS OF THE PRESENT INVENTION

With chemotherapy and radiation therapy as current treatment strategies for treating TNBC, 50% of patients initially respond to first-line therapy, and early-stage responders have good prognosis. However, the other 50% of patients, who have residual disease following front line therapy, have poor prognosis and leads to worse outcomes. The lack of specific targeted therapy for this type of more aggressive and higher grade breast cancer is a major challenge in the clinic. Interestingly, even though the FDA recently approved olaparib for the treatment of patients with BRCA-mutated ovarian cancer, some patients with wild-type BRCA have also demonstrated response to this inhibitor (Tutt et al., 2010; Gelmon et al., 2011; Ledermann et al., 2014), suggesting that other mechanisms may regulate PARP inhibitor response. Therefore, it is imperative to understand the characteristics of TNBC and develop mechanism-driven target therapy that will benefit TNBC patients. Here, a mechanism by which c-Met phosphorylates PARP1 at Y907 and regulates both the activity of PARP1 and response to PARP inhibition is revealed (FIGS. 18A-C). The combination of c-Met and PARP inhibition synergistically inhibits in vitro cell growth and in vivo tumor growth. Notably, pY907-PARP has the potential to serve as a biomarker to predict resistance to PARP inhibitors and stratify patients for maximal benefit from PARP inhibition.

Figure 4A:
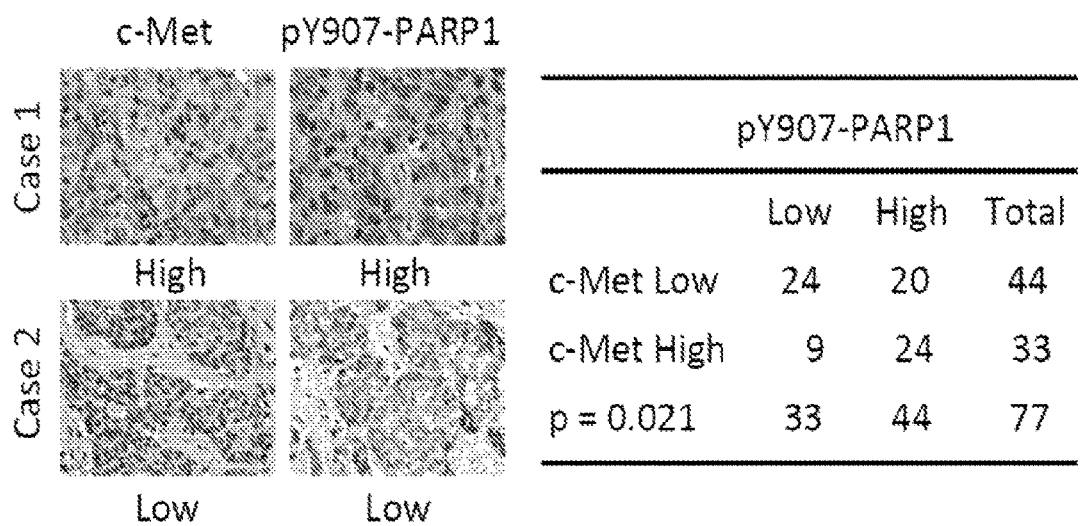
FIGS. 4A-S. Clinical relevance and potential therapeutic strategy targeting PARP1 and e-Met in TNBC.

Of note, clinical studies have indicated that about half of TNBC patients overexpress c-Met (Zagouri et al., 2013; Castaldi et al., 2010). Interestingly, a positive correlation between c-Met and pY907-PARP expression was observed not only in TNBC but also non-TNBC (FIG. 4A). As PARP inhibitors are currently used for TNBC in clinical trials, this breast cancer subtype was focused on. About one-third (24/77 in FIG. 4A) of TNBC patients positive for pY907/c-Met positive would likely be resistant to PARP inhibitor alone and could benefit from the combined therapy of c-Met and PARP inhibition using pY907/c-Met as biomarkers.

PARP inhibitors are broadly used in clinical trials for other cancer types more than they are used for TNBC, and c-Met is a proto-oncogene overexpressed in multiple cancer types (Baccaccio and Comoglio, 2006). The positive correlation between c-Met and pY907 observed in non-TNBC (FIG. 14B) and results from ectopic expression of c-Met in MCF-7 cells (FIGS. 4P-R and FIG. 18A) or NSCLC (FIG. 4S and FIGS. 18B-C) suggests that patients of other types of cancer with overexpression of c-Met in their tumors may also benefit from this combination therapy.

II. METHODS OF TREATING

Certain aspects of the present invention can be used to identify and/or treat a disease or disorder based on the phosphorylation state of Tyr907 of PARP1. Other aspects of the present invention provide for sensitizing a subject with cancer to treatment with PARP inhibitors.

The term "subject" or "patient" as used herein refers to any individual to which the subject methods are performed. Generally the patient is human, although as will be appreciated by those in the art, the patient may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of patient.

"Treatment" and "treating" refer to administration or application of a therapeutic agent to a subject or performance of a procedure or modality on a subject for the purpose of obtaining a therapeutic benefit of a disease or health-related condition. For example, a treatment may include administration chemotherapy, immunotherapy, radiotherapy, performance of surgery, or any combination thereof.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the invasiveness of a tumor, reduction in the growth rate of the cancer, or prevention of metastasis. Treatment of cancer may also refer to prolonging survival of a subject with cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect. A tissue, tumor, or cell can be contacted with one or more compositions or pharmacological formulation(s) comprising one or more of the agents, or by contacting the tissue, tumor, and/or cell with two or more distinct compositions or formulations.

Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

The methods described herein are useful in treating cancer. Generally, the terms "cancer" and "cancerous" refer to or describe the physiological condition in mammals that is typically characterized by unregulated cell growth. More specifically, cancers that are treated using any one or more PARP inhibitors, or variants thereof, and in connection with the methods provided herein include, but are not limited to, solid tumors, metastatic cancers, or non-metastatic cancers. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, pancreas, prostate, skin, stomach, testis, tongue, or uterus.

The cancer may specifically be of the following histological type, though it is not limited to these: neoplasm, malignant; carcinoma; lymphoma; blastoma; sarcoma; carcinoma, undifferentiated; giant and spindle cell carcinoma; small cell carcinoma; small cell lung cancer, non-small cell lung cancer; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; lentigo maligna melanoma; acral lentiginous melanoma; nodular melanoma; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; ostoosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; B-cell lymphoma; malignant lymphoma; Hodgkin's disease; Hodgkin's; low grade/follicular non-Hodgkin's lymphoma; paragranuloma; malignant lymphoma, small lymphocytic; malignant lymphoma, large cell, diffuse; malignant lymphoma, follicular, mycosis fungoides; mantle cell lymphoma; Waldenstrom's macroglobulinemia; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; chronic lymphocytic leukemia (CLL); acute lymphoblastic leukemia (ALL); Hairy cell leukemia; chronic myeloblastic leukemia; and hairy cell leukemia.

An effective response of a patient or a patient's "responsiveness" to treatment refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse. For example, an effective response can be reduced tumor size or progression-free survival in a patient diagnosed with cancer.

Poly(ADP-ribose) polymerase 1 has an essential role in facilitating DNA repair, controlling RNA transcription, mediating cell death, and regulating immune response. PARP1 inhibitors are a group of pharmacological inhibitors of the enzyme PARP1 (see NP_001609.2, which is incorporated herein by reference). In various preclinical cancer models and human clinical trials, PARP1 inhibitors have been shown to potentiate radiation and chemotherapy by increasing apoptosis of cancer cells, limiting tumor growth, decreasing metastasis, and prolonging the survival of tumor-bearing subjects (WO 2007/084532; Donawho et al., 2007; Kummar et al., 2009). By way of example, PARP1 inhibitors include, but are not limited to, olaparib (AZD-2281), veliparib (ABT-888), iniparib (BSI-201), rucaparib (AG014699, PF-01367338), AG14361, INO-1001, A-966492, PJ34, MK-4827, CEP 9722, BNM-673, 3-aminobenzamide, and those disclosed in U.S. Pat. Nos. 7,928,105; 8,124,606; 8,236,802; 8,450,323; WO 2006/110816; WO 2008/083027; and WO 2011/014681.

Dysregulated c-Met receptor tyrosine kinase pathways play roles in tumor formation, growth, maintenance and progression (Birchmeier et al., 2003; Boccaccio et al., 2006; Christensen et al., 2005). c-Met is overexpressed in a significant portions of human cancers, and is often associated with poor clinical outcomes such as more aggressive disease, disease progression, tumor metastasis and shortened patient survival. c-Met inhibitors are a group of pharmacological inhibitors of the receptor tyrosine kinase c-Met. c-Met receptor tyrosine kinase inhibitors include, but are not limited to, INCB28060 (WO2008/064157), ARQ197 (tivantinib), AMG458, GSK1363089 (XL880 or foretinib), E7050 (golvatinib), MK-2461, BMS-777607, JNJ-38877605, XL184 (cabozantinib), AMG337, ARQ197, MGCD265, PF04217903 and PF02341066 (crizotinib).

Regarding neoplastic condition treatment, depending on the stage of the neoplastic condition, neoplastic condition treatment involves one or a combination of the following therapies: surgery to remove the neoplastic tissue, radiation therapy, and chemotherapy. Other therapeutic regimens may be combined with the administration of the anticancer agents, e.g., therapeutic compositions and chemotherapeutic agents. For example, the patient to be treated with such anti-cancer agents may also receive radiation therapy and/or may undergo surgery.

For the prevention or treatment of disease, the appropriate dosage of a therapeutic composition, e.g., a PARP inhibitor or c-MET inhibitor, will depend on the type of disease to be treated, as defined above, the severity and course of the disease, whether the agent is administered for preventive or therapeutic purposes, previous therapy, the patient's clinical history and response to the agent, and the discretion of the physician. The agent is suitably administered to the patient at one time or over a series of treatments.

A. Combination Treatments

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. A tissue, tumor, or cell can be contacted with one or more compositions or pharmacological formulation(s) comprising one or more of the agents or by contacting the tissue, tumor, and/or cell with two or more distinct compositions or formulations. Also, it is contemplated that such a combination therapy can be used in conjunction with radiotherapy, surgical therapy, or immunotherapy.

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few h apart, or a few days apart.

An anti-cancer first treatment may be administered before, during, after, or in various combinations relative to a second anti-cancer treatment. The administrations may be in intervals ranging from concurrently to minutes to days to weeks. In embodiments where the first treatment is provided to a patient separately from the second treatment, one would generally ensure that a significant period of time did not expire between the time of each delivery, such that the two compounds would still be able to exert an advantageously combined effect on the patient. In such instances, it is contemplated that one may provide a patient with the first therapy and the second therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a PARP inhibitor and/or c-MET inhibitor is "A" and another anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclophosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan);

bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, autrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin; procarbazine; plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the invention. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include CD20, carcinoembryonic antigen, tyrosinase ($p^{97}$), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis*, *Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Chemicals and Antibodies.

Hydrogen peroxide (#216763), cycloheximide (#C4859) and sodium arsenite solution (#35000) were obtained from Sigma-Aldrich (St. Louis, Mo.). Antibodies detecting tubulin (#T5168), flag (#F3165) and actin (#A2066) were also from Sigma-Aldrich (St. Louis, Mo.). Antibodies detecting γH2AX (#05-636) and anti-phosphotyrosine (#05-321, 4G10) were from EMD Millipore (Billerica, Mass.). Antibodies detecting GST fusion protein (#sc-53909), HA-tag (#sc-805) and PARP1 (#sc-7150) for western blot were obtained from Santa Cruz Biotechnology (Santa Cruz, Calif.). Antibodies against PARP1 (#9532) for immunoprecipitation (IP) and for detecting c-Met (#8198) and phosphorylated c-Met (#3077) were from Cell Signaling Technology (Danvers, Mass.). Antibody against 8-Hydroxy-2'-Deoxy Guanosine (8-OHdG) was obtained from Genox Corporation (Baltimore, Md.). All fluorescence-labeled secondary antibodies were obtained from Invitrogen (Carlsbad, Calif.). The mouse anti-phospho-PARP1 Y907 antibody was generated against a phosphorylated synthetic peptide (AD-MVSKSAN-Yp-CHTSQGD; SEQ ID NO: 1) at China Medical University, Center of Molecular Medicine. The horseradish peroxidase (HRP) conjugated secondary antibodies for western blotting were obtained from eBioscience (San Diego, Calif.). c-Met kinase inhibitors: crizotinib (#C-7900) and foretinib (#F-4185) from LC Laboratories (Woburn, Mass.). PARP inhibitors ABT-888 (Veliparib, #CT-A888), AG014699 (Rucaparib, #CT-AG01), and BSI201 (Iniparib, #CT-BSI201) were from ChemieTek (Indianapolis, Ind.). AD2281 (Olaparib, #S1060) was obtained from Selleck Chemicals (Houston, Tex.).

Cell Culture and Treatment.

All cells lines were obtained from American Type Culture Collection (ATCC) and maintained in Dulbecco's modified Eagle's medium (DMEM)/F12 or RPMI-1640 supplemented with 10% fetal bovine serum and antibiotics. A1034 and A1471 mouse cell lines were gifts from Dr. Morag Park (McGill University). Cell lines were validated by short tandem repeat (STR) DNA fingerprinting using the AmpFLSTR® Identifiler® PCR Amplification Kit (Life Technologies Grand Island, N.Y.). The STR profiles were compared with ATCC fingerprints and the Cell Line Integrated Molecular Authentication database.

Plasmids and Transfection.

For stable knockdown of c-Met or PARP1 and c-Met or PARP1 overexpression studies, breast cancer cells were transfected with pGIPz shRNA (control) vector (Thermo Fisher Scientific, Rockford, Ill.) or pLKO shRNA vector (Sigma-Aldrich, St. Louis, Mo.) and pCDH-neo vector (System Biosciences, Mountain View, Calif.). Table 1 provides the detailed information on the shRNAs used in the experiments.

TABLE 1 shRNA sequences.

| shRNAs | Clone ID | Sequence | SEQ ID NO |
|---|---|---|---|
| c-Met | Open Biosystem | V3LHS_381509 | CCATCCAGAATGTCATTCT | 2 |
| | Open Biosystem | V3LHS_381508 | GCATTAAAGCAGCGTATC | 3 |
| | Open Biosystem | V3LHS_646098 | GCATTAAAGCAGCGTATC (3'UTR) | 4 |
| | Sigma | TRCN0000196443 | TGTGTTGTATGGTCAATAA | 5 |
| | Sigma | TRCN0000121248 | CCTTCAGAAGGTTGCTGAGTA | 6 |
| PARP1 | Sigma | TRCN0000356550 | TGGAAAGATGTTAAGCATTTA (3'UTR) | 7 |
| BRCA1 | Open Biosystem | V2LHS_90880 | TTCATTTCTAATACCTGCC | 8 |

TABLE 1-continued shRNA sequences.

| shRNAs | Clone ID | | Sequence | SEQ ID NO |
|---|---|---|---|---|
| | Open Bio-system | V2LHS_280394 | TTAAGTCACATAATCGATC | 9 |
| | Open Bio-system | V2LHS_254609 | TTCAGTACAATTAGGTGGG | 10 |
| BRCA2 | Open Bio-system | V2LHS_89237 | TTGTTCAGCAGATTCCATG | 11 |
| | Open Bio-system | V3LHS_376140 | TCTTTAAGACAGCTAAGAG | 12 |
| | Open Bio-system | V3LHS_376141 | TATTAAATGACTCTTTGGC | 13 |

8-OHdG ELISA Assay.

Total DNA was purified from breast cancer cells by using DNeasy Blood & Tissue Kit (Qiagen, Valencia, Calif.). 8-hydroxy-2-deoxyguanosine (8-OHdG) levels in breast cancer cells were measured by using 8-OHdG ELISA kit (Abcam, Boston, Mass.). The mean±s.d. of 8-OHdG levels in each cell line was calculated.

ROS Detection.

Cells were seeded in the 12- or 96-well plates. After overnight growth, cells were incubated with 10 µM 2',7'-dichlorofluorescindiacetate (DCFDA) in PBS for 1 h. Cells were washed and the media replaced with PBS. 2', 7'-dichlorofluorescein (DCF) was measured under a Zeiss microscope with spectra of $495_{EX}$ nm/$529_{EM}$ nm. The mean±s.d. of DCF intensity from five images in each cell line was calculated. Cells were also seeded in 96-well plate. After overnight incubation, cells were treated with 10 µM 2',7'-dichlorofluorescindiacetate (DCFDA) in PBS. After an hour of incubation, medium was replaced with PBS. 2', 7'-dichlorofluorescein (DCF) was measured under plate reader with spectra of $495_{EX}$ nm/$529_{EM}$ nm. The mean±s.d. of DCF levels in each cell line was calculated.

Receptor Tyrosine Kinase Antibody Array.

A Human Phospho-RTK Array Kit (ARY001B) was purchased from R&D Systems (Minneapolis, Minn.). For PARP1-associated proteins study, the manufacturer's protocol was modified. Briefly, MDA-MB-231 cells with endogenous PARP1 knockdown and re-expression of HA tagged wild-type PARP1 were treated with sodium arsenite (As) to induce ROS. Following the instructions of the protocol, cell lysates were incubated with array membranes. The HRP-conjugated HA (#26183-HRP; Thermo Fisher Scientific, Rockford, Ill.) was used to develop the membranes. A GS-800 Calibrated Densitometer (Bio-Rad Laboratories, Hercules, Calif.) was used to quantify the density of the membranes.

Hierarchical Clustering and Display.

Clustering was analyzed with Cluster and TreeView (Eisen et al., 1998) program, as described previously (Hsu et al., 2014). Briefly, the hierarchical clustering algorithm used is based closely on the average-linkage method of Sokal et al. (1958). For any set of target receptor tyrosine kinases, an upper-diagonal similarity matrix was computed by using average-linkage clustering. This algorithm was determined by computing a dendrogram as described previously (Sokal et al., 1958). The heat map was represented graphically by coloring each cell on the basis of the measured fluorescence ratio. Log ratios of 0 (a ratio of 1.0 indicates that the genes are unchanged) were colored in black, positive log ratios were colored in red, and negative log ratios were colored in green.

Immunoprecipitation and Immunoblotting.

For immunoprecipitation (IP), lysates of cells treated as described in the text were precleared with 1 µg of mouse or rabbit IgG and 20 µl of protein G-agarose (Roche, Indianapolis, Ind.) for 1 h at 4° C. Pre-cleared lysates were incubated with 1 µg of primary antibodies or anti-IgG antibody at 4° C. overnight with gentle agitation. Lysates were further incubated with protein G-agarose for 30 min at 4° C. Protein G-agarose pellets were collected and washed three times at 4° C. The immunoprecipitants were subjected to sodium dodecyl sulfate-polyacrylamide gel electrophoresis (SDS-PAGE) and western blot analysis as described previously (Du et al., 2014).

Confocal Microscopy Analysis.

For fixed cells, confocal microscopy assay was performed as described previously (Eisen et al., 1998). Briefly, cells grown on chamber slides (Labtek, Scotts Valley, Calif.) were treated as described in the text. After washing with ice-cold PBS, cells were fixed, permeabilized, and incubated with primary antibodies and fluorescence-labeled secondary antibodies. Immunostained cells were examined using a Zeiss LSM 710 laser-scanning microscope (Carl Zeiss, Thornwood, N.Y.) with a 63×/1.4 objective. The ZEN and AxioVison (Carl Zeiss) and Image J software programs (National Institutes of Health, Bethesda, Md.) were used for data analysis. The mean±s.d. of fluorescence intensity of the indicated antibodies from five images in each treatment group was calculated.

Duolink Assay.

Cells were seeded in chamber slides and treated with the relevant reagents described in the text. Then, cells were fixed, permeabilized, and blocked with 3% BSA. Primary antibodies were incubated with cells and a pair of oligonucleotide-labeled antibodies (PLA probes). Ligation and amplification were done according to the manufacturers' protocol (Duolink Assay Kit, Sigma-Aldrich) before mounting the slide for measurement under confocal microscope. The mean±s.d. of PLA signal intensity from 20 cells in each treatment group was calculated.

Cellular Fractionation.

Cytosolic and nuclear fractions were prepared as described previously (Eisen et al., 1998). Briefly, cells were washed with ice-cold phosphate-buffered saline (PBS), swelled with hypotonic buffer [10 mM Tris-HCl, pH 8.0, 10 mM KCl, 0.5% NP-40, 2 mM $MgCl_2$, 0.5 mM dithiothreitol (DTT), 1 mM PMSF, and 0.15 U/ml aprotinin] and then homogenized using a Dounce homogenizer. Nuclei were pelleted via centrifugation at 600×g for 5 min, and the supernatant was collected as the cytosolic fraction. Nuclear pellets were solubilized and sonicated in an NETN buffer [10 mM Tris-HCl pH 8.0, 150 mM NaCl, 1% NP-40, 1% sodium deoxycholate, 0.1% SDS, 0.5 mM dithiothreitol (DTT), 1 mM PMSF, and 0.15 U/ml aprotinin] followed by centrifugation at 16,000×g for 5 min.

Cell Viability Assay.

Cells (1,500) were seeded in a 96-well plate and treated with the indicated inhibitors for 72 h. Then cells were incubated in fresh media with 100 µM resazurin for 1 h. Cell viability was measured by fluorescent plate readers at spectra of $560_{EX}$ nm/$590_{EM}$ nm. Survival curves were expressed as mean±s.d. relative to DMSO-treated control from three independent experiments.

Clonogenic Cell Survival Assay.

Cells were plated into 12- or 24-well plates. After overnight incubation, cells were treated with inhibitors, which was followed by 8 days of incubation. The colonies were fixed and staining with 0.5% crystal violet, washed, dried and imaged. Crystal violet was resolved from colonies by methanol and measured at 540 nm. Based on the absorbance at 540 nm, survival curves were expressed as a percentage±s.d. relative to DMSO-treated control from three independent experiments.

Luciferase Repair Assay.

Luciferase plasmid was damaged by $H_2O_2$. Purified damaged plasmid was transfected into the cells. Luciferase activity was measured 24 h after transfection.

Soft Agar Anchorage-Independent Cell Growth Assay.

The base layer of cell growth matrix containing DMEM/F12 medium, 10% FBS, and 0.5% agar was paved in 6-well plates (1.5 ml per well). After solidification of the base layer, the top layer (1.5 ml per well) containing DMEM/F12 medium, 10% FBS, and 0.35% agarose, and cells were plated. Culture medium (1 ml) was added to each well and changed every 3 days. After 4-week culture, colonies were stained by 0.005% crystal violet. Colonies were counted by Image J software. Survival curves were expressed as mean±s.d. relative to DMSO-treated control from three independent experiments.

Synergy Quantification of Drug Combination.

Cell growth was measured by cell viability, clonogenic cell survival, or soft agar anchorage-independent cell growth assay. Synergistic effects were determined by Chou-Talalay method to calculate the combination index (CI) (Chou, 2010).

Patient Tissue Samples and Immunohistochemical Staining.

A human breast cancer tissue microarray (#BRC2281, #BRC1021) was obtained from Pantomics (Richmond, Calif.). Human tumor tissue specimens were obtained from patients undergoing surgical resection of breast cancer as primary treatment at MD Anderson Cancer Center or Mackay Memorial Hospital (Taipei, Taiwan) between 1995 and 2009 under the guidelines approved by the Institutional Review Board at MD Anderson, and written informed consent was obtained from patients in all cases at the time of enrollment (Hsu et al., 2014). The tissue microarray was incubated with primary antibody against 8-OHdG, c-Met and pY907-PARP1 and detected with biotin-conjugated secondary antibody and avidin-peroxidase, and visualized by aminoethylcarbazole chromogen. Images were analyzed by ACIS (Dako North America, Carpinteria, Calif.). To validate the specificity of p-Y907-PARP1 antibody in IHC, a peptide competition assay was performed by staining human breast tumor samples with p-Y907-PARP1 antibody blocked with mock or phospho-Y907-PARP1-peptide, non-phospho-Y907-PARP1-peptide, or another phospho-tyrosine peptides, p-Y986-PARP1. The procedure for IHC staining of patient tumor samples was similar.

Comet Assay.

A comet assay was performed to detect DNA strand breaks. Cells were treated as described in the text. Cells were collected and washed with PBS, then mixed with 1% low-melting agarose (Sigma, type VII). The mixture of cells and agarose was layered onto slides pre-coated with 0.5% agarose and covered by slide cover glass on the ice. Five minutes later, the cover glass was gently removed, a third layer of 0.5% agarose was applied, and then the cover glass was replaced. After the agarose solidified, the cover glass was removed and the slides immersed in pre-chilled lysis buffer (2.5 M NaCl, 0.1 M EDTA, 10 mM Tris-HCL pH 7.7, 1% Triton X-100, 1% DMSO) overnight. Slides were washed three times in water for 5 min and incubated with formanidopyrimidine DNA glycosylase (Fpg) enzyme (2 U/slide, Enzymatics, Beverly, Mass.) at 37° C. for 1 h. Then slides were incubated in alkaline electrophoresis buffer (50 mM NaOH, 1 mM EDTA, 1% DMSO, pH 12.8) for 30 min at 4° C. following electrophoresis for 20 min at 22 V. Slides were neutralized with 0.4 M Tris-HCl pH 7.0 and stained with 2 µM propidium iodide in PBS for 30 min. Comet tails were imaged by fluorescence microscope and analyzed by using the Image J software. The mean±s.d. of DNA intensity in the tail from 20 cells in each treatment group was calculated.

In Vitro Kinase Assay.

Recombinant GST-Wt-PARP1 fragment, GST-Y907F-PARP1 fragment and GST-Y986F-PARP1 fragment were expressed by induction of isopropyl β-D-1-thiogalactopyranoside (IPTG) and purified with glutathione agarose beads. After cold-PBS washing 3 times, beads were suspended with 500 µl 1× kinase buffer, with 50 µl saved for western blotting with GST. The beads were spun down and 100 µM ATP, 0.5 µg human recombinant active c-Met protein and 50 µCi [$\gamma^{32}$P]-ATP were added in 50 µl kinase buffer at 30° C. for 15-30 min. The kinase reaction was stopped by heating at 100° C. for 5 min in SDS loading dye. The samples were subjected to two identical SDS-PAGE assays. One was used for Coomassie blue staining of GST fusion PARP1 protein. The second gel was dried and used to detect phosphorylation of substrate by autoradiograph.

PARP Enzyme Activity Assay.

PARP1 enzyme activity was measured by using a commercial assay kit from EMD Millipore. Following the protocol of the manufacturer with minor modification, 500 ng of total lysates was added to each reaction. The dose course of PARP inhibitor, ABT-888 was from 0.01 to 1,000 µM. PARP enzyme activity of wild-type and mutants was determined after incubation with the substrate was measured by a plate reader.

Mouse Xenograft Models.

All animal procedures were conducted under the approval of the Institutional Animal Care and Use Committee (IACUC) at MD Anderson Cancer Center (protocol number 10-14-07231). Female nude mice at 6-8 weeks of age were injected in their mammary fat pads with $0.5 \times 10^6$ MDA-MB-231 cells, $2 \times 10^6$ HCC1937 cells or $5 \times 10^6$ MCF-7 cells. Female FBV at 6-8 weeks of age were injected in their mammary fat pads with $0.5 \times 10^6$ A1034 cells. H1993 cells were injected subcutaneously into the right flank of female nude mice at 6-8 weeks of age. For MDA-MB-231 and A1034 cells xenograft mouse models, mice were imaged with the IVIS Imaging System 5 days after injection and were divided into treatment groups (n=10). Crizotinib (5 mg/kg) and foretinib (5 mg/kg), AG014699 (5 mg/kg) and ABT-888 (25 mg/kg) were dissolved in aqueous 50 mM sodium acetate, pH 4, and were administered as single agents or in combination. After 2 weeks of treatment, tumor sizes were assessed using with the IVIS Imaging System. Mice were injected with 100 µl of D-luciferin (Xenogen; 15 mg/ml in PBS). After 10 min, mice were anesthetized with a mixture of oxygen and isoflurane (Inhalation Anesthesia System; Matrix Medical, Orchard Park, N.Y.) and underwent imaging with the IVIS Imaging System. Imaging parameters were maintained across experiments for comparative analyses. Tumor samples were collected after final treatment and analyzed by immunofluorescence staining. For toxicity assessment, mice were weighed before and after treatment. Blood samples were collected after treatment. Biochemical analysis of liver marker enzymes alanine transaminase (ALT) and aspartate transaminase (AST) and kidney marker by-products, creatinine and blood urea nitrogen were used to evaluate treatment toxicity. All the in vivo experiments were conducted with 10 mice for each condition. No statistical methods were used to predetermine sample size.

Statistical Analysis.

Unless otherwise noted, each sample was assayed in triplicate. Each experiment was repeated at least three times. All error bars represent s.d. Student's t-test was used to compare two groups of independent samples. Repeated measure ANOVA analysis was used to evaluate the statistical significance during dose curve response. Correlations were analyzed using the Pearson chi-square test.

Example 1—ROS Induces Association of c-Met and PARP1

Figure 1B:
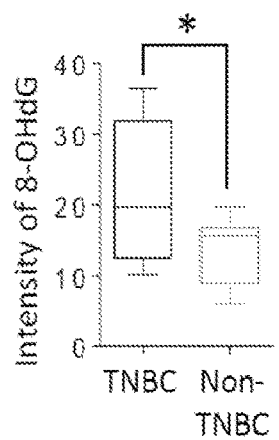
Figure 1C:
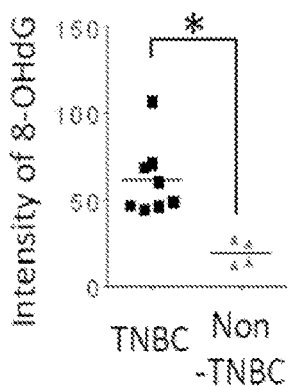
Figure 1D:
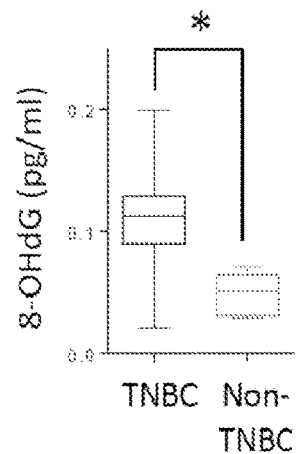
Figure 1E:
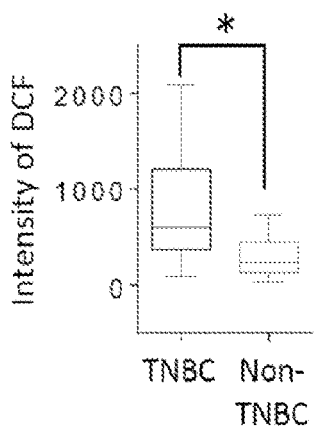
Figure 1F:
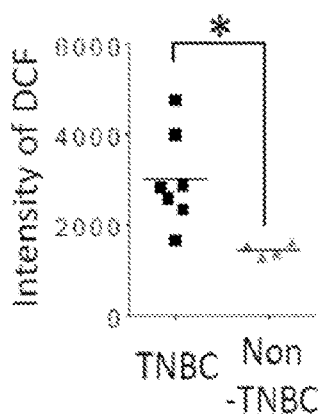
Figure 1G:
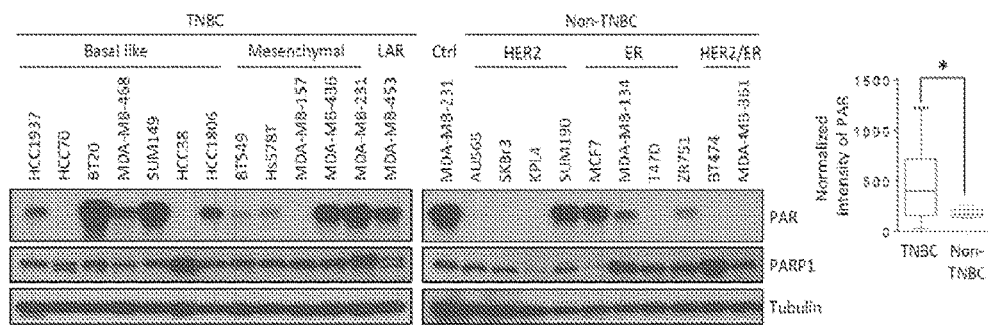
Figure 1H:
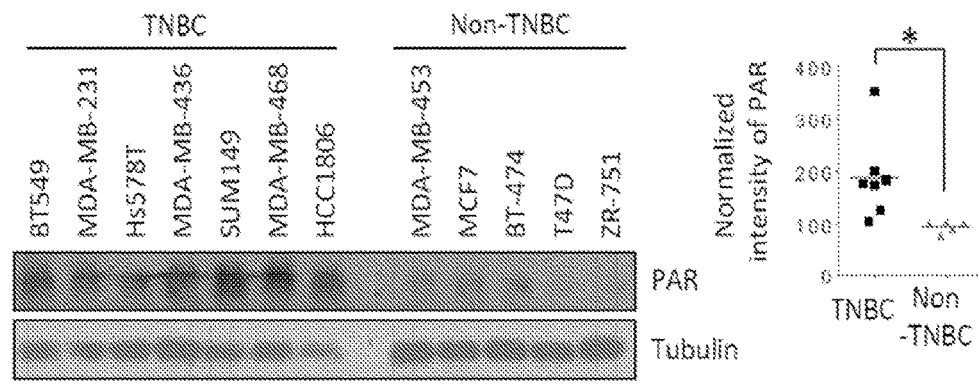
Figure 5:
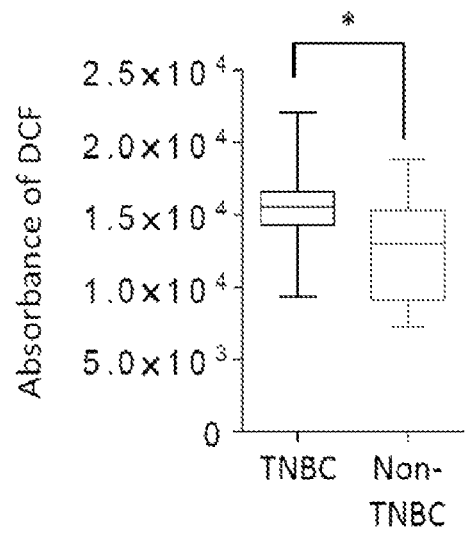
FIG. 5. The levels of 8-OHdG and DCF are higher in TNBC. Breast cancer cells ($4 \times 10^3$) were seeded onto 96-well plates and treated with 10 μM of DCF-DA for 30 min. DCF was measured by plate reader and analyzed with GraphPad Prism. Quantitation of triplicated experiment is shown. Error bars represent s.d. *P<0.05, t-test.

The levels of 8-hydroxydeoxyguanosine (8-OHdG), a marker for oxidative damaged DNA by ROS, were higher in TNBC than in non-TNBC as shown by IHC staining of the breast cancer tissues microarray (FIG. 1A). Consistent with observations in tumor tissues of breast cancer patients, the 8-OHdG level was also higher in TNBC cell lines than non-TNBC cell lines as seen by immunofluorescence staining and ELISA assay (FIGS. 1B-D). The ROS marker, 2',7'-dichlorofluorescein (DCF), was also higher in most TNBC cell lines than in non-TNBC cell lines (FIGS. 1E-F and 5). It was then asked whether higher ROS and oxidative DNA damage in TNBC turn on PARP1 activity. Indeed, TNBC cells had higher PARylation than non-TNBC cells (FIG. 1G-H). Together, these results suggest that the TNBC-associated increase in ROS may lead to higher PARP1 activity to repair cellular ROS-induced DNA damage.

Figure 1I:
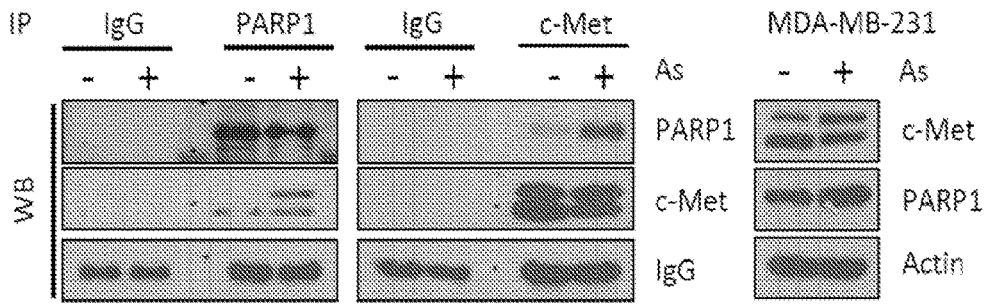
Figure 1J:
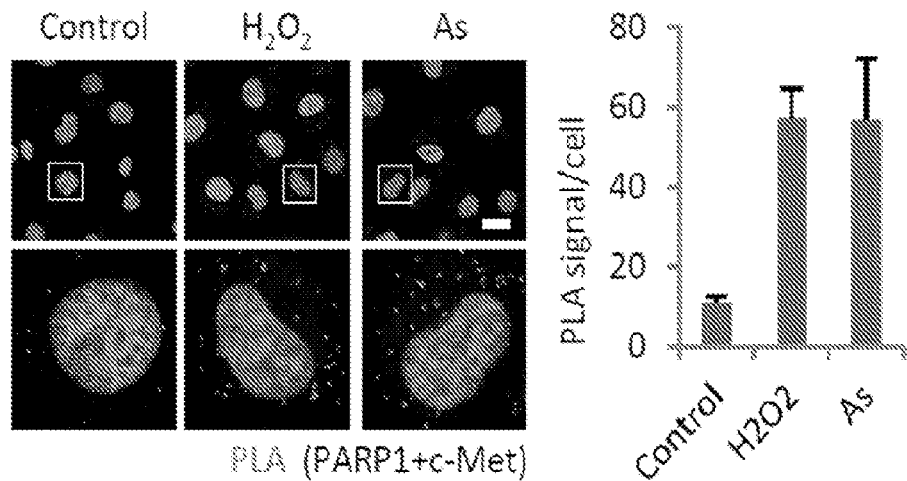
Figure 1K:
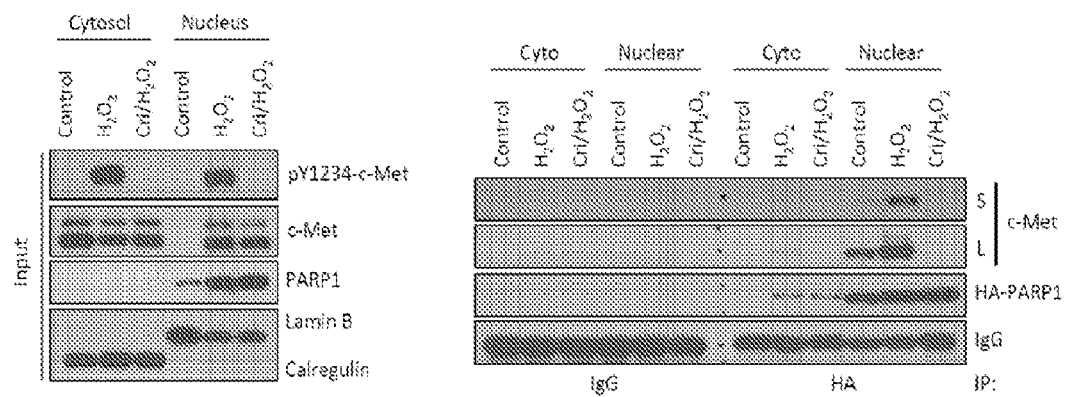
Figure 6A:
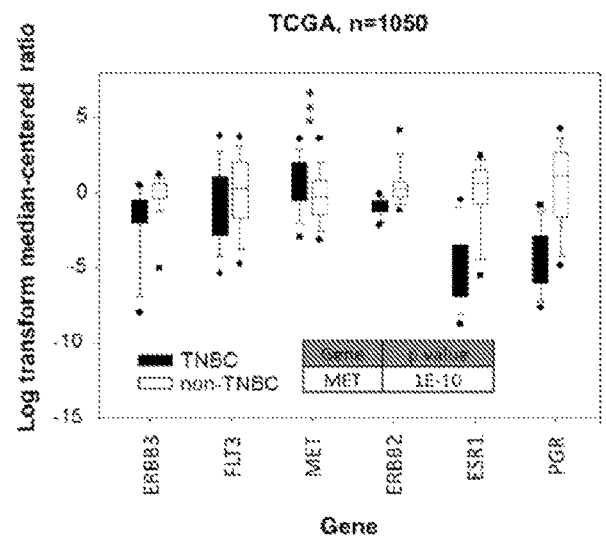
FIGS. 6A-B. TCGA database analysis of ERBB3, MET, and FLT3.
Figure 6B:
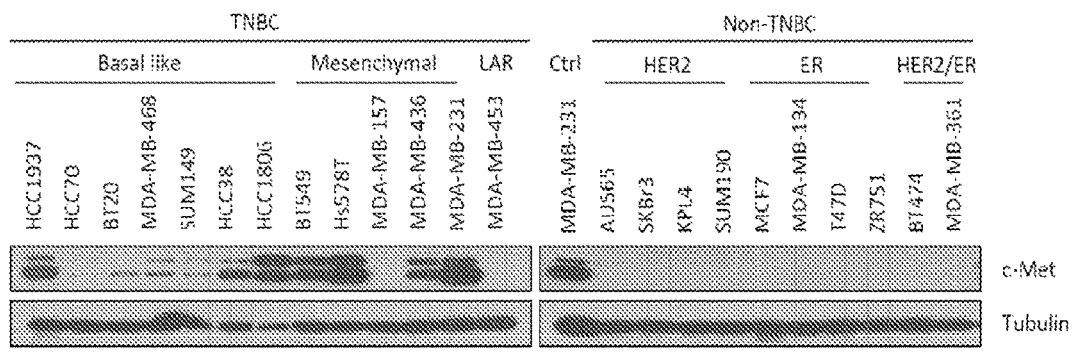

Receptor tyrosine kinases are druggable targets that are commonly overexpressed in TNBC and known to play critical roles during tumorigenesis (Casaletto and McClatchey, 2012; Speers et al., 2009; Hsu et al., 2014). To investigate the underlying molecular mechanisms regulating PARP1 response under ROS-induced oxidative stress and identify potential druggable partners, receptor tyrosine kinases that may associate with PARP1 upon ROS stimulation and are also activated in TNBC were searched for. To this end, MDA-MB-231 TNBC cells were treated with sodium arsenite (As) to induce ROS, and cell lysates were then subjected to an antibody array (Human Phospho-RTK Array) to identify PARP1-associated kinases. The targets that are induced by As (cutoff ratio 3.0; Table 2) and related to TNBC based on hierarchical cluster analysis from TCGA database (FIG. 6A) were further narrowed down and c-Met (HGFR) was identified as the top candidate. As a proto-oncogene, c-Met has also been shown to correlate with poorer patient survival in TNBC (Speers et al., 2009; Hsu et al., 2014; Zagouri et al., 2013) and is activated by ROS (Fischer et al., 2004). Higher expression of c-Met in TNBC than in non-TNBC breast cancer cell lines also suggested the importance of c-Met (FIG. 6B), and thus whether c-Met regulates PARP1 function in TNBC was first investigated. The exogenous and endogenous association between c-Met and PARP1 was further validated in HEK293T cells (FIGS. 7A-B) and in MDA-MB-231 cells (FIGS. 1I and 7C), respectively. Furthermore, the interaction between c-Met and PARP1 was detected in other cell lines, such as HCC1937 (endogenous, FIG. 7D) and MDA-MB-436 or MCF7 (with ectopic expression of c-Met, FIGS. 7E-F) with results indicating that their interaction was enhanced under oxidative stress by $H_2O_2$ and As treatment. Similar results from Duolink assay were observed (FIG. 1J). In addition, cellular fractionation showed that $H_2O_2$ treatment enhanced the association between c-Met and PARP1 in the nucleus in a kinase-dependent manner (FIG. 1K). The study further demonstrated that c-Met translocates into the nucleus via a mechanism similar to that of EGFR nuclear transport (Du et al., 2014) requiring motor protein dynein (FIG. 7G). Together, these findings suggest that oxidative stress induces nuclear transport of c-Met and its interaction with PARP1. The link connecting ROS to nuclear c-Met and PARP1 in DNA damage response raises an interesting question whether c-Met also regulates PARP1 functions. If so, c-Met may alter the cellular response to PARP inhibition.

TABLE 2

PARP1-associated receptor tyrosine kinases.

| | Density $OD/mm^2$ | | |
|---|---|---|---|
| | As | Control | Ratio |
| ErbB3 | 23.061 | 3.852519703 | 5.985938094 |
| HGFR | 13.807 | 2.946213335 | 4.686244839 |
| Flt3 | 42.240 | 10.88344393 | 3.881120605 |
| VEGFR3 | 25.529 | 17.06784509 | 1.495727621 |
| EphB2 | 12.819 | 8.607059731 | 1.489328534 |
| EGFR | 12.570 | 9.156356358 | 1.372816818 |
| ErbB2 | 520.116 | 434.4554231 | 1.197166744 |
| ALK | 670.275 | 583.7624694 | 1.148198284 |
| DDR2 | 640.615 | 598.8694844 | 1.069706878 |
| Mer | 516.543 | 495.542309 | 1.042378358 |
| TrkC | 276.327 | 271.5992359 | 1.017408391 |
| EphA1 | 780.733 | 770.5254552 | 1.013247903 |
| VEGFR2 | 16.867 | 16.69742454 | 1.010174895 |
| EphB3 | 502.292 | 500.9364975 | 1.002706551 |
| DDR1 | 644.396 | 645.9064367 | 0.997661727 |
| InR | 662.264 | 665.1545094 | 0.995654772 |
| Tie2 | 583.836 | 602.581307 | 0.968892229 |
| EphB4 | 466.542 | 498.073405 | 0.9366925 |
| RYK | 555.220 | 599.8229837 | 0.925639074 |
| EphA6 | 11.551 | 12.98600868 | 0.88945757 |
| EphA10 | 665.579 | 774.3254247 | 0.859559485 |
| FGFR1 | 461.048 | 539.9789275 | 0.853825092 |
| M-CSFR | 16.217 | 19.96710542 | 0.812195286 |
| c-Ret | 211.554 | 281.5983914 | 0.751260401 |
| ROR2 | 370.936 | 518.1384253 | 0.715901668 |
| MuSK | 42.566 | 61.43813773 | 0.692823445 |
| FGFR2a | 259.560 | 386.0421566 | 0.672361325 |
| EphA2 | 31.664 | 49.21956664 | 0.643315702 |
| FGFR4 | 12.421 | 26.60337603 | 0.466901459 |
| PDGFRb | 27.706 | 60.50020535 | 0.457943638 |
| EphA5 | 13.186 | 31.14416218 | 0.423381107 |
| EphA4 | 202.694 | 499.6224292 | 0.405695258 |
| Axl | 133.630 | 383.0229985 | 0.348883003 |
| FGFR3 | 55.899 | 178.7072453 | 0.312797833 |
| ROR1 | 23.217 | 78.47721684 | 0.295846446 |
| Tie1 | 129.403 | 477.74058 | 0.270863609 |
| EphA3 | 73.273 | 306.8988082 | 0.238754316 |
| Dtk | 105.659 | 539.9065894 | 0.19569831 |
| IGF-IR | 22.261 | 128.6637776 | 0.173014375 |

Example 2—c-Met Regulates Resistance to PARP Inhibitors

Figure 2A:
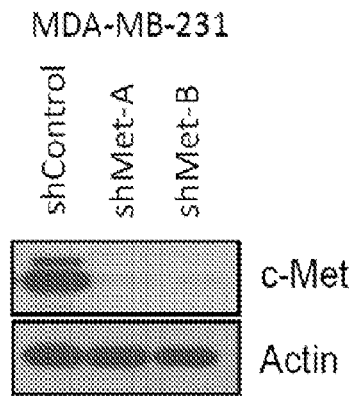
FIGS. 2A-R. c-Met regulates resistance to PARP inhibitors.
Figure 2B:
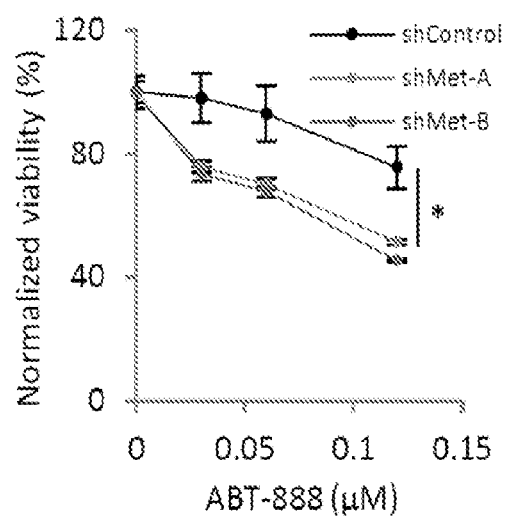
(FIGS. 2B-C) c-Met knockdown cells were treated with PARP inhibitors (ABT-888 and AG014699) and subjected to cell viability assay. Data shown as mean±SEM of triplicate experiments (n=3). *P<0.05, t-test.
Figure 2C:
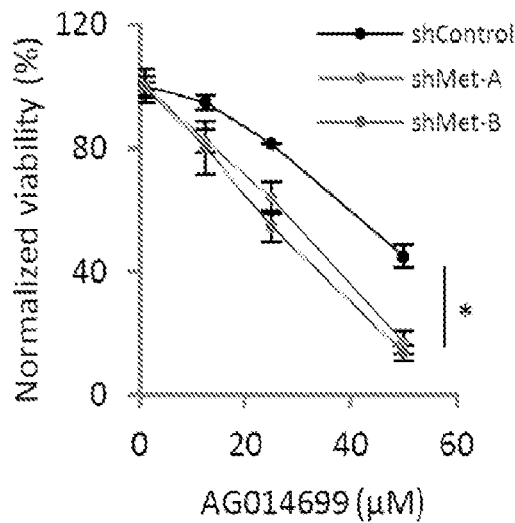
Figure 2D:
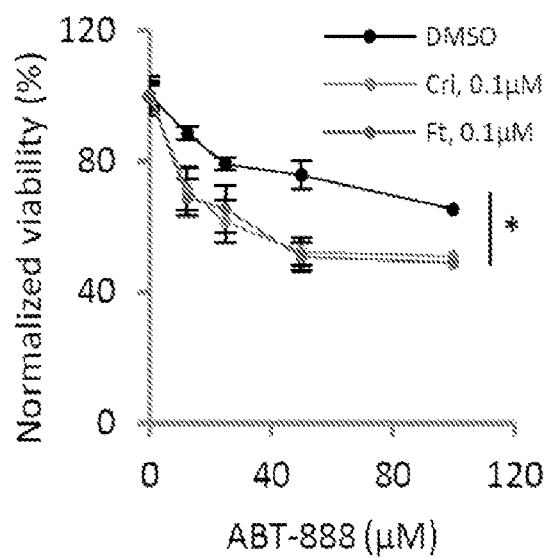
(FIG. 2D) MDA-MB-231 cells were treated with ABT-888 and crizotnib or foretinib and subjected to cell viability assay.
Figure 2E:
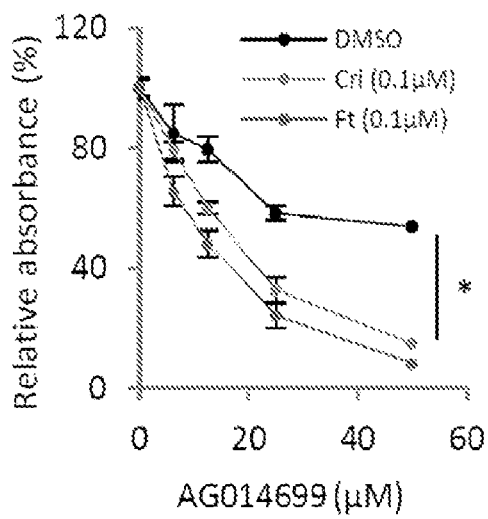
(FIG. 2E) MDA-MB-231 cells were treated with AG014699 and crizotinib or foretinib and subjected to clonogenic cell survival assay. Quantitation is shown.
Figure 2F:
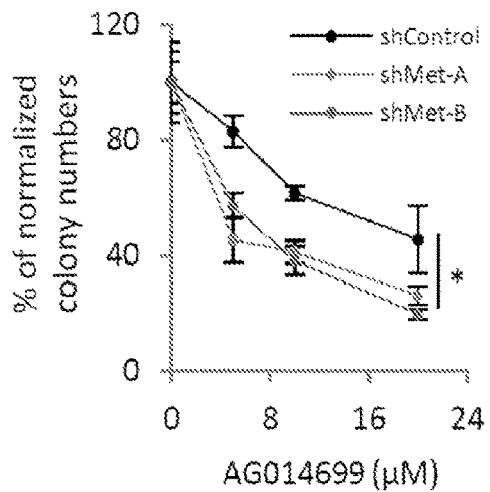
(FIG. 2F) c-Met knockdown cells were treated with AG014699 and subjected to soft agar colony formation assay to determine anchorage-independent cell growth. Quantitation is shown.
Figure 8E:
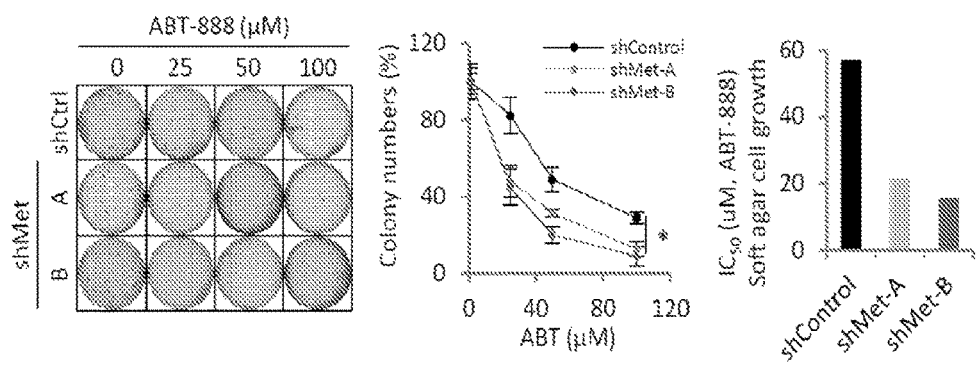
Figure 8F:
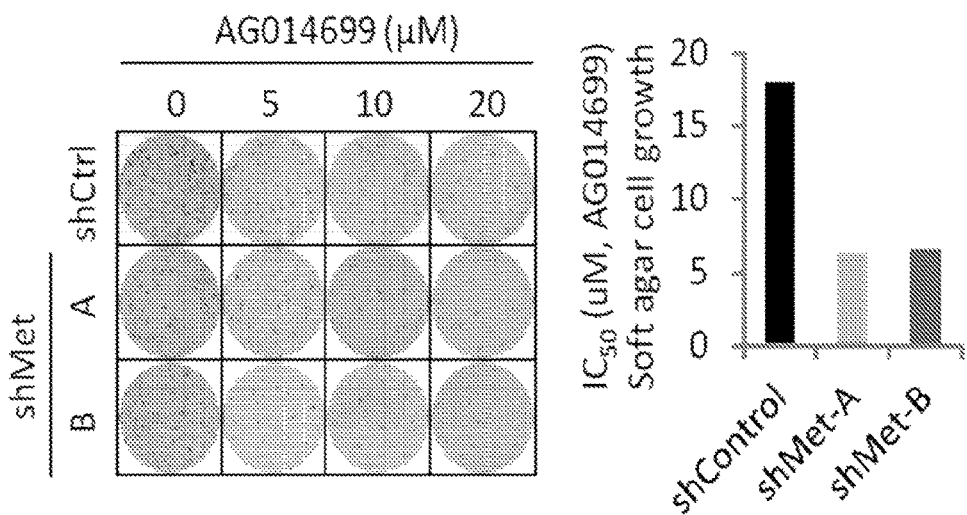
Figure 8G:
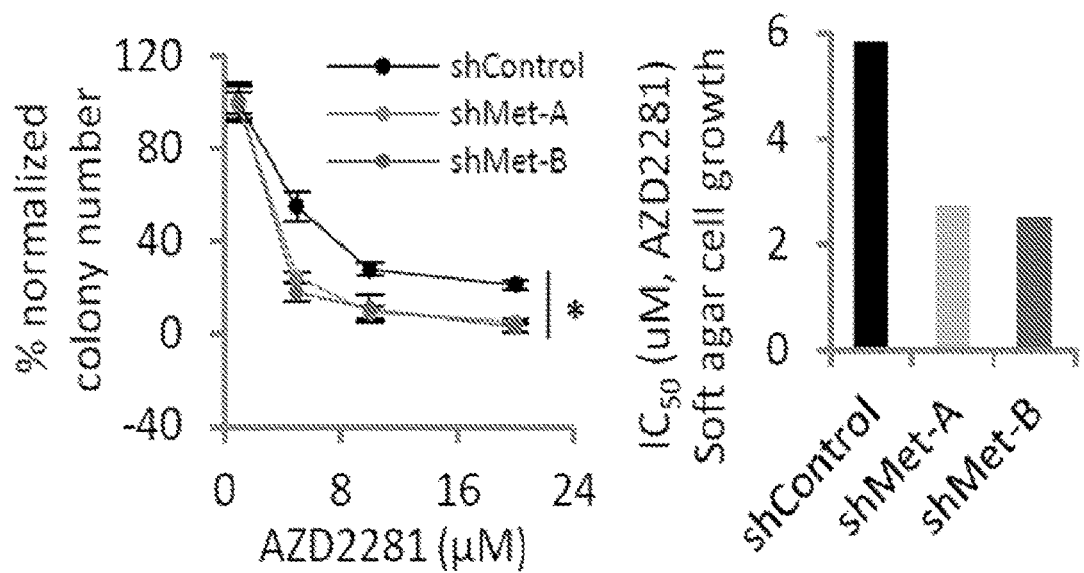
Figure 8H:
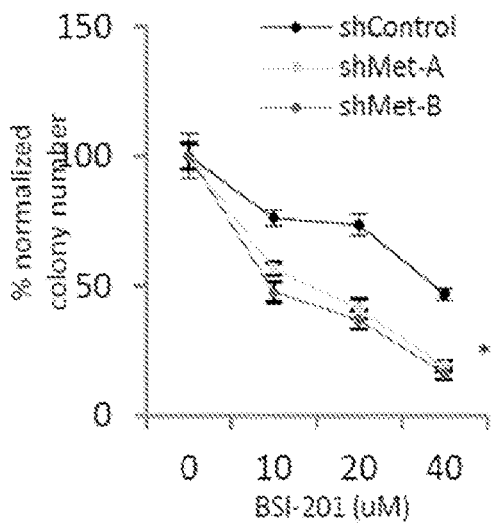
Figure 8I:
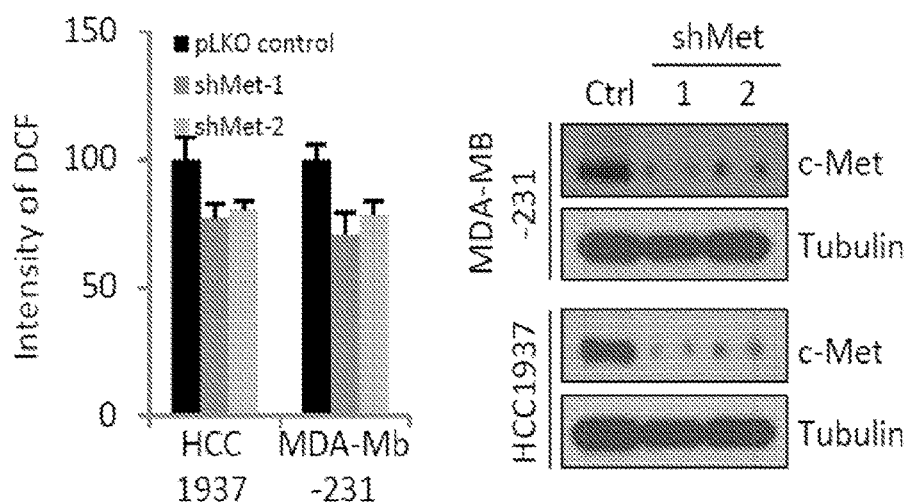
Figure 8J:
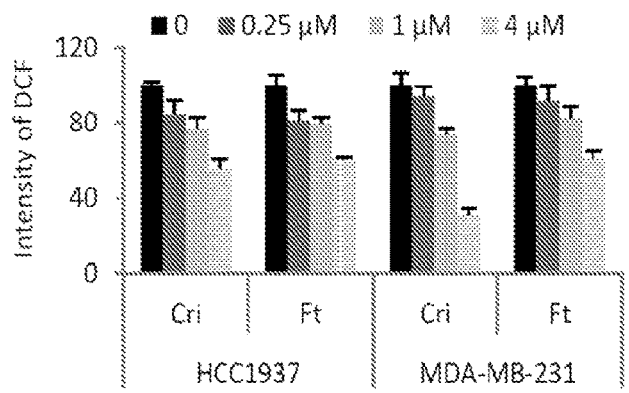

To determine whether c-Met plays a role in the response to PARP inhibition, cell growth and colony formation ability were examined in the presence of three different PARP inhibitors, olapanib (AZD2281, approved by the U.S. Food and Drug Administration (FDA)), veliparib (ABT-888), and rucaparib (AG014699), which have been evaluated in clinical trials. Indeed, knocking down c-Met rendered MDA-MB-231 cells more sensitive to the PARP inhibitors as indicated by decreased cell viability (FIGS. 2A-C and FIGS. 8A-C). Consistent with knocking down c-Met, inhibition of c-Met by inhibitors, crizotinib, and foretinib also enhanced the sensitivity of cells to PARP inhibitors (FIGS. 2D-E and 8D). In addition, anchorage-independent cell growth was also decreased when c-Met was knocked down (FIGS. 2F and 8E-H). In line with previous findings (Jagadeeswaran et al., 2007), inhibition of c-Met either by shRNAs or small molecular inhibitors all led to the reduction of ROS (FIGS. 8I-J), suggesting that a feedback regulation of c-Met activation and ROS may be involved in the PARP1-mediated DNA damage response and PARP inhibitor response.

Figure 2G:
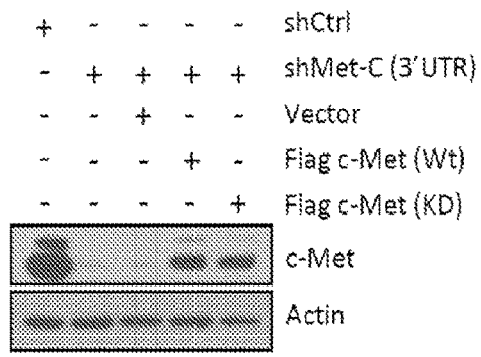
(FIG. 2G) Western blot analysis of c-Met knockdown at the 3'UTR (shMet-C) and re-expression of c-Met wild-type (Wt) and kinase dead (KD) in MDA-MB-231 cells.
Figure 2H:
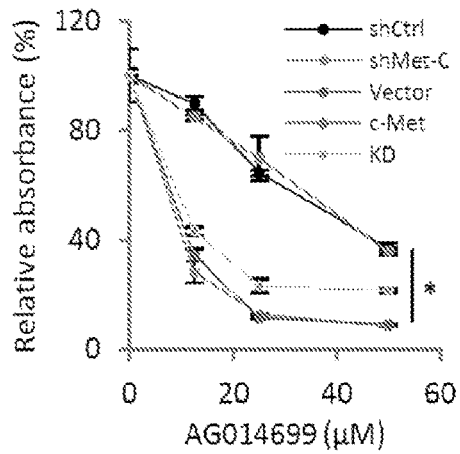
(FIG. 2H) MDA-MB-231 cells with 3'UTR c-Met knockdown and re-expression of wild-type or kinase dead (KD) c-Met were treated with AG014699 and subjected to clonogenic cell survival assay. Quantitation is shown.
Figure 2I:
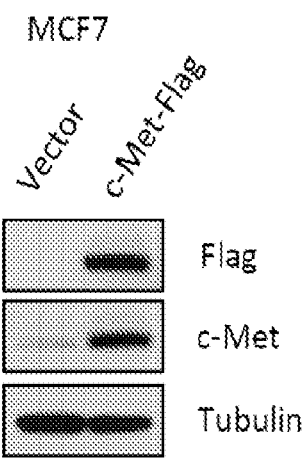
(FIG. 2I) Western blot analysis of c-Met expression in MCF-7 cells (MCF-7/c-Met).
Figure 2J:
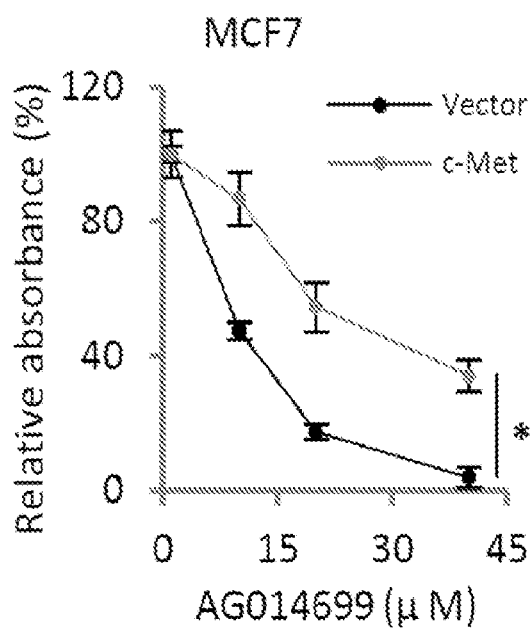
(FIGS. 2J-K) MCF-7/c-Met cells were treated with AG014699 and subjected to clonogenic cell survival assay and soft agar assay.
Figure 2K:
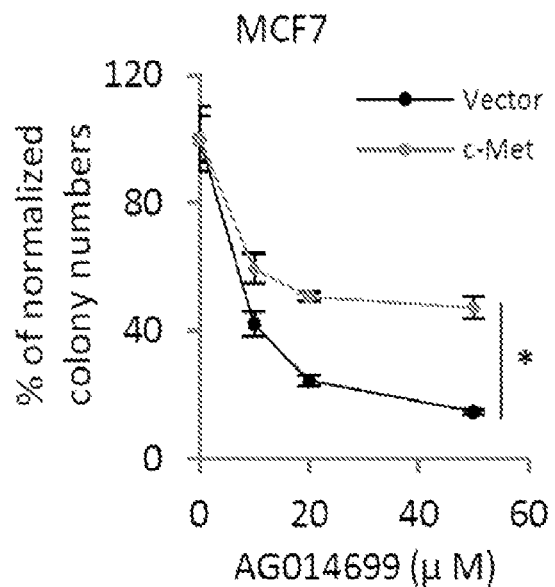
Figure 8K:
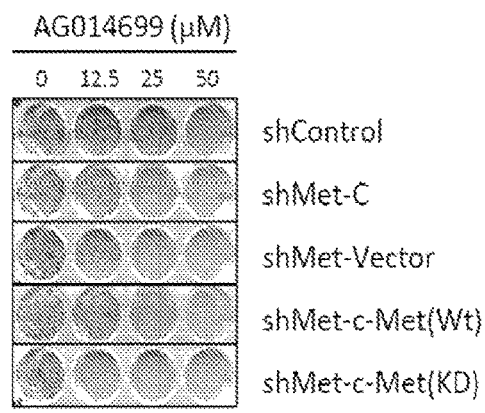
Figure 8L:
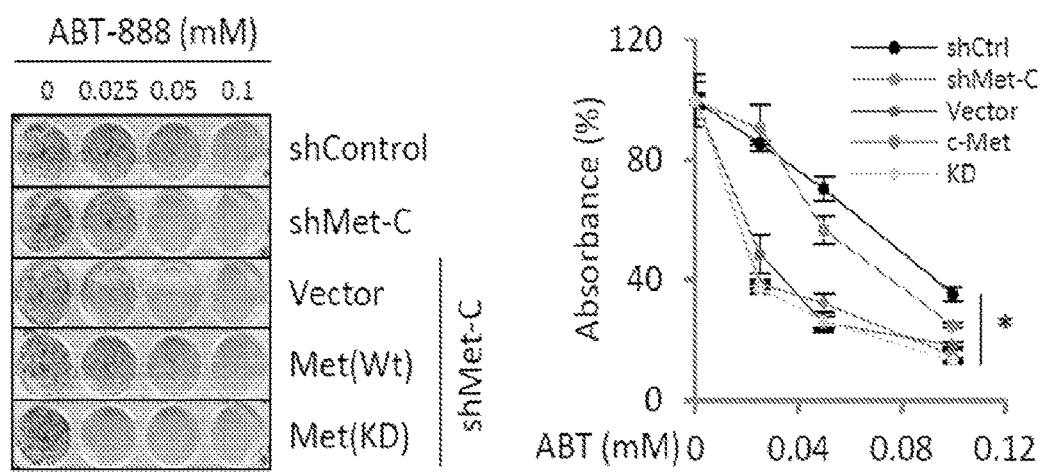
Figure 8M:
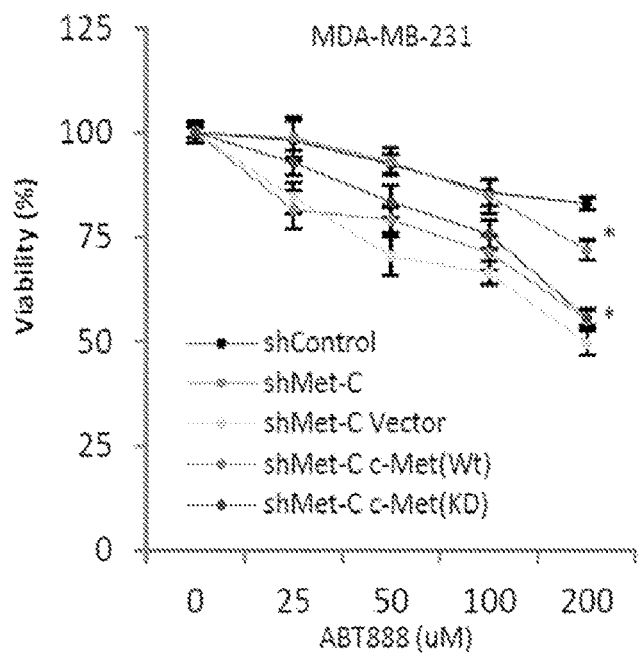
Figure 9E:
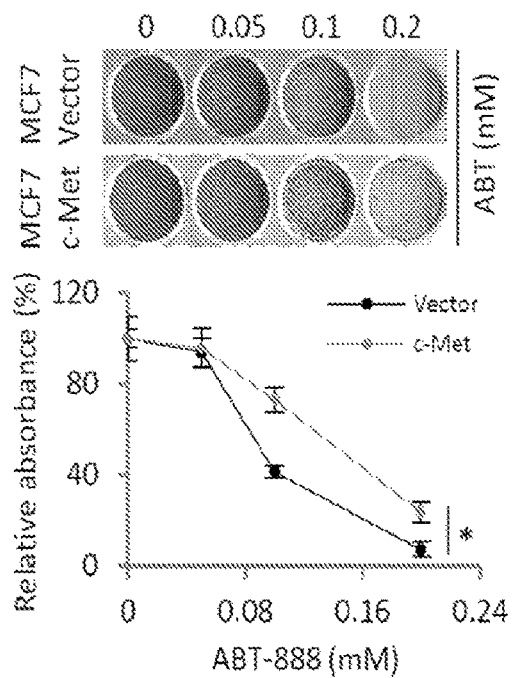
Figure 9F:
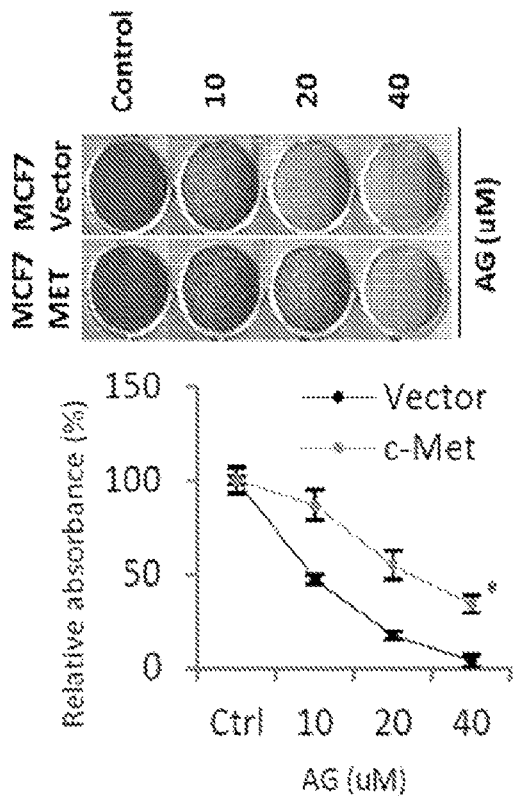
Figure 9G:
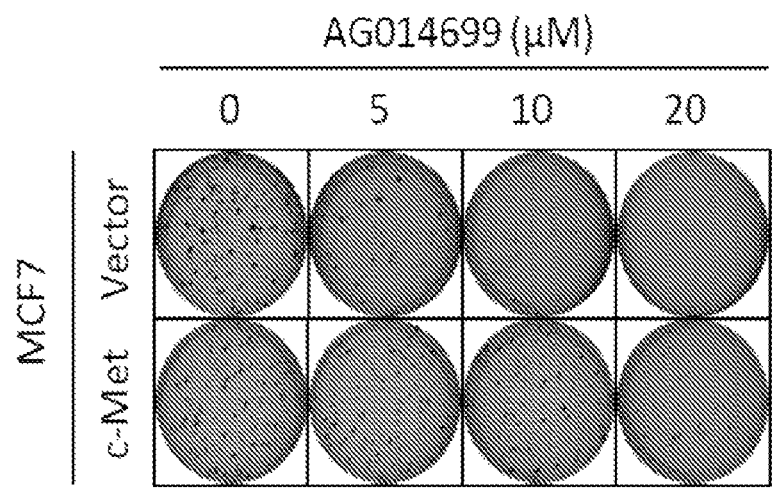
Figure 9H:
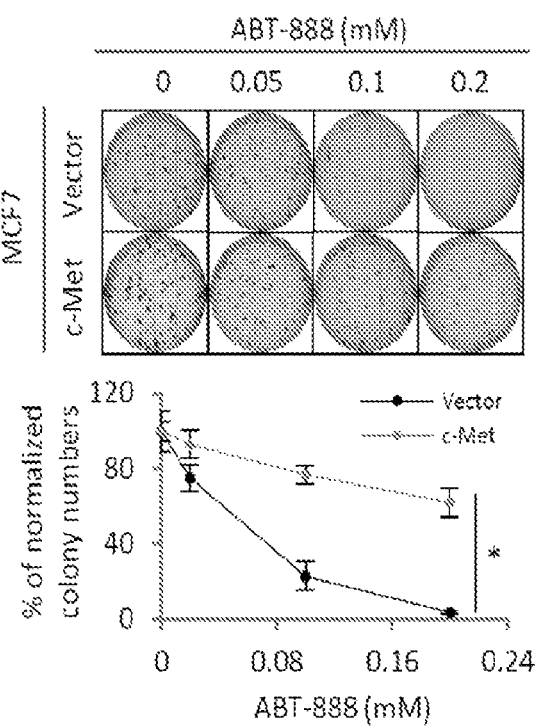
Figure 9I:
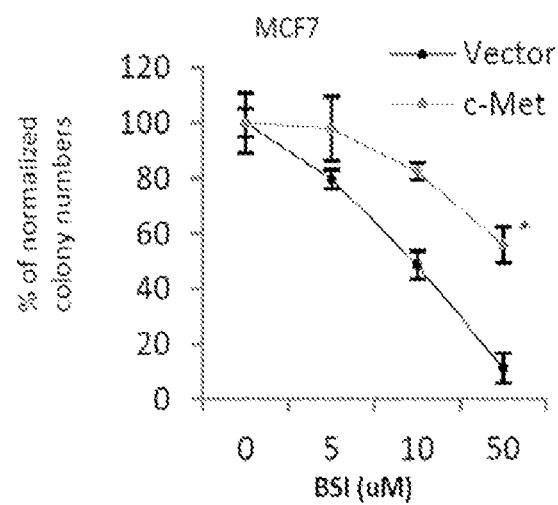

To further investigate the function of c-Met during PARP inhibitor response, wild-type and kinase dead (KD) mutant c-Met were re-expressed in endogenous c-Met knockdown MDA-MB-231 cells (FIGS. 2G and 8M) and found that only re-expression of wild-type c-Met increased the clonogenic cell survival (FIG. 2H and FIGS. 8K-L). MCF-7 cells ectopically expressing c-Met (FIG. 2I) had increased cell viability (FIGS. 9A-D), clonogenicity (FIGS. 2J and 9E-F), and anchorage-independent cell growth (FIGS. 2K and 9G-I) under PARP inhibition. These results are in line with those observed in which downregulation of c-Met increased the sensitivity of cells to PARP inhibitors. Of note, the doses used here for the in vitro assays were comparable to those used in previous studies (Lehmann et al., 2011; Anders et al., 2013). Together, these results indicate that c-Met attenuates response to PARP inhibitors.

Figure 2L:
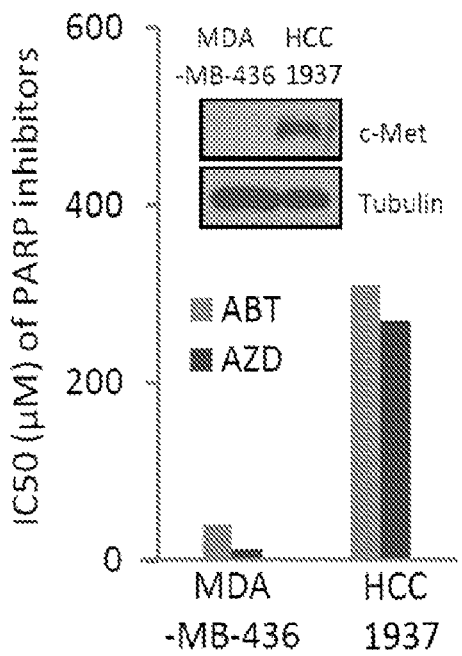
(FIG. 2L) $IC_{50}$ of PARP inhibitors in BRAC1 mutant TNBC cells (MDA-MB-436 and HCC1937). c-Met expression by Western blot analysis is shown in inset.
Figure 2Q:
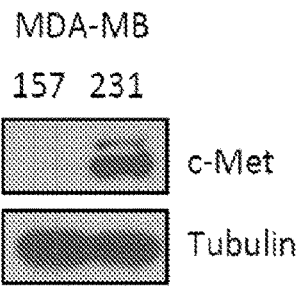
Figure 2R:
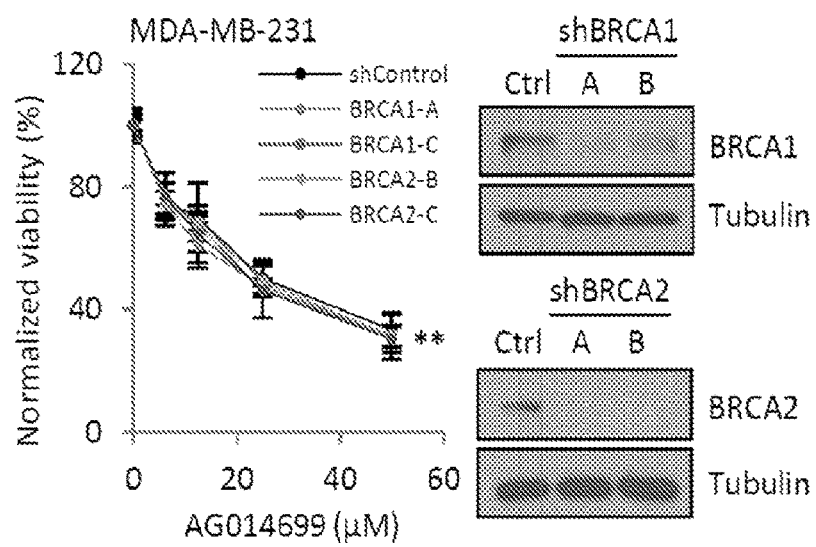
Figure 2S:
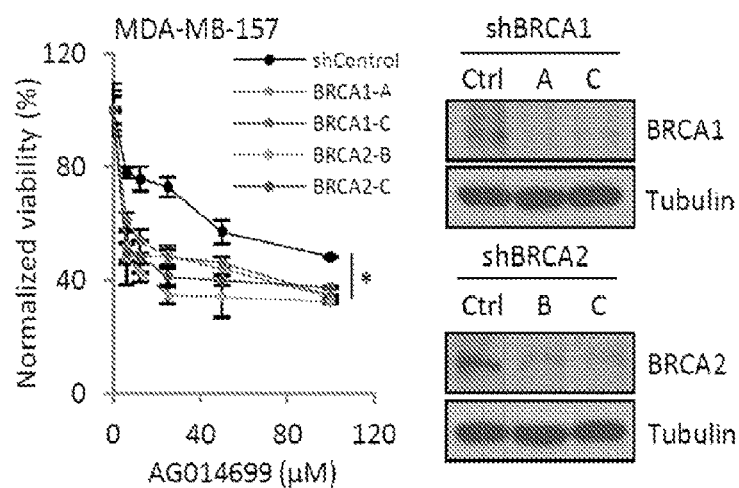
Figure 10A:
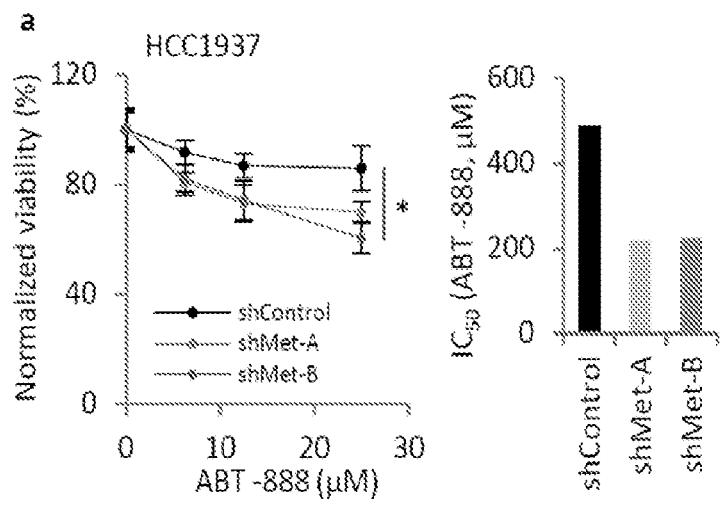

While BRCA mutations and deficiency are thought to be the major predictive markers for response to PARP inhibitors (Farmer et al., 2005; Bryant et al., 2005), not all patients carrying BRCA mutations respond well to PARP inhibition (Lord and Ashworth, 2013). For instance, although both MDA-MB-436 and HCC1937 cells harbor BRCA mutations, MDA-MB-436 cells are sensitive to PARP inhibition whereas HCC1937 cells are resistant (Lehmann et al, 2011) (FIG. 2L). On the basis of prior results, the differences in PARP-inhibitor response observed in BRCA-mutated TNBC cells was speculated to be attributed to the differential expression of c-Met. Indeed, Western blot analysis indicated that HCC1937 cells that were more resistant to PARP inhibition expressed substantially higher levels of c-Met than MDA-MB-436 cells (FIG. 2L). In line with this result, knocking down c-Met rendered HCC1937 cells more sensitive to PARP inhibition (FIGS. 2M-N and 10A-B) whereas increasing the ectopic expression of wild-type c-Met but not kinase dead mutant in MDA-MB-436 cells attenuated their response to PARP inhibition (FIGS. 2O-P and 10C-D). It is worthwhile to note that knockdown or ectopic expression of c-Met had no effect on the BRCA1/2 protein level (FIGS. 10E-F). To further investigate the relationship between BRCA1/2 and c-Met, both of which play an important role in PARP inhibitor response, BRCA1 and BRCA2 expression was knocked down in a pair of wild-type BRCA1 and BRCA2 cell lines with high (MDA-MB-231) and low (MDA-MB-157) c-Met expression (FIG. 2Q) and subjected them to PARP inhibitors. Interestingly, knocking down BRCA1 or BRCA2 sensitized only cells expressing low levels of c-Met (FIGS. 2R-S and 10G-J). Collectively, these results suggest that enhanced expression of c-Met kinase renders cells resistant to PARP inhibitors even under BRCA inactivation and provide a molecular explanation for this long-term puzzle.

Example 3—c-Met Mediates PARP1 Functions Through Phosphorylation of PARP1 at Y907

Figure 3A:
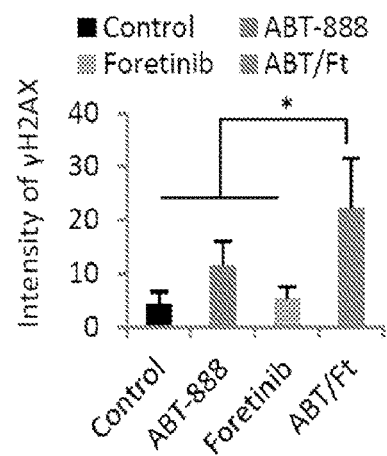
FIGS. 3A-I. c-Met mediates PARP1 functions through phosphorylation of PARP1 at Y907.
Figure 3B:
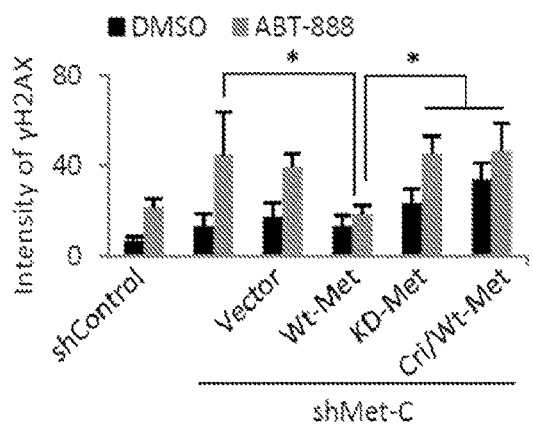
Figure 11B:
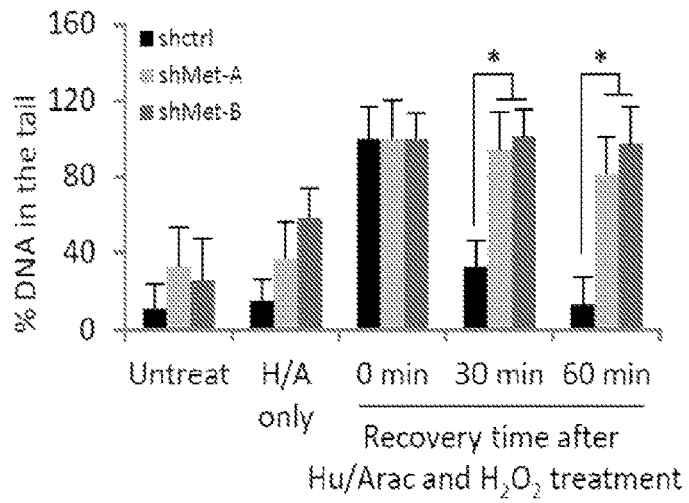
Figure 11C:
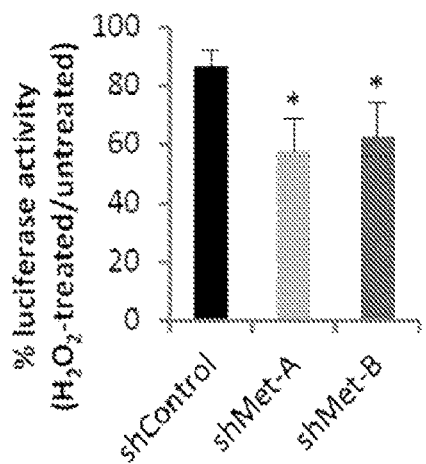
Figure 11D:
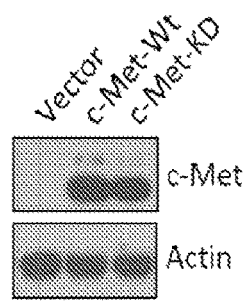
Figure 11E:
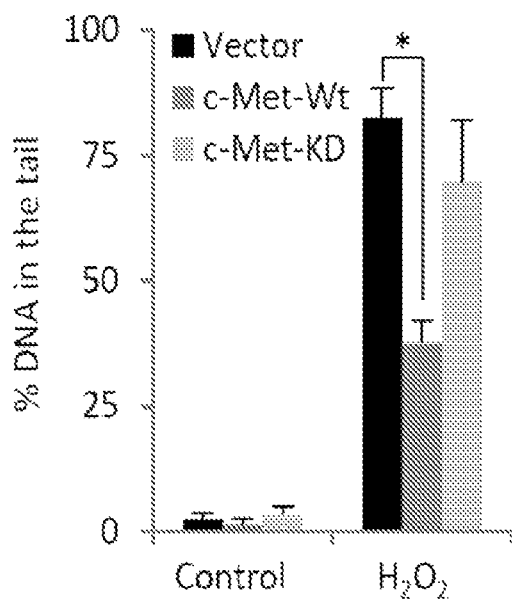
Figure 11F:
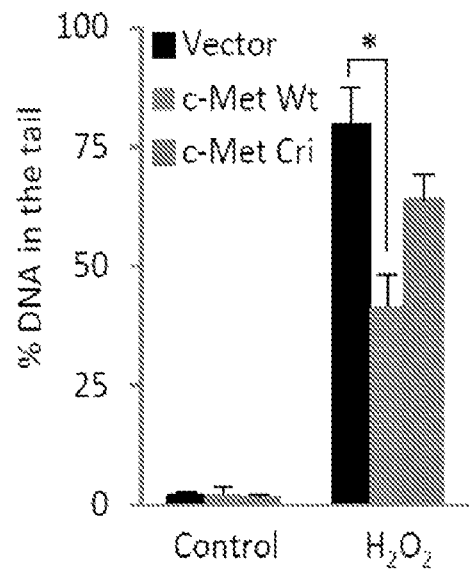

Next, it was asked whether c-Met activates PARP1 functions. To address this, MDA-MB-231 cells were exposed to $H_2O_2$ with or without c-Met knockdown and subjected to a comet assay to evaluate the extent of DNA damage. Cells with c-Met knockdown had higher tail intensity, which is indicative of increased oxidative DNA damage, than the control cells (FIG. 11A). To determine whether the increase in DNA damage was a result of decreased DNA repair, a DNA repair assay was performed in which cells were treated with Hu/Arac (hydroxyurea/1-fl-D-Arabinofuranosylcytosine) to accumulate $H_2O_2$-damaged DNA and then allowed to recover after different time points, at which the percentage of repaired DNA was measured. c-Met knockdown cells were less efficient in DNA repair compared with control cells (FIG. 11B). Results from a luciferase repair assay also demonstrated a reduction in DNA repair function in the absence of c-Met when cells were transfected with $H_2O_2$-damaged luciferase plasmid (FIG. 11C). Consistent with knockdown of c-Met, inhibition of c-Met by crizotinib also increased the sensitivity of cells to PARP inhibitor ABT-888 as indicated by enhanced γH2AX foci formation, a marker of DNA damage (FIG. 3A). DNA repair also required the kinase activity of c-Met as expression of wild-type but not kinase dead c-Met in MCF-7 cells to reduce $H_2O_2$-induced DNA damage, which was restored by pre-treatment with a c-Met inhibitor (FIGS. 11D-F). Ectopic expression of c-Met in MCF-7 cells also decreased ABT-888-induced γH2AX foci formation, a marker of DNA damage. In addition, MDA-MB-231 cells with c-Met knockdown had higher γH2AX foci formation than those with vector control under ABT-888 treatment (FIG. 3B, top left), which was attenuated under re-expression of wild-type c-Met but not under the vector control (FIG. 3B, bottom left), kinase dead c-Met or wild-type c-Met plus c-Met inhibitor, crizotinib pre-treatment (FIG. 3B, top right). These findings together suggest that c-Met enhances the DNA repair function of PARP1 in response to oxidative DNA damage through a kinase-dependent mechanism.

Figure 3C:
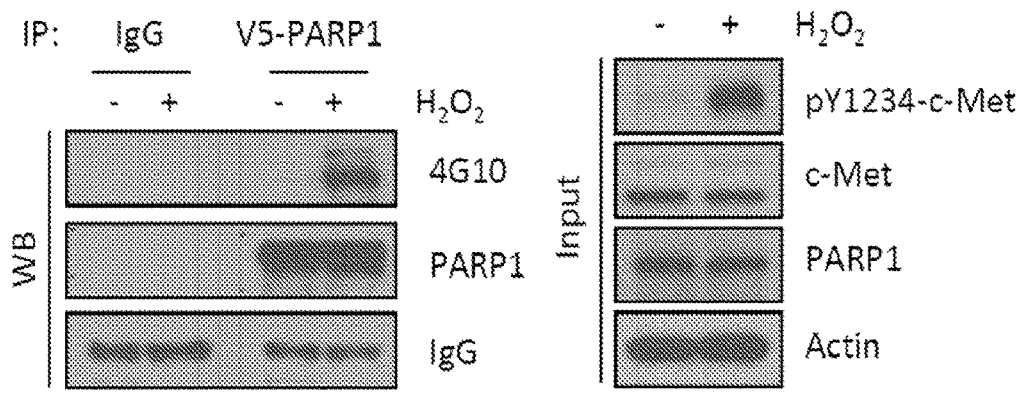
Figure 12E:
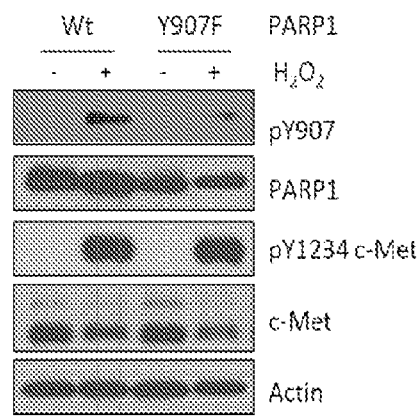
Figure 12F:
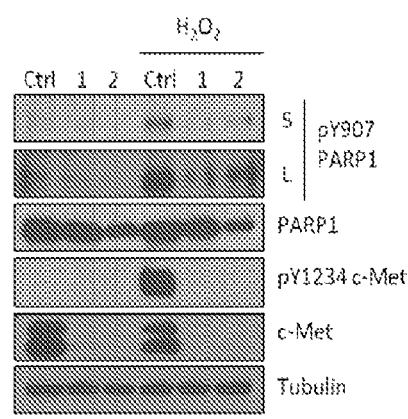

Given that c-Met and PARP1 physically associate in vive (FIGS. 1F-G and 7A-F) and that the kinase activity of c-Met enhances DNA repair in response to DNA damage or PARP inhibition, it was expected that c-Met as a tyrosine kinase could also phosphorylate PARP1 under oxidative stress. Indeed, $H_2O_2$ induced PARP1 tyrosine phosphorylation following co-transfection of Flag-tagged c-Met and V5-tagged PARP1 (FIG. 3C). Using the software program (NetworKIN V2.0) (Linding et al., 2007), Tyr907 (Y907), which is located on the H-Y-E motif in the catalytic domain of PARP1 (Ruf et al., 1996), was predicted as the only c-Met phosphorylation site. An in vitro kinase assay also showed that phosphorylation of PARP1 by γ-$^{32}$P incorporation was substantially reduced in a Y907F mutant compared with a Y986F mutant, another Tyr residue in the H-Y-E domain (FIGS. 12A-B). These results suggest that Y907 is a bona fide c-Met phosphorylation site.

Figure 3D:
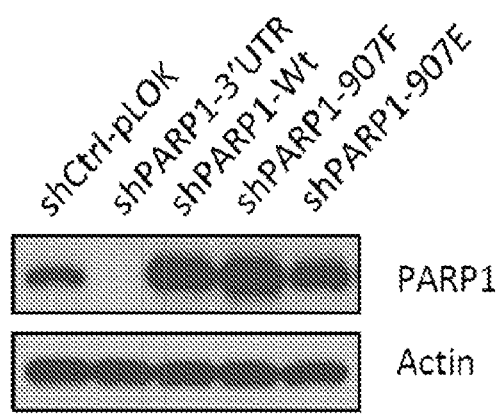
Figure 3E:
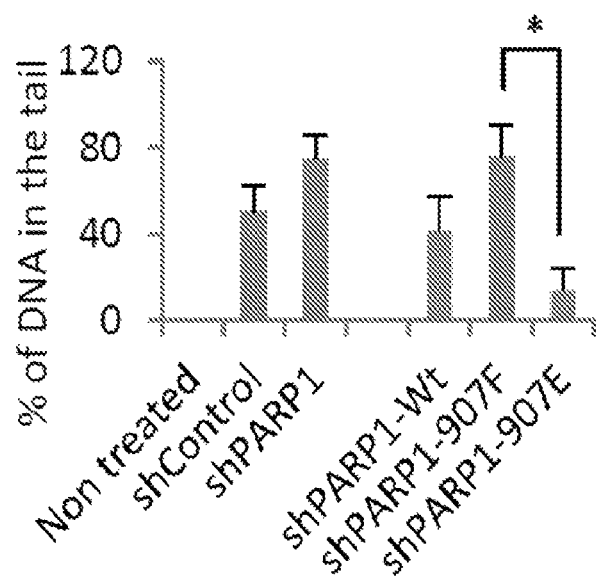
Figure 3F:
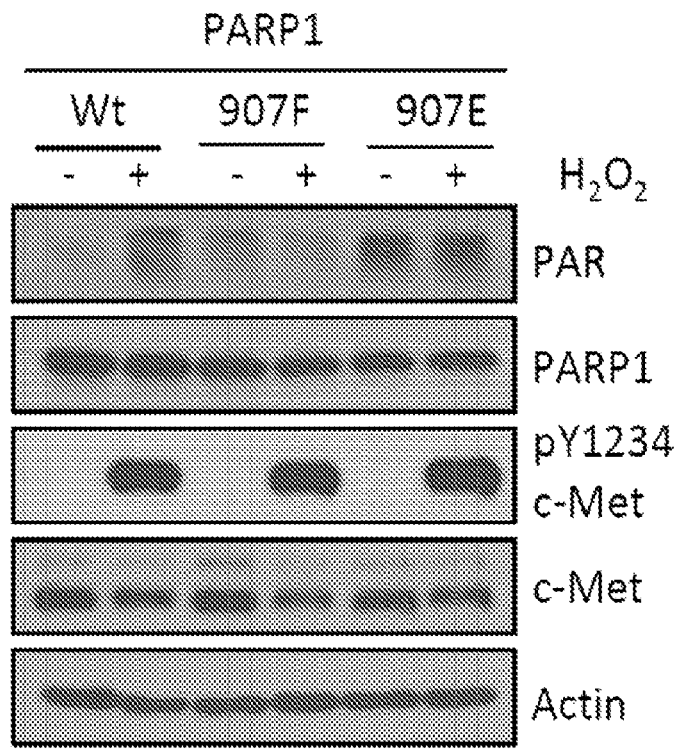
Figure 3G:
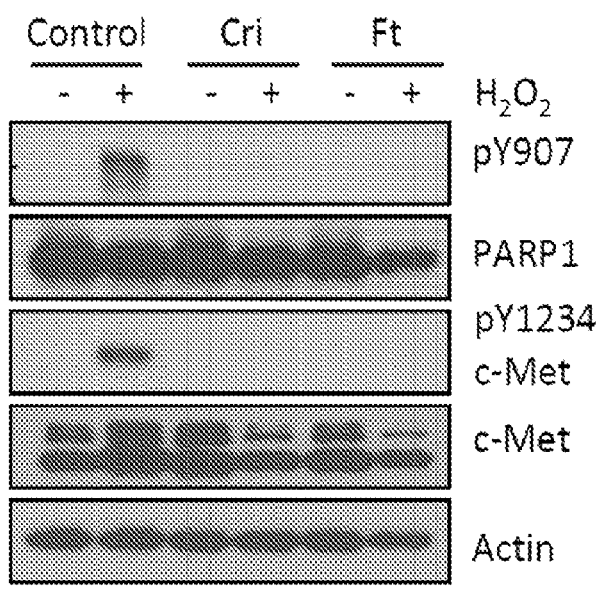

Since Y907 is located within the catalytic domain of PARP1, it was next asked whether Y907 phosphorylation affects the function of PARP1. Wild-type, Y907F (non-phosphorylatable), or Y907E (phosphomimetic) mutant PARP1 was stably expressed in PARP1-knockdown MDA-MB-231 cells (FIG. 3D) and measured $H_2O_2$-induced DNA damage by comet assay. As expected, PARP1 knockdown cells had more DNA damage than control cells (FIG. 3E, panel 2 vs. 3). Re-expression of wild-type PARP1 (FIG. 3E, panel 4) but not the Y907F mutant (FIG. 3E, panel 5) reduced DNA damage in endogenous PARP1-depleted cells, and cells expressing the Y907E mutant (phosphomimetic) had the least amount of DNA damage (FIG. 3E, panel 6). To determine whether phosphorylation of PARP1 at Y907 affects its activity, the PARylation (PAR) levels between wild-type and mutant PARP1 were compared. As shown in FIG. 3F, cells expressing wild-type PARP1 had increased PAR in response to $H_2O_2$. Interestingly, while the phosphomimetic Y907E mutant had higher levels of PAR than the non-phosphorylatable Y907F mutant, both were relatively unchanged in response to $H_2O_2$, indicating that mutants were no longer sensitive to $H_2O_2$. To further investigate the functional importance of phosphorylated PARP1 at Y907, a specific antibody was generated to detect phosphorylated Y907 (pY907) (FIGS. 12C-F). Both crizotinib and foretinib abolished phosphorylation of PARP1 at Y907 induced by $H_2O_2$(FIG. 3G). These results suggest that $H_2O_2$-induced wild-type PARP1 activity requires Y907 phosphorylation.

Because c-Met attenuates the effect of PARP inhibition (FIG. 2), it was asked whether c-Met-mediated phosphorylation of Y907 of PARP1 affects PARP inhibitor response. Cells expressing wild-type PARP1 treated with or without $H_2O_2$ or expressing the Y907F or Y907E PARP1 mutant were subjected to a PARP enzyme activity assay in increasing concentrations of ABT-888 to measure the $IC_{50}$. The activity of the phosphomimetic Y907E mutant was similar to that of wild-type PARP1 treated with $H_2O_2$ (higher $IC_{50}$) whereas the activity of the non-phosphorylatable Y907F mutant was similar to that of wild-type PARP1 without $H_2O_2$ (lower $IC_{50}$) (FIGS. 13A-B). These results indicate that phosphorylation of PARP1 at Y907 attenuates the inhibitory effect of ABT-888.

Figure 3H:
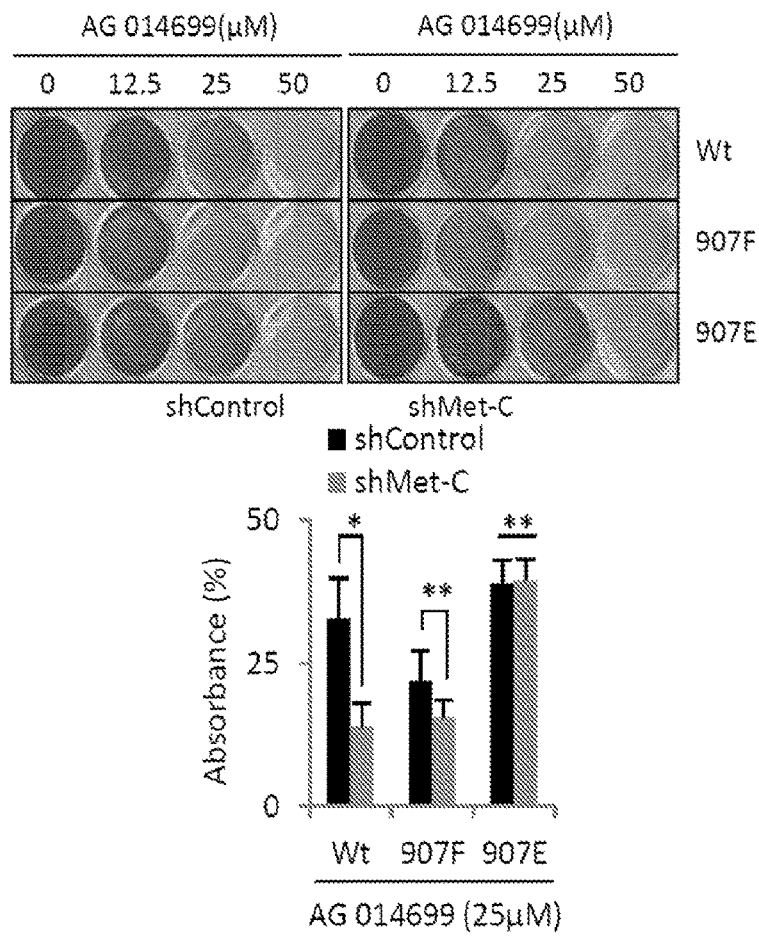
Figure 3I:
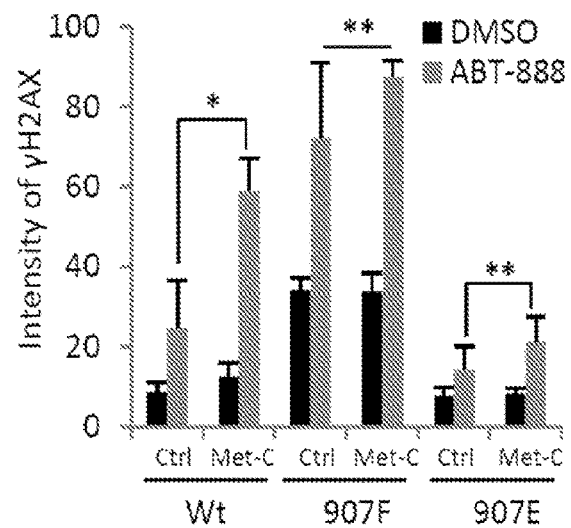

Next, to determine whether PARP1 Y907 phosphorylation is functionally mediated by c-Met, c-Met was knocked down in PARP1-knockdown cells re-expressing wild-type and Y907 mutant PARP1 (FIG. 13C) and treated them with or without ABT-888. The extent of DNA damage in these cells was evaluated by γH2AX foci formation assay. As shown in FIG. 3I, only wild-type PARP1 responded to c-Met knockdown, as indicated by the increased γH2AX foci (FIG. 3I, inset 1 vs. 4). Knocking down c-Met, however, had no apparent effect on cells expressing either the Y907F or Y907E mutant. The non-phosphorylatable Y907F mutant (FIG. 3I, inset 2 vs. 5) had higher γH2AX foci formation than the phosphomimetic Y907E mutant (FIG. 3I, inset 3 vs. 6) in response to ABT-888 in both control and c-Met knockdown cells. In addition, clonogenic cell survival (FIG. 3H) and cell viability assays (FIGS. 13D-E) also showed consistent results in which knockdown of c-Met rendered cells expressing wild-type PARP1 more sensitive to PARP inhibitors, ABT-888 and AG014699. Clonogenic cell survival and cell viability were similar between wild-type PARP1- and Y907E-expressing cells in the presence of c-Met (left, FIGS. 3H and 13D-E) as well as between wild-type PARP1- and Y907F-expressing cells in the absence of c-Met (right, FIGS. 3H and 13D-E). These findings together provide strong evidence to support that phosphorylation of PARP1 Y907 attenuates PARP inhibitor response and DNA damage in a c-Met-dependent manner.

Figure 4B:
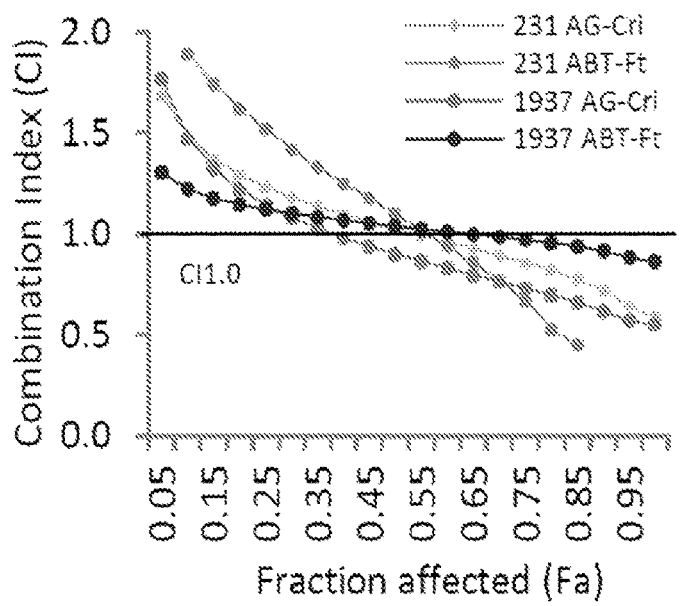
(FIG. 4B) Synergistic effect of inhibiting c-Met and PARP in TNBC cell lines (MBA-MD-231 and HCC1937) was measured by cell viability assay.
Figure 4C:
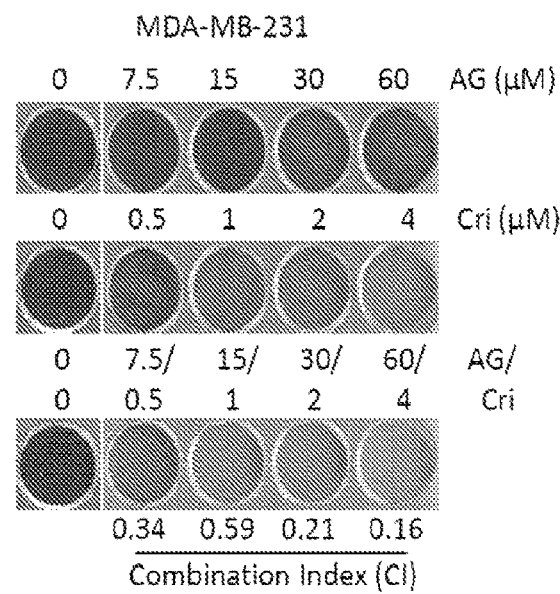
(FIGS. 4C and 4E) Synergistic effect of c-Metinhibitor crizotinib (Cri) and PARP inhibitor AG014699 (AG) was measured by clonogenic cell survival assay in MBA-MD-231 cells and HCC1937 cells.
Figure 4D:
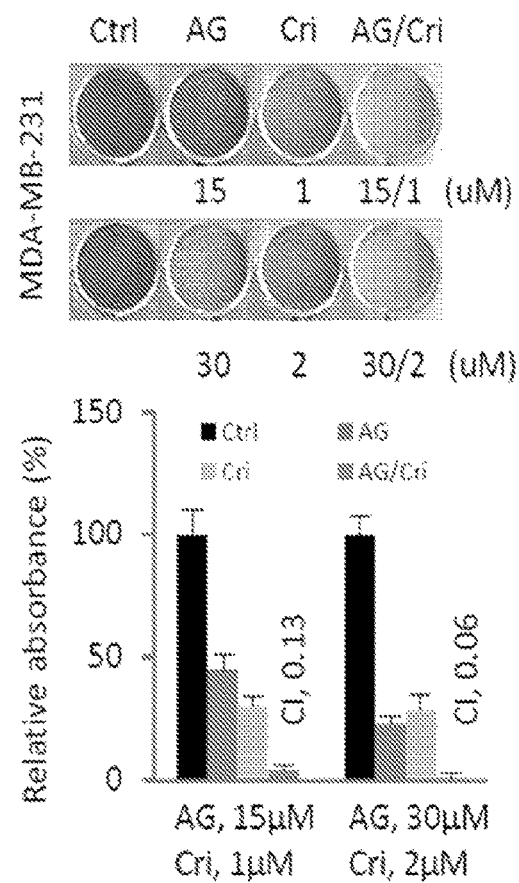
(FIGS. 4D and 4F) Synergistic effect of c-Met and PARP inhibitors (AG014699 and Crizotinib) by clonogenic cell survival assay in MBA-MD-231 cells and HCC1937 cells. Data shown as mean±SEM of triplicated experiments (n=3). *P<0.05, t-test.
Figure 4E:
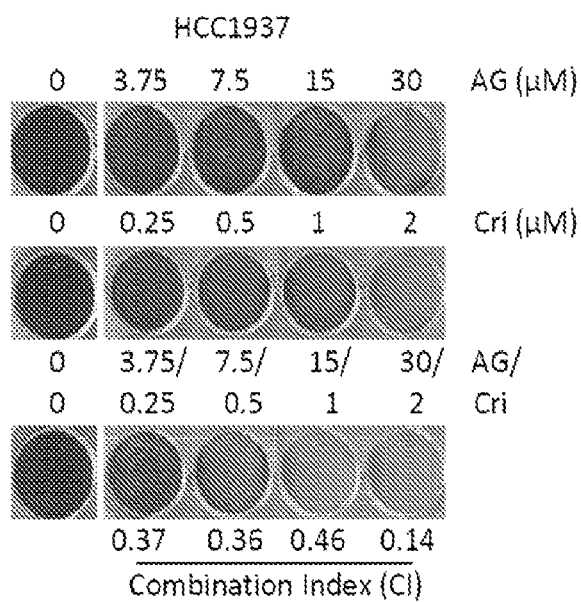
Figure 4F:
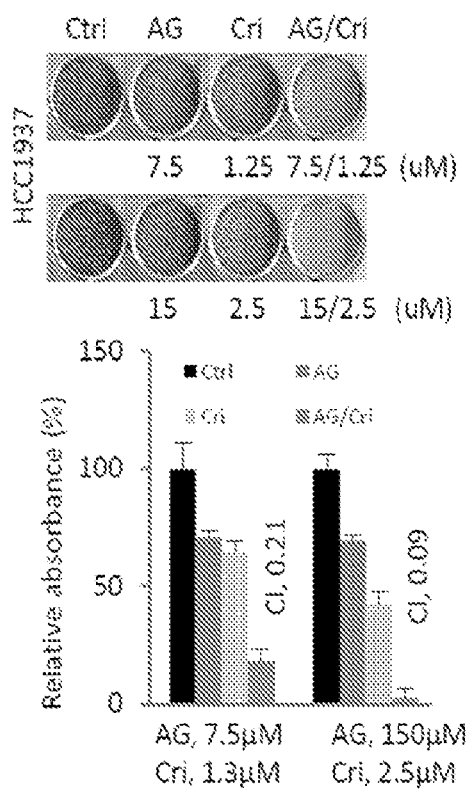
Figure 4G:
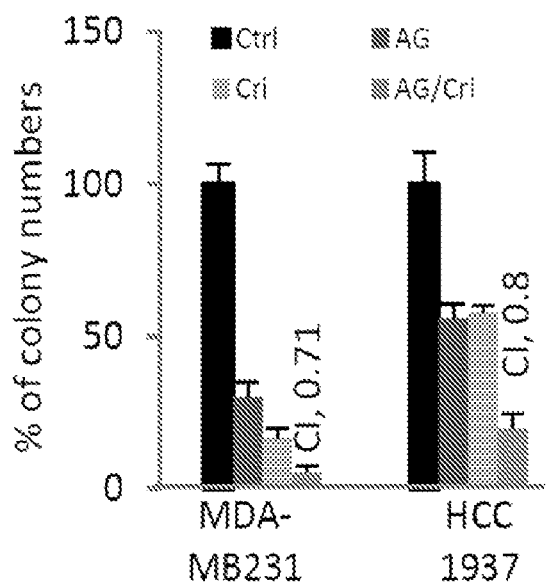
(FIG. 4G) Synergistic effect of c-Met inhibitor crizotinib (Cri) and PARP inhibitor AG014699 (AG) was measured by soft agar assay in MBA-MD-231 cells and HCC1937 cells.
Figure 4H:
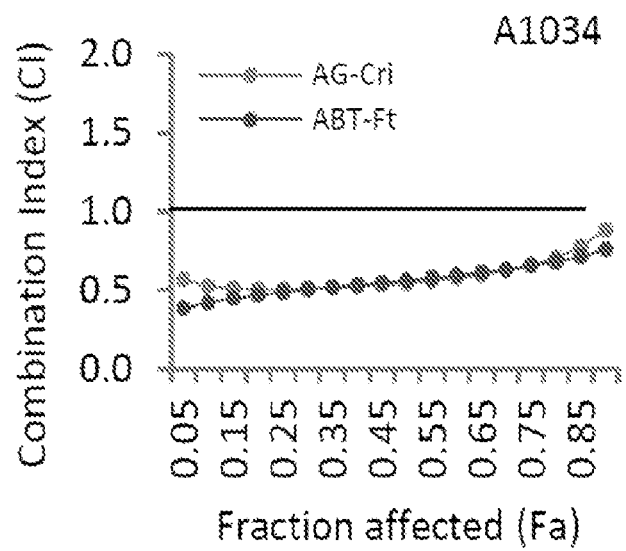
(FIG. 4H) Synergistic effect of c-Met and PARP inhibition A1034 cells as measured by cell viability assay.
Figure 4I:
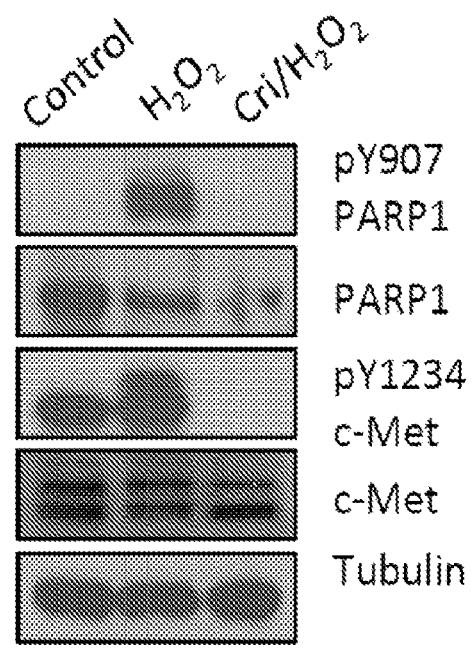
(FIG. 4I) A1034 cells were treated with $H_2O_2$ or crizotinib pre-treatment plus $H_2O_2$, and cell lysates were subjected to Western blot with the indicated antibodies.

Example 4—Clinical Relevance and Potential Therapeutic Strategy Targeting PARP1 and c-Met in TNBC The specific antibody against pY907 was characterized first in clinical patient samples (FIG. 14A). Next, expression of pY907-PARP1 in a breast cancer tissue microarray by immunohistochemical (IHC) staining demonstrated a positive correlation between pY907-PARP1 and c-Met expression in both TNBC and non-TNBC (FIGS. 4A and 14B). Likewise, high ROS (8-OHdG) also correlated with high pY907-PARP1 expression (FIG. 14C). These results suggest that intracellular ROS may be a critical inducer of PARP1 Y907 phosphorylation in a c-Met-dependent manner that attenuates PARP inhibitor response. In addition, this mechanism provides a potential clinical application in which inhibition of c-Met may enhance the sensitivity to PARP inhibition. To determine its feasibility, the efficacy of combining c-Met inhibitors (foretinib and crizotinib) and PARP inhibitors (ABT-888 and AG-014699) was examined first. Both the ABT-888/foretinib and AG-014699/crizotinib combinations demonstrated synergistic cell growth inhibition in MDA-MB-231 and HCC1937 TNBC cells (FIG. 4B) but not in MCF10A mammary epithelial cells (FIG. 15A). The combined treatment of AG-014699/crizotinib also suppressed both clonogenicity (FIGS. 4C and 4E) and anchorage-independent growth (FIGS. 4G and 15B). Similar inhibitory effects on clonogenic cell survival were observed for the ABT-888/foretinib combination (FIG. 15C). Synthetic inhibition of c-Met and PARP1 was also observed in another breast cancer cell line, BT549 (FIG. 15D). $H_2O_2$-induced phosphorylation of Y907-PARP1 was abolished by c-Met inhibition (FIG. 15E). In addition to human breast cancer cell lines, the effect of the combination treatment was evaluated in two mouse mammary tumor cell lines derived from a TNBC transgenic mouse model expressing constitutively active human c-Met (Knight et al., 2013). Combined treatment with c-Met and PARP inhibitors synergistically inhibited mouse tumor cell growth (FIGS. 4H and 15F). Also, pY907-PARP was stimulated by $H_2O_2$ and abolished by c-Met inhibition in these mouse cell lines (FIGS. 4I and 15G).

Figure 4J:
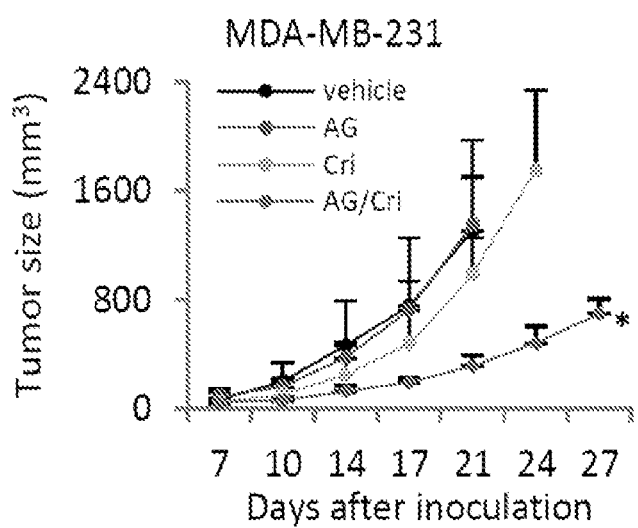
(FIG. 4J) MDA-MB-231 cells were inoculated into the mammary fat pad of nude mice (n=10 per group). Crizotinib (5 mg/kg), AG014699 (5 mg/kg), or the combination was orally administrated 5 days per week for indicated time. Tumor size was measured at the indicated times.
Figure 4K:
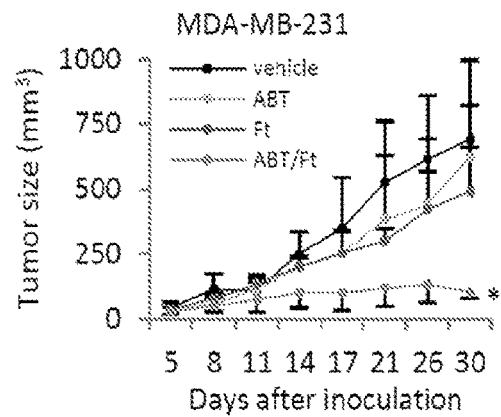
(FIG. 4K) MDA-MB-231 cells were inoculated into the mammary fat pad of nude mice (n=10 per group). foretinib (5 mg/kg), ABT-888 (25 mg/kg), or the combination was orally administrated 5 days per week for indicated time. Tumor size was measured at the indicated times. (FIGS. L-O) TUNEL, Ki67, γH2AX, and PARP1-pY907 staining of MDA-MB-231 xenograft tumor tissues. Quantitation is shown.
Figure 4L:
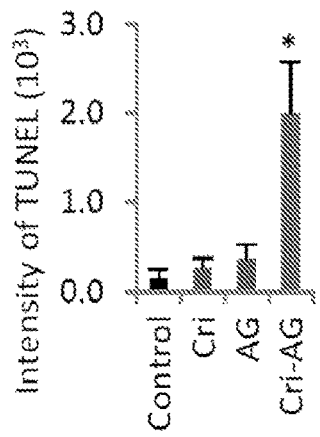
(FIG. 4P) Synergistic effect of c-Met and PARP inhibition MCF-7/c-Met cells as measured by cell viability assay.
(FIG. 4Q) MCF-7/c-Met cells were treated with $H_2O_2$ or crizotinib pre-treatment plus $H_2O_2$, and cell lysates were subjected to Western blot with the indicated antibodies.
(FIG. 4R) MCF-7 cells with ectopic expression of c-Met were inoculated into the mammary fat pad of nude mice (n=10 per group). Crizotinib (5 mg/kg), AG014699 (5 mg/kg), or the combination was orally administrated 5 days per week for indicated time. Tumor size was measured at the indicated times.
Figure 4M:
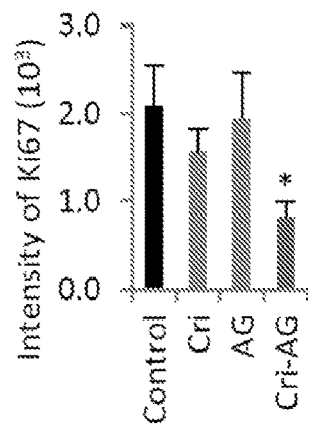
Figure 4N:
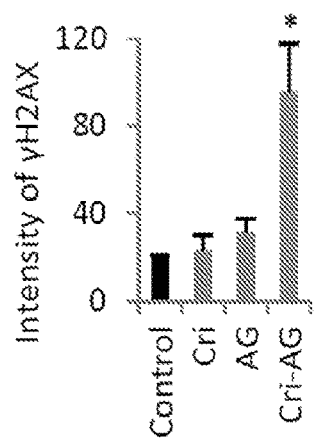
Figure 4O:
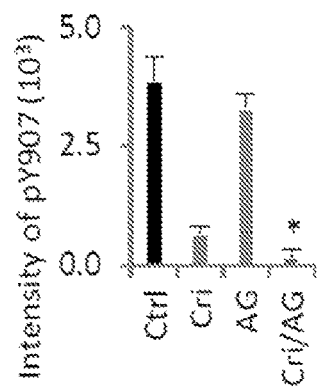
Figure 16A:
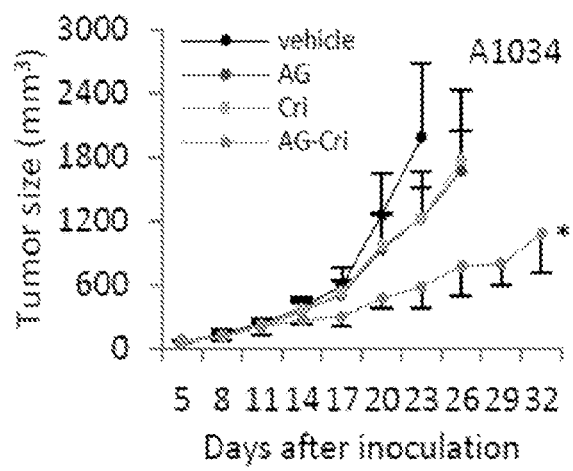
FIGS. 16A-B. Combination treatment of PARP and c-Met inhibits tumor growth.
Figure 16B:
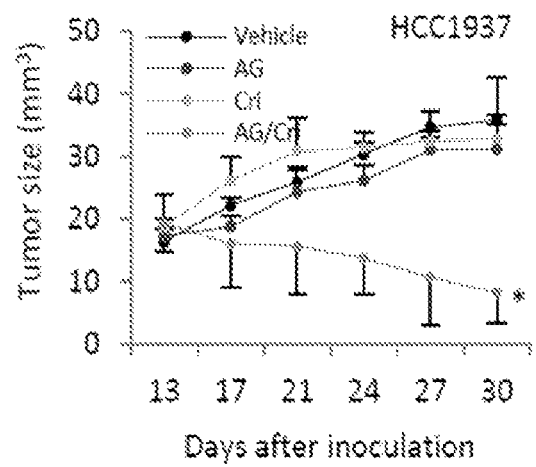
Figure 19:
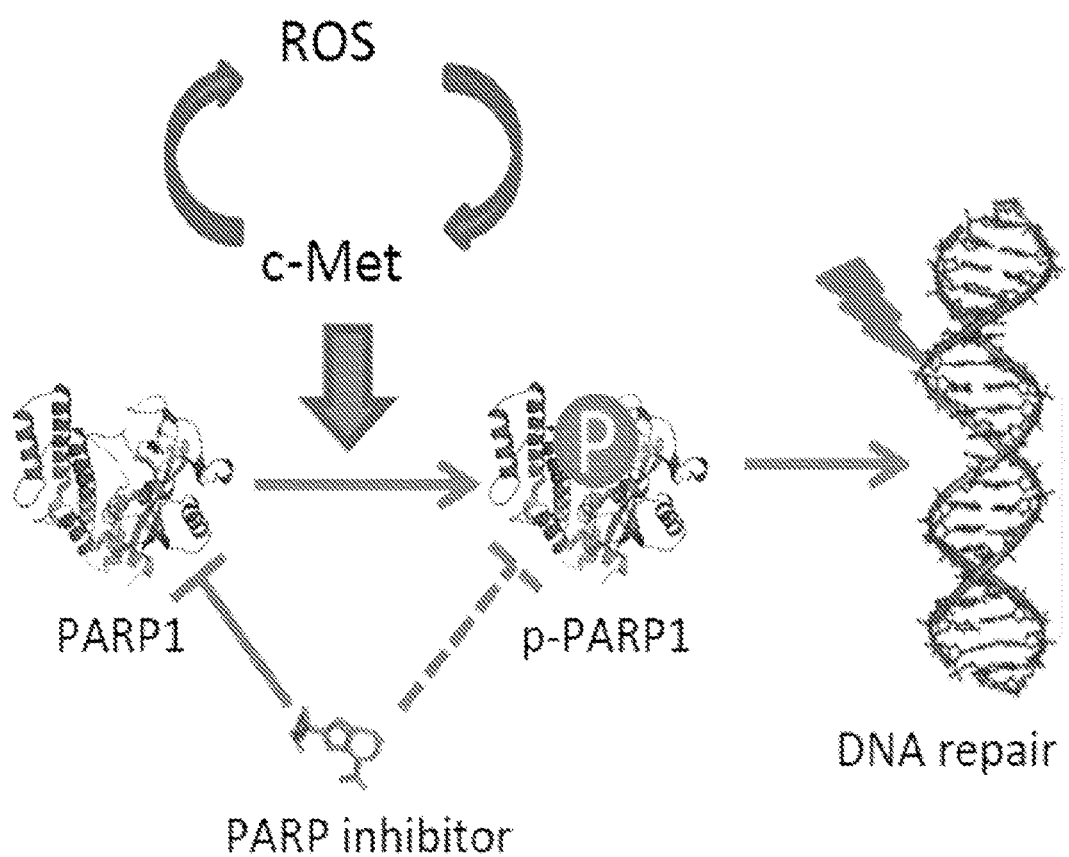
FIG. 19. Proposed model. ROS-activated c-Met phosphorylates PARP1 at Tyr 907. Phosphorylated PARP1 enhances its DNA repair activity, thereby contributing to PARP inhibitor resistance.

Next, the combination of PARP and c-Met inhibitors was evaluated in vivo against established TNBC xenograft models. In MDA-MB-231 xenograft tumor models, combination treatment (AG014699/crizotinib and ABT-888/foretinib) resulted in significantly reduced tumor growth (FIGS. 4J-K). Similar results were also observed in MDA-MB-231 xenograft tumor models in the syngeneic model by using the transgenic mouse cell line, A1034, and another TNBC cell line, HCC1937. The AG014699 and crizotinib combination significantly inhibited tumor growth (FIGS. 16A-B). Increased apoptosis (TUNEL staining, FIG. 4L), reduced cell proliferation (Ki67 staining, FIG. 4M), and more DNA damage (γH2AX staining, FIG. 4N) were observed in MDA-MB-231 xenograft tumor tissues harvested from mice within 24 h after the last treatment. Not surprisingly, PARP1 Y907 phosphorylation was also inhibited by crizotinib (FIG. 4O). In addition, clinical chemistry analysis (FIGS. 17A, B, D, E, G, H) as well as the mice body weight (FIGS. 17C, F, I) suggested that the overall health of the animals was not adversely affected by the combination therapy of AG-014699/crizotinib and ABT-888/foretinib. These results indicate that this combination is effective against TNBC both in vitro and in vivo.

Figure 4P:
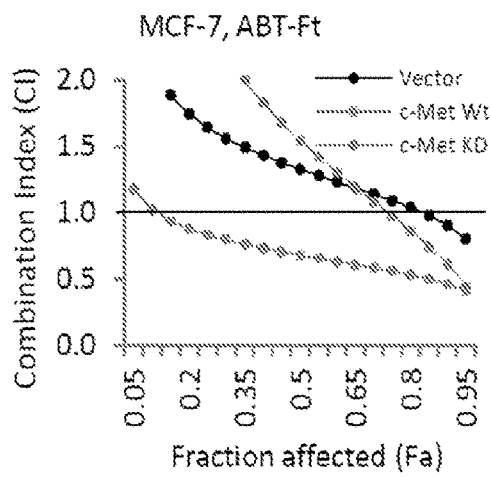
Figure 4Q:
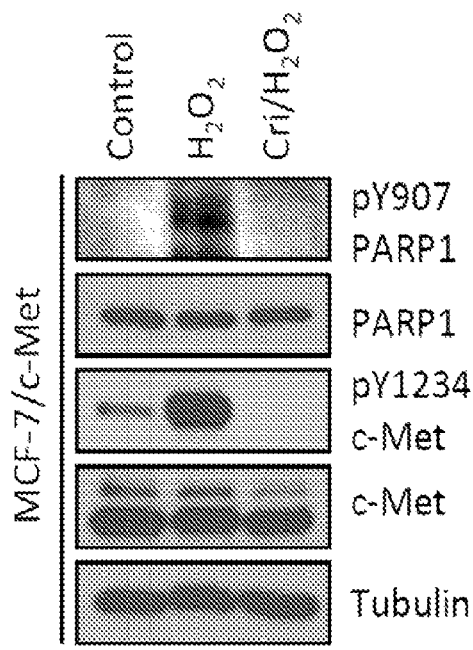
Figure 4R:
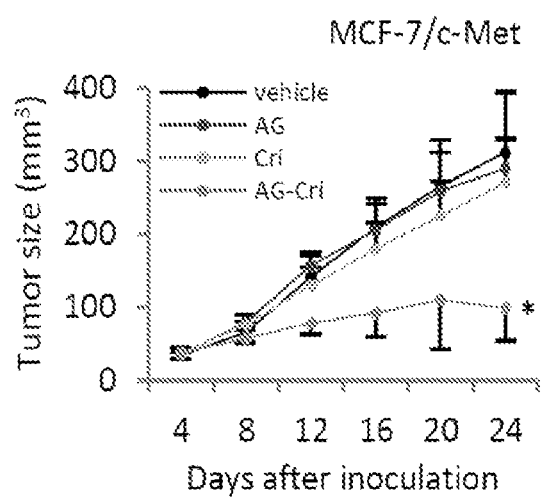
Figure 4S:
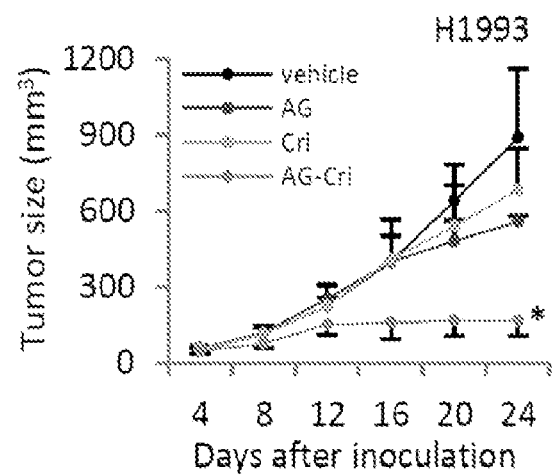

To expand these findings to other cancer types, c-Met was ectopically expressed in non-TNBC cell line, MCF-7 with low expression of c-Met. MCF-7/c-Met showed a similar response as TNBC cell lines. In FIGS. 4P and 14A, only MCF-7 with ectopic expression of c-Met has synergy effect in response to combined treatment of c-Met and PARP inhibitors, but not MCF-7 cells with vector control or kinase dead mutant. More mechanism study revealed that $H_2O_2$ increased phosphorylation of PARP1 at Y907 abolished by the pre-treatment of c-Met inhibitor in the MCF-7 cells with c-Met expression (FIG. 4Q). In addition, similar results were observed in two non-small cell lung cancer cell lines, H1993 with high expression of c-Met and A549 with low expression of c-Met (FIG. 18B) in which the synergistic effect of combining c-Met and PARP inhibitors was only observed in H1993 with high expression of c-Met. Higher c-Met resulted in higher PARP1 Y907 phosphorylation in response to $H_2O_2$ treatment, which can be blocked by c-Met inhibition (FIG. 18C). The combined treatment of AG014699 and crizotinib inhibits tumor growth in H1993 lung cancer and MCF/c-Met breast cancer tumor models (FIGS. 4R-S). Taken together, c-Met-mediated phosphorylation of PARP1 controls PARP inhibitor response in TNBC and other cancer types with c-Met expression. These results suggest that pY907-PARP1 can be used as a biomarker to stratify patients for the single PARP inhibitor or combined treatment of c-Met and PARP inhibitors in the clinic.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 7,928,105
U.S. Pat. No. 8,124,606
U.S. Pat. No. 8,236,802
U.S. Pat. No. 8,450,323
WO 2006/110816
WO 2007/084532
WO 2008/064157
WO 2008/083027
WO 2011/014681
Anders et al., Poly(ADP-Ribose) polymerase inhibition: "targeted" therapy for triple-negative breast cancer. *Clinical Cancer Research*, 16:4702-4710, 2010.
Anders et al., Pharmacokinetics and efficacy of PEGylated liposomal doxorubicin in an intracranial model of breast cancer. *PLoS One*, 8:e61359, 2013.
Birchmeier et al., Met, metastasis, motility and more. *Nat. Rev. Mol. Cell. Biol.*, 4:915-925, 2003.
Boccaccio and Comoglio, Invasive growth: a MET-driven genetic programme for cancer and stem cells. *Nat. Rev. Cancer*, 6:637-645, 2006.
Bryant et al., Specific killing of BRCA2-deficient tumours with inhibitors of poly(ADP-ribose) polymerase. *Nature*, 434:913-917, 2005.
Carey et al., Triple-negative breast cancer: disease entity or title of convenience? *Nature reviews. Clinical Oncology*, 7:683-692, 2010.
Casaletto and McClatchey, Spatial regulation of receptor tyrosine kinases in development and cancer. *Nature Reviews Cancer*, 12:387-400, 2012.
Castaldi et al., How appropriate is the use of rehabilitation facilities? Assessment by an evaluation tool based on the AEP protocol. *J. Prev. Med. Hyg.*, 51:116-120, 2010.
Chou, Drug combination studies and their synergy quantification using the Chou-Talalay method. *Cancer Res.*, 70:440-446, 2010.
Christensen et al., c-Met as a target for human cancer and characterization of inhibitors for therapeutic intervention. *Cancer Lett.*, 225:1-26, 2005.
Donawho et al., ABT-888, an orally active poly(ADP-ribose) polymerase inhibitor that potentiates DNA-damaging agents in preclinical tumor models. *Clin. Cancer Res.*, 13:2728-2737, 2007.
Du et al., Syntaxin 6-mediated Golgi translocation plays an important role in nuclear functions of EGFR through microtubule-dependent trafficking. *Oncogene*, 33:756-770, 2014.
Eisen et al., Cluster analysis and display of genome-wide expression patterns. *Proc. Natl. Acad. Sci. U.S.A*, 95:14863-14868, 1998.
Farmer et al., Targeting the DNA repair defect in BRCA mutant cells as a therapeutic strategy. *Nature*, 434:917-921, 2005.
Fischer et al., Reactive oxygen species mediate Met receptor transactivation by G protein-coupled receptors and the epidermal growth factor receptor in human carcinoma cells. *J. Biol. Chem.*, 279:28970-28978, 2004.
Foulkes et al., Triple-negative breast cancer. *The New England Journal of Medicine*, 363:1938-1948, 2010.
Gastaldi et al., The Met oncogene and basal-like breast cancer: another culprit to watch out for? *Breast Cancer Research*, 12:208, 2010.
Gelmon et al., Olaparib in patients with recurrent high-grade serous or poorly differentiated ovarian carcinoma or triple-negative breast cancer: a phase 2, multicentre, open-label, non-randomised study. *Lancet Oncol.*, 12:852-861, 2011.
Gibson and Kraus, New insights into the molecular and cellular functions of poly(ADP-ribose) and PARPs. *Nat. Rev. Mol. Cell Biol.*, 13:411-424, 2012.
Hampson et al., Validation of an ELISA for the determination of rituximab pharmacokinetics in clinical trials subjects. *J. Immunol. Methods*, 360:30-38, 2010.
Hsu et al., Definition of PKC-alpha, CDK6, and MET as therapeutic targets in triple-negative breast cancer. *Cancer Res.*, 74:4822-4835, 2014.
Irani et al., Mitogenic signaling mediated by oxidants in Ras-transformed fibroblasts. *Science*, 275:1649-1652, 1997.
Jagadeeswaran et al., Activation of HGF/c-Met pathway contributes to the reactive oxygen species generation and motility of small cell lung cancer cells. *American Journal of Physiology. Lung Cellular and Molecular Physiology*, 292:L1488-1494, 2007.
Knight et al., Met synergizes with p53 loss to induce mammary tumors that possess features of claudin-low breast cancer. *Proc. Natl. Acad. Sci. U.S.A*, 110:E1301-1310, 2013.

Kummar et al., Phase 0 clinical trial of the poly (ADP-ribose) polymerase inhibitor ABT-888 in patients with advanced malignancies. *J. Clin. Oncol.*, 27:2705-2711, 2009.

Ledermann et al., Olaparib maintenance therapy in patients with platinum-sensitive relapsed serous ovarian cancer: a preplanned retrospective analysis of outcomes by BRCA status in a randomised phase 2 trial. *The Lancet Oncology*, 15:852-861, 2014.

Lehmann et al., Identification of human triple-negative breast cancer subtypes and preclinical models for selection of targeted therapies. *J. Clin. Invest.*, 121:2750-2767, 2011.

Liedtke et al., Response to neoadjuvant therapy and long-term survival in patients with triple-negative breast cancer. *Journal of Clinical Oncology*, 26:1275-1281, 2008.

Lindahl, Instability and decay of the primary structure of DNA. *Nature*, 362:709-715, 1993.

Linding et al., Systematic discovery of in vivo phosphorylation networks. *Cell*, 129:1415-1426, 2007.

Liu et al., EGFR expression correlates with decreased disease-free survival in triple-negative breast cancer: a retrospective analysis based on a tissue microarray. *Medical Oncology*, 29:401-405, 2012.

Lord and Ashworth, Mechanisms of resistance to therapies targeting BRCA-mutant cancers. *Nat. Med.*, 19:1381-1388, 2013.

Luo and Kraus, On PAR with PARP: cellular stress signaling through poly(ADP-ribose) and PARP-1. *Genes Dev.*, 26:417-432, 2012.

Nowsheen et al., Synthetic lethal interactions between EGFR and PARP inhibition in human triple negative breast cancer cells. *PLoS ONE*, 7:e46614, 2012.

O'Shaughnessy et al., Iniparib plus chemotherapy in metastatic triple-negative breast cancer. *The New England Journal of Medicine*, 364:205-214, 2011.

O'Shaughnessy et al., A randomized phase III study of iniparib (BSI-201) in combination with gemcitabine/carboplatin (G/C) in metastatic triple-negative breast cancer (TNBC). *Journal of Clinical Oncology*, 29:abstr 1007, 2011.

Radisky et al., Rac1b and reactive oxygen species mediate MMP-3-induced EMT and genomic instability. *Nature*, 436:123-127, 2005.

Rouleau et al., PARP inhibition: PARP1 and beyond. *Nature Reviews Cancer*, 10:293-301, 2010.

Ruf et al., Structure of the catalytic fragment of poly(ADP-ribose) polymerase from chicken. *Proc. Natl. Acad. Sci. U.S.A*, 93:7481-7485, 1996.

Sokal et al., *A Statistical Method for Evaluating Systematic Relationships*, University of Kansas, 1958.

Speers et al., Identification of novel kinase targets for the treatment of estrogen receptor-negative breast cancer. *Clin. Cancer Res.*, 15:6327-6340, 2009.

Trachootham et al., Targeting cancer cells by ROS-mediated mechanisms: a radical therapeutic approach? *Nat. Rev. Drug Discov.*, 8:579-591, 2009.

Turashvili et al., P-cadherin expression as a prognostic biomarker in a 3992 case tissue microarray series of breast cancer. *Mod. Pathol.*, 24:64-81, 2011.

Turner et al., Hallmarks of 'BRCAness' in sporadic cancers. *Nature Reviews Cancer*, 4:814-819, 2004.

Tutt et al., Oral poly(ADP-ribose) polymerase inhibitor olaparib in patients with BRCA1 or BRCA2 mutations and advanced breast cancer: a proof-of-concept trial. *Lancet*, 376:235-244, 2010.

Zagouri et al., High MET expression is an adverse prognostic factor in patients with triple-negative breast cancer. *Br. J. Cancer*, 108:1100-1105, 2013.

---

What is claimed is:

1. A method of treating a cancer patient, the method comprising identifying that the patient has treating a patient determined to have a cancer expressing Tyr907 phosphorylated PARP1, and administering to the patient with a therapeutically effective amount of a combination of a PARP1 inhibitor and MET inhibitor.

2. The method of claim 1, wherein the step of identifying further comprises assaying a sample of the cancer to determine a phosphorylation status of PARP1 Tyr907 in the cancer.

3. The method of claim 1, wherein the assaying comprises measuring the level of phosphorylation of PARP1 Tyr907.

4. The method of claim 1, wherein assaying comprises contacting the sample with an antibody that binds specifically to phosphorylated PARP1 Tyr907.

5. The method of claim 1, wherein assaying comprises performed a Western blot, ELISA, immunoprecipitation, radioimmunoassay, or immunohistochemical assay.

6. The method of claim 1, wherein the cancer is a breast cancer, renal cancer, lung cancer, or ovarian cancer.

7. The method of claim 6, wherein the breast cancer is a triple-negative breast cancer.

8. The method of claim 1, wherein the PARP1 inhibitor is olaparib, ABT-888 (Veliparib), BSI-201 (Iniparib), BMN 673, Rucaparib (AG-014699, PF-01367338), AG14361, INO-1001, A-966492, PJ34, or MK-4827.

9. The method of claim 1, wherein the MET inhibitor is INCB28060, ARQ197 (tivantinib), AMG458, GSK1363089 (XL880 or foretinib), E7050 (golvatinib), MK-2461, BMS-777607, JNJ-38877605, XL184 (cabozantinib), AMG337, ARQ197, MGCD265, PF04217903 or PF02341066 (crizotinib).

10. The method of claim 1, wherein the PARP1 inhibitor is administered essentially simultaneously with the MET inhibitor.

11. The method of claim 1, wherein the patient has previously undergone at least one round of anti-cancer therapy.

12. The method of claim 1, wherein the patient is a human.

13. The method of claim 1, further comprising administering a second anticancer therapy.

14. The method of claim 13, wherein the second anticancer therapy is a surgical therapy, chemotherapy, radiation therapy, cryotherapy, hormonal therapy, toxin therapy, immunotherapy, or cytokine therapy.

15. A method of sensitizing a cancer to a PARP1 inhibitor-based anticancer therapy, the method comprising identifying that the cancer expresses Tyr907 phosphorylated PARP1, administering an effective amount of a MET inhibitor to a patient having the cancer, and administering a PARP1 inhibitor-based anticancer therapy to the patient having the cancer.

16. The method of claim 15, wherein the PARP1 inhibitor-based anticancer therapy is administered essentially simultaneously with said MET inhibitor.

17. The method of claim 15, wherein the MET inhibitor is INCB28060, ARQ197 (tivantinib), AMG458, GSK1363089 (XL880 or foretinib), E7050 (golvatinib), MK-2461, BMS-777607, JNJ-38877605, XL184 (cabozantinib), AMG337, ARQ197, MGCD265, PF04217903 or PF02341066 (crizotinib).

18. The method of claim 15, wherein the PARP1 inhibitor is olaparib, ABT-888 (Veliparib), BSI-201 (Iniparib), BMN 673, Rucaparib (AG-014699, PF-01367338), AG14361, INO-1001, A-966492, PJ34, or MK-4827.

* * * * *

UNITED STATES PATENT AND TRADEMARK OFFICE
CERTIFICATE OF CORRECTION

| | |
|---|---|
| PATENT NO. | : 10,451,610 B2 |
| APPLICATION NO. | : 15/514928 |
| DATED | : October 22, 2019 |
| INVENTOR(S) | : Mien-Chie Hung et al. |

It is certified that error appears in the above-identified patent and that said Letters Patent is hereby corrected as shown below:

In the Claims

In Claim 1, Column 37, Lines 44-45, delete "treating a patient determined to have".

In Claim 1, Column 37, Line 46, delete "with".

Page 1 of 1

Signed and Sealed this
Twenty-first Day of July, 2020

Andrei Iancu
*Director of the United States Patent and Trademark Office*

SEQUENCE LISTING

```
<160> NUMBER OF SEQ ID NOS: 13

<210> SEQ ID NO 1
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 1

Ala Asp Met Val Ser Lys Ser Ala Asn Tyr Cys His Thr Ser Gln Gly
1               5                   10                  15

Asp

<210> SEQ ID NO 2
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 2
ccatccagaa tgtcattct                                             19

<210> SEQ ID NO 3
<211> LENGTH: 18
<212> TYPE: DNA
<213> ORGANISM: Artificial Sequence
<220> FEATURE:
```

<223> OTHER INFORMATION: Synthetic polynucleotide

<400> SEQUENCE: 3
gcattaaagc agcgtatc                                                      18

<210> SEQ ID NO 4
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 4
gcattaaagc agcgtatc                                                      18

<210> SEQ ID NO 5
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 5
tgtgttgtat ggtcaataa                                                     19

<210> SEQ ID NO 6
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 6
ccttcagaag gttgctgagt a                                                  21

<210> SEQ ID NO 7
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 7
tggaaagatg ttaagcattt a                                                  21

<210> SEQ ID NO 8
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 8
ttcatttcta atacctgcc                                                     19

<210> SEQ ID NO 9
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 9
ttaagtcaca taatcgatc                                                     19

```
<210> SEQ ID NO 10
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 10
ttcagtacaa ttaggtggg                                                  19

<210> SEQ ID NO 11
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 11
ttgttcagca gattccatg                                                  19

<210> SEQ ID NO 12
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 12
tctttaagac agctaagag                                                  19

<210> SEQ ID NO 13
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 13
tattaaatga ctctttggc                                                  19
```